US008058253B2

(12) United States Patent
Draghia-Akli et al.

(10) Patent No.: US 8,058,253 B2
(45) Date of Patent: Nov. 15, 2011

(54) GROWTH HORMONE RELEASING HORMONE TREATMENT TO DECREASE CHOLESTEROL LEVELS

(75) Inventors: Ruxandra Draghia-Akli, Houston, TX (US); Amir S. Khan, Houston, TX (US); Marta L. Fiorroto, Houston, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 0 days.

(21) Appl. No.: 12/307,733

(22) PCT Filed: Jul. 5, 2007

(86) PCT No.: PCT/US2007/072851
§ 371 (c)(1),
(2), (4) Date: Aug. 6, 2009

(87) PCT Pub. No.: WO2008/006019
PCT Pub. Date: Jan. 10, 2008

(65) Prior Publication Data
US 2010/0010467 A1    Jan. 14, 2010

Related U.S. Application Data

(60) Provisional application No. 60/819,013, filed on Jul. 6, 2006.

(51) Int. Cl.
*A61K 48/00* (2006.01)
*C12P 21/06* (2006.01)
*C12N 15/09* (2006.01)
*C12N 15/00* (2006.01)
*C12N 5/00* (2006.01)

(52) U.S. Cl. .................. 514/44 R; 424/93.1; 424/93.2; 435/69.1; 435/69.4; 435/320.1; 435/325; 435/455

(58) Field of Classification Search ................. None
See application file for complete search history.

(56) References Cited

U.S. PATENT DOCUMENTS

| | | | |
|---|---|---|---|
| 4,223,019 A | 9/1980 | Momany et al. | |
| 4,223,020 A | 9/1980 | Momany et al. | |
| 4,223,021 A | 9/1980 | Momany et al. | |
| 4,224,316 A | 9/1980 | Momany et al. | |
| 4,226,857 A | 10/1980 | Momany et al. | |
| 4,228,156 A | 10/1980 | Momany et al. | |
| 4,228,158 A | 10/1980 | Momany et al. | |
| 4,410,512 A | 10/1983 | Bowers et al. | |
| 4,833,166 A | 5/1989 | Grosvenor et al. | |
| 4,839,344 A | 6/1989 | Bowers et al. | |
| 5,023,322 A | 6/1991 | Kovacs et al. | |
| 5,036,045 A | 7/1991 | Thorner | |
| RE33,699 E | 9/1991 | Drengler | |
| 5,061,690 A | 10/1991 | Kann et al. | |
| 5,084,442 A | 1/1992 | Felix et al. | |
| 5,134,120 A | 7/1992 | Boyd et al. | |
| 5,137,872 A | 8/1992 | Seely et al. | |
| 5,292,721 A | 3/1994 | Boyd et al. | |
| 5,439,440 A | 8/1995 | Hofmann | |
| 5,486,505 A | 1/1996 | Bowers et al. | |
| 5,696,089 A | 12/1997 | Felix et al. | |
| 5,702,359 A | 12/1997 | Hofmann et al. | |
| 5,756,264 A | 5/1998 | Schwartz et al. | |
| 5,776,901 A | 7/1998 | Bowers et al. | |
| 5,792,747 A | 8/1998 | Schally et al. | |
| 5,846,936 A | 12/1998 | Felix et al. | |
| 5,847,066 A | 12/1998 | Coy et al. | |
| 2005/0004060 A1 | 1/2005 | Draghia-Akli et al. | |
| 2005/0031549 A1 | 2/2005 | Quay et al. | |

FOREIGN PATENT DOCUMENTS

| | | |
|---|---|---|
| WO | 95/19805 | 7/1995 |
| WO | 96/12006 | 4/1996 |
| WO | 96/12520 | 5/1996 |
| WO | 97/07826 | 3/1997 |

OTHER PUBLICATIONS

Montero et al, J. Mol. Endo. 25:157-168, 2000.*
Acsadi, G., et al., Human dystrophin expression in mdx mice after intramuscular injection of DNA constructs., Nature, Aug. 29, 1991;352(6338):815-8.
Ahn, C. W., et al, Effects of growth hormone on insulin resistance and atherosclerotic risk factors in obese type 2 diabetic patients with poor glycaemic control, Clin Endocrinol (Oxf)., Apr. 2006;64(4):444-9.
Aihara, H., et al., Gene transfer into muscle by electroporation in vivo, Nat Biotechnol, Sep. 1998;16(9):867-70.
Akhtar, S., Non-viral cancer gene therapy: Beyond delivery, Gene Therapy (2006) 13, 739-740. doi:10.1038/sj.gt.3302692; published online Dec. 1, 2005.
Almendro, N., et al., Cloning of the human platelet endothelial cell adhesion molecule-1 promoter and its tissue-specific expression. Structural and functional characterization, J Immunol., Dec. 15, 1996;157(12):5411-21.
Auchtung, T. L., et al., Growth hormone response to growth hormone-releasing hormone in beef cows divergently selected for milk production, J Anim Sci., May 2001;79(5):1295-300.
Babiuk, L. A., et al., Induction of immune responses by DNA vaccines in large animals, Vaccine, Jan. 30. 2003;21 (7-8):649-58.
Blethen, S. L., et al., Slipped capital femoral epiphysis in children treated with growth hormone. A summary of the National Cooperative Growth Study experience, Horm Res., 1996;46(3):113-6.
Boguszewski, C. L, et al., One year of GH replacement therapy with a fixed low-dose regimen improves body composition, bone mineral density and lipid profile of GH-deficient adults, Eur J Endocrinol., Jan. 2005;152(1):67-75.
Bohlen, P., et al., Isolation and characterization of the porcine hypothalamic growth hormone releasing factor, Biochem Biophys Res Commun., Oct. 31, 1983;116(2):726-34.

(Continued)

*Primary Examiner* — Sumesh Kaushal
(74) *Attorney, Agent, or Firm* — Thomas Kim

(57) ABSTRACT

This invention is related to compositions and methods for decreasing cholesterol levels in a subject. The method utilizes a nucleic acid expression construct that encodes a growth-hormone-releasing-hormone ("GHRH") that is delivered into a tissue of the subject, wherein GHRH is expressed in vivo in the subject.

11 Claims, 18 Drawing Sheets

OTHER PUBLICATIONS

Bollerslev, J., et al., Low-dose GH improves exercise capacity in adults with GH deficiency: effects of a 22-month placebo-controlled, crossover trial, Eur J Endocrinol., Sep. 2005;153(3):379-87.

Boshart, M., et al., A very strong enhancer is located upstream of an immediate early gene of human cytomegalovirus, Cell, Jun. 1985;41(2):521-30.

Bramnert, M., et al., Growth hormone replacement therapy induces insulin resistance by activating the glucose-fatty acid cycle, J Clin Endocrinol Metab., Apr. 2003;88(4):1455-63.

Brown, P. A., et al., Immune-enhancing effects of growth hormone-releasing hormone delivered by plasmid injection and electroporation, Mol Ther., Oct. 2004;10(4):644-51.

Carbonelli, D. L., et al., A plasmid vector for isolation of strong promoters in *Escherichia coli*, FEMS Microbiol Lett., Aug. 1, 1999;177(1):75-82.

Ceda, G. P., et al., The growth hormone (GH)-releasing hormone (GHRH)-GH-somatomedin axis: evidence for rapid inhibition of GHRH-elicited GH release by insulin-like growth factors I and II, Endocrinology, Apr. 1987;120 (4):1658-62.

Chandler, S. D., et al., RNA splicing specificity determined by the coordinated action of RNA recognition motifs in SR proteins, Proc Natl Acad Sci U S A., Apr. 15, 1997;94(8):3596-601.

Chauhan, S., et al., Fan beam dual energy X-ray absorptiometry body composition measurements in piglets, J Am Coll Nutr., Oct. 2003;22(5):408-14.

Chevalier, R. L., et al., Renal tubulointerstitial injury from ureteral obstruction in the neonatal rat is attenuated by IGF-1, Kidney Int., Mar. 2000;57(3):882-90.

Chung, C. S., et al., Stimulation of swine growth by porcine growth hormone, J Anim Sci., Jan. 1985;60(1):118-30.

Clark, R. G., et al., Growth hormone (GH) secretion in the conscious rat: negative feedback of GH on its own release, J Endocrinol., Nov. 1988;119(2):201-9.

Clark, R. G., et al., Growth induced by pulsatile infusion of an amidated fragment of human growth hormone releasing factor in normal and GHRF-deficient rats, Nature, Mar. 21-27, 1985;314(6008):281-3.

Cocea, L., Duplication of a region in the multiple cloning site of a plasmid vector to enhance cloning-mediated addition of restriction sites to a DNA fragment, Biotechniques, Nov. 1997;23(5):814-6.

Colao, A., et al., Impaired cardiac performance in elderly patients with growth hormone deficiency, J Clin Endocrinol Metab., Nov. 1999;84(11):3950-5.

Colao, et al., Beginning to end: Cardiovascular implications of growth hormone (GH) deficiency and GH therapy, Growth Hormone & IGF Research, Jul. 2006;16(1):41-48.

Cummings, D. E., et al., Age-related changes in growth hormone secretion: should the somatopause be treated?, Semin Reprod Endocrinol., 1999;17(4):311-25.

Dahl, G. E., et al., Comparison of somatotropin and growth hormone-releasing factor on milk yield, serum hormones, and energy status, J Dairy Sci., Oct. 1991;74(10):3421-8.

Dai, B., et al., Identification of a novel cis element required for cell density-dependent down-regulation of insulin-like growth factor-2 P3 promoter activity in Caco2 cells, J Biol Chem., Mar. 9, 2001;276(10):6937-44.

Danko, I., et al., Direct gene transfer into muscle, Vaccine, Dec. 1994;12(16):1499-502.

Darquet, A. M., et al., A new DNA vehicle for nonviral gene delivery: supercoiled minicircle, Gene Ther., Dec. 1997;4(12):1341-9.

Darquet, A. M., et al., Minicircle: an improved DNA molecule for in vitro and in vivo gene transfer, Gene Ther., Feb. 1999;6(2):209-18.

Davis, H. L., et al., Direct gene transfer into skeletal muscle in vivo: factors affecting efficiency of transfer and stability of expression, Hum Gene Ther., Apr. 1993;4(2):151-9.

Dolnik, V., et al., Electromigration behavior of poly-(L-glutamate) conformers in concentrated polyacrylamide gels, Biopolymers., Aug. 1993;33(8):1299-306.

Dornonville De La, Cour, C., et al., Ghrelin treatment reverses the reduction in weight gain and body fat in gastrectomised mice, Gut., Jul. 2005;54(7):907-13.

Dorsch-Hasler, K., et al., A long and complex enhancer activates transcription of the gene coding for the highly abundant immediate early mRNA in murine cytomegalovirus, Proc Natl Acad Sci U S A. Dec. 1985;82(24):8325-9.

Draghia-Akli, R., et al., Effects of plasmid-mediated growth hormone releasing hormone supplementation in young, healthy Beagle dogs, J Anim Sci., Sep. 2003;81(9):2301-10.

Draghia-Akli, R., et al., High-efficiency growth hormone-releasing hormone plasmid vector administration into skeletal muscle mediated by electroporation in pigs, FASEB J. Mar. 2003;17(3):526-8.

Draghia-Akli, R., et al., A new plasmid-mediated approach to supplement somatotropin production in pigs, J Anim Sci., 2004;82 E-Suppl:E264-269.

Draghia-Akli, R., et al., Myogenic expression of an injectable protease-resistant growth hormone-releasing hormone augments long-term growth in pigs, Nat Biotechnol., Dec. 1999;17(12):1179-83.

Draghia-Akli, R., et al., Effects of plasmid-mediated growth hormone-releasing hormone in severely debilitated dogs with cancer, Mol Ther, Dec. 2002;6(6):830-6.

Draghia-Akli, R., et al., Electrical enhancement of formulated plasmid delivery in animals, Technol Cancer Res Treat., Oct. 2002;1(5):365-72.

Draghia-Akli, R., et al., Enhanced growth by ectopic expression of growth hormone releasing hormone using an injectable myogenic vector, Nat Biotechnol., Nov. 1997;15(12):1285-9.

Draghia-Akli, R., et al., Enhanced animal growth via ligand-regulated GHRH myogenic-injectable vectors, FASEB J. Mar. 2002;16(3):426-8. Epub Jan. 14, 2002.

Dubreuil, P., et al., Effect of dose and frequency of administration of a potent analog of human growth hormone-releasing factor on hormone secretion and growth in pigs, J Anim Sci., May 1990;68(5):1254-68.

Duck, S. C., et al., Long-term treatment with GHRH [1-44] amide in prepubertal children with classical growth hormone deficiency, J Pediatr Endocrinol Metab., Jul.-Aug. 1999;12(4):531-6.

Duck, S., C., et al., Subcutaneous growth hormone-releasing hormone therapy in growth hormone-deficient children: first year of therapy, J Clin Endocrinol Metab., Oct. 1992;75(4):1115-20.

Ehlers, M., R., Recombinant human GHRH(1-44)NH2: clinical utility and therapeutic development program, Endocrine., Feb. 2001;14(1):137-41.

El-Aneed, A., An overview of current delivery systems in cancer gene therapy, J Control Release., Jan. 8, 2004;94(1):1-14.

Esch, F. S., et al., Characterization of a 40 residue peptide from a human pancreatic tumor with growth hormone releasing activity, Biochem Biophys Res Commun., Nov. 16, 1982;109(1):152-8.

Etherton, T. D., et al., Stimulation of pig growth performance by porcine growth hormone: determination of the dose-response relationship, J Anim Sci., Feb. 1987;64(2):433-43.

Evans, W. S., et al, Effects of intravenous, subcutaneous, and intranasal administration of growth hormone (GH)-releasing hormone-40 on serum GH concentrations in normal men, J Clin Endocrinol Metab., Nov. 6, 1985;61(5):846-50.

Fewell, J. G., et al., Gene therapy for the treatment of hemophilia B using PINC-formulated plasmid delivered to muscle with electroporation, Mol Ther., Apr. 2001;3(4):574-83.

Frederickson, R. M., et al., Nonclinical toxicology in support of licensure of gene therapies. Arlington, VA, USA, Mar. 13-14, 2003, Mol Ther., Jul. 2003;8(1):8-10.

Fryer, A. D., et al., Effect of inflammatory cell mediators on M2 muscarinic receptors in the lungs, Life Sci., 1993;52(5-6):529-36.

Fujikawa, K., et al., Subcutaneously administered prolactin and 20K hGH, but not rGH or 22K hGH, prevent restraint stress-induced gastric ulcers in rats, Endocr J., Mar. 2000;47 Suppl:S49-52.

Gehl, J., et al., Enhancement of cytotoxicity by electropermeabilization: an improved method for screening drugs, Anticancer Drugs., Apr. 1998;9(4):319-25.

Gehl, J., et al.,In vivo electroporation of skeletal muscle: threshold, efficacy and relation to electric field distribution, Biochim Biophys Acta., Aug. 5, 1999;1428(2-3):233-40.

German, M., et al., The insulin gene promoter. A simplified nomenclature, Diabetes, Aug. 1995;44(8):1002-4.

Ghigo, E., et al., Endocrine and non-endocrine activities of growth hormone secretagogues in humans, Horm Res., 1999;51 Suppl 3:9-15.

Gopinath, R., et al., Effects of porcine growth hormone on glucose metabolism of pigs: I. Acute and chronic effects on plasma glucose and insulin status, J Anim Sci., Mar. 1989;67(3):682-8.

Gopinath, R., et al., Effects of porcine growth hormone on glucose metabolism of pigs: II. Glucose tolerance, peripheral tissue insulin sensitivity and glucose kinetics, J Anim Sci., Mar. 1989;67(3):689-97.

Guillemin, R., et al., Growth hormone-releasing factor from a human pancreatic tumor that caused acromegaly, Science, Nov. 5, 1982;218(4572):585-7.

Heller, R., et al., Phase I/II trial for the treatment of cutaneous and subcutaneous tumors using electrochemotherapy, Cancer, Mar. 1, 1996;77(5):964-71.

Horlick, R. A.,et al., The upstream muscle-specific enhancer of the rat muscle creatine kinase gene is composed of multiple elements, Mol Cell Biol., Jun. 1989;9(6):2396-413.

Inouye, C., et al., Isolation of a cDNA encoding a metal response element binding protein using a novel expression cloning procedure: the one hybrid system, DNA Cell Biol., Jul. 1994;13(7):731-42.

Inouye, C., et al., Determination of the transcription initiation site and identification of the protein product of the regulatory gene xylR for xyl operons on the TOL plasmid, J Bacteriol., Sep. 1985;163(3):863-9.

Jaynes, J. B., et al., The muscle creatine kinase gene is regulated by multiple upstream elements, including a muscle-specific enhancer, Mol Cell Biol., Jan. 1988;8(1):62-70.

Kawamoto, T., et al., Identification of the human beta-actin enhancer and its binding factor, Mol Cell Biol., Jan. 1988;8(1):267-72.

Kawamoto, T., et al., DNA bending and binding factors of the human beta-actin promoter, Nucleic Acids Res., Jan. 25, 1989;17(2):523-37.

Khan, A. S., et al., Highly efficient constant-current electroporation increases in vivo plasmid expression, DNA Cell Biol., Dec. 2005;24(12):810-8.

Khan, A. S., et al., Optimization of electroporation parameters for the intramuscular delivery of plasmids in pigs, DNA Cell Biol., Dec. 2003;22(12):807-14.

Klamut, H. J., et al., Identification of a transcriptional enhancer within muscle intron 1 of the human dystrophin gene, Hum Mol Genet., Oct. 1996;5(10):1599-606.

Klamut, H. J., et al., Molecular and functional analysis of the muscle-specific promoter region of the Duchenne muscular dystrophy gene, Mol Cell Biol., Jan. 1990;10(1):193-205.

Kotler, D. P., Cachexia, Ann Intern Med., Oct. 17, 2000;133(8):622-34.

Kraus, J., et al., Alternative promoter usage and tissue specific expression of the mouse somatostatin receptor 2 gene, FEBS Lett., May 29, 1998;428(3):165-70.

Langenberg, C., et al, Ghrelin and the metabolic syndrome in older adults, J Clin Endocrinol Metab., Dec. 2005;90(12):6448-53.

Lareyre, J. J., et al., A 5-kilobase pair promoter fragment of the murine epididymal retinoic acid-binding protein gene drives the tissue-specific, cell-specific, and androgen-regulated expression of a foreign gene in the epididymis of transgenic mice, J Biol Chem., Mar. 19, 1999;274(12):8282-90.

Larsen, P. R., et al., Sequences required for cell-type specific thyroid hormone regulation of rat growth hormone promoter activity, J Biol Chem., Nov. 5, 1986;261(31):14373-6.

Lee, S. H., et a., Tissue-specific promoter usage in the D1A dopamine receptor gene in brain and kidney, DNA Cell Biol., Nov. 1997;16(11):1267-75.

Lesbordes, J. C., et al., In vivo electrotransfer of the cardiotrophin-1 gene into skeletal muscle slows down progression of motor neuron degeneration in pmn mice, Hum Mol Genet., Jul. 1, 2002;11(14):1615-25.

Levenson, V. V., et al., Internal ribosomal entry site-containing retroviral vectors with green fluorescent protein and drug resistance markers, Hum Gene Ther., May 20, 1998;9(8):1233-6.

Li, C., et al., Tumor irradiation enhances the tumor-specific distribution of poly(L-glutamic acid)-conjugated paclitaxel and its antitumor efficacy, Clin Cancer Res., Jul. 2000;6(7):2829-34.

Li, X. et al., Synthetic muscle promoters: activities exceeding naturally occurring regulatory sequences, Nat Biotechnol., Mar. 1999;17(3):241-5.

Lin, H., et al., Muscle-specific expression of the troponin I gene requires interactions between helix-loop-helix muscle regulatory factors and ubiquitous transcription factors, Mol Cell Biol., Jan. 1991;11(1):267-80.

Lissett, C. A., et al., Effects of growth hormone on bone and muscle, Growth Horm IGF Res., Apr. 2000;10 Suppl B: S95-101.

Liu, Y., et al., Identification of an enhancer sequence within the first intron required for cartilage-specific transcription of the alpha2(XI) collagen gene, J Biol Chem., Apr. 28, 2000;275(17):12712-8.

Lucas, M. L, et al., IL-12 plasmid delivery by in vivo electroporation for the successful treatment of established subcutaneous B16.F10 melanoma, Mol Ther., Jun. 2002;5(6):668-75.

Lucas, M., L., et al., In vivo electroporation using an exponentially enhanced pulse: a new waveform, DNA Cell Biol. Mar. 2001;20(3):183-8.

Macejak, D. G., et al., Internal initiation of translation mediated by the 5' leader of a cellular mRNA, Nature, Sep. 5, 1991;353(6339):90-4.

Matsubara, H., et al., Electroporation-mediated transfer of cytokine genes into human esophageal tumors produces anti-tumor effects in mice, Anticancer Res., Jul.-Aug. 2001;21(4A):2501-3.

Miklavcic, D., et al., The importance of electric field distribution for effective in vivo electroporation of tissues, Biophys J., May 1998;74(5):2152-8.

Mulligan, K., et al., Anabolic treatment with GH, IGF-I, or anabolic steroids in patients with HIV-associated wasting, Int J Cardiol., Sep. 2002;85(1):151-9.

Mumper, R. J., et al., Protective interactive noncondensing (PINC) polymers for enhanced plasmid distribution and expression in rat skeletal muscle, J Control Release., Mar. 2, 1998;52(1-2):191-203.

Muramatsu, T., et al., In vivo gene electroporation in skeletal muscle with special reference to the duration of gene expression, Int J Mol Med., Jan. 2001;7(1):37-42.

Nagaya, N., et al., Treatment of cachexia with ghrelin in patients with COPD, Chest, Sep. 2005;128(3):1187-93.

Narum, D., et al., Codon optimization of gene fragments encoding Plasmodium falciparum merzoite proteins enhances DNA vaccine protein expression and immunogenicity in mice, Infect Immun., Dec. 2001;69(12):7250-3.

Nomoto, S., et al., Cloning and characterization of the alternative promoter regions of the human LIMK2 gene responsible for alternative transcripts with tissue-specific expression, Gene, Aug. 20, 1999;236(2):259-71.

Ohlsson, H., et al., Novel insulin promoter- and enhancer-binding proteins that discriminate between pancreatic alpha- and beta-cells, Mol Endocrinol., Jul. 1991;5(7):897-904.

Otani, Y., et al., Rapidly curable biological glue composed of gelatin and poly(L-glutamic acid), Biomaterials., Jul. 1996;17(14):1387-91.

Otani, Y., et al., Hemostatic capability of rapidly curable glues from gelatin, poly(L-glutamic acid), and carbodiimide, Biomaterials., Nov. 1998;19(22):2091-8.

Needleman, S. B., et al., A general method applicable to the search for similarities in the amino acid sequence of two proteins, J Mol Biol., Mar. 1970;48(3):443-53.

Pearson, W. R., et al., Improved tools for biological sequence comparison, Proc Natl Acad Sci U S A., Apr. 1988;85(8):2444-8.

Higgins, D. G., et al., Clustal: a package for performing multiple sequence alignment on a microcomputer, Gene, Dec. 15, 1988;73(1):237-44.

Higgins, D. G., et al., Fast and sensitive multiple sequence alignments on a microcomputer, Comput Appl Biosci., Apr. 1989;5(2):151-3.

Corpet, F., Multiple sequence alignment with hierarchical clustering, Nucleic Acids Res., Nov. 25, 1988;16 (22):10881-90.

Huang, X., et al., Parallelization of a local similarity algorithm, Comput Appl Biosci., Apr. 1992;8(2):155-65.

Pearson, W. R., Using the FASTA program to search protein and DNA sequence databases, Methods Mol Biol., 1994;24:307-31.

Patil, S. D., et al., DNA-based therapeutics and DNA delivery systems: a comprehensive review, AAPS J., Apr.8, 2005 8;7(1):E61-77.

Pech, M., et al., Functional identification of regulatory elements within the promoter region of platelet-derived growth factor 2, Mol Cell Biol., Feb. 1989;9(2):396-405.

Pelletier, J., et al., Internal initiation of translation of eukaryotic mRNA directed by a sequence derived from poliovirus RNA, Nature, Jul. 28, 1988;334(6180):320-5.

Phung, L. T., et al., The effects of growth hormone-releasing peptide-2 (GHRP-2) on the release of growth hormone and growth performance in swine, Domest Anim Endocrinol., Apr. 2000;18(3):279-91.

Pinkert, C. A., et al., An albumin enhancer located 10 kb upstream functions along with its promoter to direct efficient, liver-specific expression in transgenic mice, Genes Dev., May 1987;1(3):268-76.

Pommier, S. A., et al., Effect of a potent analog of human growth hormone-releasing factor on carcass composition and quality of crossbred market pigs, J Anim Sci., May 1990;68(5):1291-8.

Potter, H., et al., Enhancer-dependent expression of human kappa immunoglobulin genes introduced into mouse pre-B lymphocytes by electroporation, Proc Natl Acad Sci U S A., Nov. 1984;81(22):7161-5.

Prentice, H., et al., Tissue restricted gene expression assayed by direct DNA injection into cardiac and skeletal muscle, J Mol Cell Cardiol., Oct. 1994;26(10):1393-401.

Prud'Homme, G. J., et al., Electroporation-enhanced nonviral gene transfer for the prevention or treatment of immunological, endocrine and neoplastic diseases, Curr Gene Ther., Apr. 2006;6(2):243-73.

Rahim, A., et al., Does desensitization to hexarelin occur?, Growth Horm IGF Res., Apr. 1998;8 Suppl B:141-3.

Satozawa, N., et al., Differences in the effects of 20 K- and 22 K-hGH on water retention in rats, Growth Horm IGF Res., Aug. 2000;10(4):187-92.

Schleim, K. D., et al., Increases in circulating insulin-like growth factor I levels by the oral growth hormone secretagogue MK-0677 in the beagle are dependent upon pituitary mediation, Endocrinology, Apr. 1999;140(4):1552-8.

Siejka, A., et al., Effect of growth hormone-releasing hormone (GHRH) and GHRH antagonist (MZ-4-71) on interferon-gamma secretion from human peripheral blood mononuclear cells in vitro, Neuropeptides, Feb. 2004;38 (1):35-9.

Skroch, P., et al., Regulation of human and yeast metallothionein gene transcription by heavy metal ions, Prog Clin Biol Res., 1993;380:113-28.

Soubrier, F., et al., pCOR: a new design of plasmid vectors for nonviral gene therapy, Gene Ther. Aug. 1999;6 (8):1482-8.

Sun, Y., et al., Ghrelin stimulation of growth hormone release and appetite is mediated through the growth hormone secretagogue receptor, Proc Natl Acad Sci U S A. Mar. 30, 2004;101(13):4679-84.

Svensson, J. A., et al., Clinical and experimental effects of growth hormone secretagogues on various organ systems, Horm Res., 1999;51 Suppl 3:16-20.

Terada, Y., et al., Efficient and ligand-dependent regulated erythropoietin production by naked dna injection and in vivo electroporation, Am J Kidney Dis., Oct. 2001;38(4 Suppl 1):S50-3.

Thorner, M. O., et al., Extrahypothalamic growth-hormone-releasing factor (GRF) secretion is a rare cause of acromegaly: plasma GRF levels in 177 acromegalic patients, J Clin Endocrinol Metab., Nov. 1984;59(5):846-9.

Thorner, M. O., et al., Physiological and clinical studies of GRF and GH, Recent Prog Horm Res., 1986;42:589-640.

Thorner, M. O., et al., Clinical studies with GHRH in man, Horm Res., 1986;24(2-3):91-8.

Tollefsen, S., et al, DNA injection in combination with electroporation: a novel method for vaccination of farmed ruminants, Scand J Immunol., Mar. 2003;57(3):229-38.

Tone, C. M., et al., Long-term effects of plasmid-mediated growth hormone releasing hormone in dogs, Cancer Gene Ther., May 2004;11(5):389-96.

Tripathy, S. K., et al., Long-term expression of erythropoietin in the systemic circulation of mice after intramuscular injection of a plasmid DNA vector, Proc Natl Acad Sci U S A., Oct. 1, 1996;93(20):10876-80.

Tronche, F., et al., The rat albumin promoter: cooperation with upstream elements is required when binding of APF/HNF1 to the proximal element is partially impaired by mutation or bacterial methylation, Mol Cell Biol., Nov. 1989;9 (11):4759-66.

Trudel, M., et al., A 3' enhancer contributes to the stage-specific expression of the human beta-globin gene, Genes Dev., Nov. 1987;1(9):954-61.

Tsumaki, N., et al., Modular arrangement of cartilage- and neural tissue-specific cis-elements in the mouse alpha2 (XI) collagen promoter, J Biol Chem., Sep. 4, 1998;273(36):22861-4.

Tsunekawa, B., et al, The 20-kilodalton (kDa) human growth hormone (hGH) differs from the 22-kDa hGH in the effect on the human prolactin receptor, Endocrinology, Sep. 1999;140(9):3909-18.

Tronche, F., et al., Anatomy of the rat albumin promoter, Mol Biol Med., Apr. 1990;7(2):173-85.

Tsurumi, Y., et al., Direct intramuscular gene transfer of naked DNA encoding vascular endothelial growth factor augments collateral development and tissue perfusion, Circulation, Dec. 15, 1996;94(12):3281-90.

Tur-Kaspa, R., et al., Use of electroporation to introduce biologically active foreign genes into primary rat hepatocytes, Mol Cell Biol., Feb. 1986;6(2):716-8.

Vance, M. L., et al., Pulsatile growth hormone secretion in normal man during a continuous 24-hour infusion of human growth hormone releasing factor (1-40). Evidence for intermittent somatostatin secretion, J Clin Invest., May 1985;75(5):1584-90.

Vance, M. L., et al., Lack of in vivo somatotroph desensitization or depletion after 14 days of continuous growth hormone (GH)-releasing hormone administration in normal men and a GH-deficient boy, J Clin Endocrinol Metab., Jan. 1989;68(1):22-8.

Verhelst, J., et al., Two years of replacement therapy in adults with growth hormone deficiency, Clin Endocrinol (Oxf)., Oct. 1997;47(4):485-94.

Vilquin, J. T., et al, Electrotransfer of naked DNA in the skeletal muscles of animal models of muscular dystrophies, Gene Ther., Jul. 2001;8(14):1097-107.

Vittone, J., et al, Effects of single nightly injections of growth hormone-releasing hormone (GHRH 1-29) in healthy elderly men, Metabolism, Jan. 1997;46(1):89-96.

Wada, M., et al., The 20-kilodalton (kDa) human growth hormone (hGH) differs from the 22-kDa hGH in the complex formation with cell surface hGH receptor and hGH-binding protein circulating in human plasma, Mol Endocrinol., Jan. 1998;12(1):146-56.

Walker, R. F., et al., Effects of stimulated growth hormone secretion on age-related changes in plasma cholesterol and hepatic low density lipoprotein messenger RNA concentrations, Mech Ageing Dev., Sep. 1994;75(3):215-26.

Wallace, J. D., et al., Changes in non-22-kilodalton (kDa) isoforms of growth hormone (GH) after administration of 22-kDa recombinant human Gh in trained adult males, J Clin Endocrinol Metab., Apr. 2001;86(4):1731-7.

Wells, D. J., Gene therapy progress and prospects: electroporation and other physical methods, Gene Ther., Sep. 2004;11(18):1363-9.

Wells, K. E., et al., Immune responses, not promoter inactivation, are responsible for decreased long-term expression following plasmid gene transfer into skeletal muscle, FEBS Lett. Apr. 28, 1997;407(2):164-8.

Wolff, J. A., et al., Direct gene transfer into mouse muscle in vivo, Science, Mar. 23, 1990;247(4949 Pt 1):1465-8.

Wu, H. K., et al., Promoter-dependent tissue-specific expressive nature of imprinting gene, insulin-like growth factor II, in human tissues, Biochem Biophys Res Commun., Apr. 7, 1997;233(1):221-6.

Yasui, A., et al., Elevated gastrin secretion by in vivo gene electroporation in skeletal muscle, Int J Mol Med. Nov. 2001;8(5):489-94.

Yutzey, K. E., et al., Different E-box regulatory sequences are functionally distinct when placed within the context of the troponin I enhancer, Nucleic Acids Res., Oct. 11, 1992;20(19):5105-13.

Zachwieja, J. J., et al., Does growth hormone therapy in conjunction with resistance exercise increase muscle force production and muscle mass in men and women aged 60 years or older?, Phys Ther., Jan. 1999;79(1):76-82.

Zampaglione, I., et al., In vivo DNA gene electro-transfer: a systematic analysis of different electrical parameters, J Gene Med., Nov. 2005;7(11):1475-81.

Zhao-Emonet, J. C., et al., Deletional and mutational analyses of the human CD4 gene promoter: characterization of a minimal tissue-specific promoter, Biochim Biophys Acta., Nov. 8, 1998;1442(2-3):109-19.

Meyers and Miller, Computer Applic. Biol. Sci., 1988;4:11-17.

Smith and Waterman, Adv. Appl. Math, 1981;2:482.

* cited by examiner

| | Treatment | | |
|---|---|---|---|
| | Control | pWT-GHRH | GH |
| n | 9 | 20 | 8 |
| Body Weight (g/d) | 387 ± 10 [a] | 437 ± 6 [b] | 470 ± 20 [c] |
| Fat (g/d) | 60 ± 3 | 61 ± 1 | 55 ± 2 |
| (g/(kg BW.d)) | 152 ± 6.5 [a] | 142 ± 2.08 [a] | 118 ± 5 [b] |
| Lean (g/d) | 325 ± 7 [a] | 370 ± 7 [b] | 414 ± 20 [c] |
| Bone Mineral Content (g/d) | 6.2 ± 0.2 | 6.7 ± 0.1 | 6.3 ± 0.2 |

Figure 2

|  | Treatment | | |
| --- | --- | --- | --- |
|  | Control | pWT-GHRH | GH |
| n | 9 | 20 | 8 |
| Body Weight (kg) | 22.3 ± 0.5 [a] | 23.4 ± 0.3 [a] | 25.4 ± 0.7 [b] |
| Fat-free Mass (kg) | 19.4 ± 0.5 [a] | 21.3 ± 0.3 [b] | 23.4 ± 1.0 [c] |
| Fat (% BW) | 13.2 ± 1.3 [a] | 9.3 ± 1.0 [b] | 8.2 ± 1.7 [b] |
| Bone Mineral Content (g) | 367 ± 11 | 378 ± 5 | 366 ± 11 |
| (%BW) | 1.65 ± 0.03 [a] | 1.57 ± 0.02 [b] | 1.42 ± 0.03 [c] |
| Carcass (%BW) | 70.9 ± 0.6 [a] | 73.5 ± 0.3 [b] | 72.2 ± 0.7 [ab] |
| Medial backfat (cm/kg) | 0.67 ± 0.08 [a] | 0.46 ± 0.02 [b] | 0.56 ± 0.02 [c] |
| Distal backfat (cm/kg) | 0.57 ± 0.05 [a] | 0.33 ± 0.03 [b] | 0.41 ± 0.02 [c] |
| Total organs (%BW) | 14.2 ± 0.8 | 13.8 ± 0.5 | 13.3 ± 0.8 |
| Kidney (%BW) | 0.56 ± 0.02 [a] | 0.56 ± 0.01 [a] | 0.63 ± 0.01 [b] |

Figure 3

|  | days | Control | Treatment pWT-GHRH | pGH |
|---|---|---|---|---|
| n |  | 7-8 | 19-20 | 7-8 |
| IGF-I (ng/mL) | 0 (12)* | 11.0 ± 4.2 |  |  |
|  | 7 | 17.4 ± 7.0 | 13.0 ± 2.5 | 14.8 ± 3.8 |
|  | 28 | 56.6 ± 26.6$^a$ | 127.3 ± 77.5$^b$ | 182.2 ± 103.8$^b$ |
|  | 49 | 338.4 ± 115$^a$ | 312.6 ± 118$^a$ | 623.0 ± 105.2$^b$ |
| IGFBP-3 | 0 (17)* | 718 ± 127 |  |  |
|  | 7 | 869 ± 54 | 889 ± 152 | 898 ± 170 |
|  | 28 | 1335 ± 68 | 1353 ± 148 | 1371 ± 146 |
|  | 49 | 1521 ± 119 | 1467 ± 183 | 1508 ± 77 |

Figure 4

| | Total protein | BUN | Creatinine | Glucose | Cholesterol | Sodium | Chloride |
|---|---|---|---|---|---|---|---|
| Control | 5.23 ± 0.06[a] | 23.0 ± 14.7[a] | 0.93 ± 0.03 | 129 ± 4.9[a] | 87.0 ± 8.4 | 146 ± 0.0 | 104 ± 0.6 |
| GH | 5.55 ± 0.04[b] | 15.5 ± 0.41[b] | 0.85 ± 0.12 | 111 ± 8.5 | 99.0 ± 12[a] | 146 ± 0.8 | 104 ± 0.0 |
| pWT-GHRH | 4.91 ± 0.05[c] | 19.7 ± 1.04 | 0.87 ± 0.04 | 109 ± 3.8[b] | 76.3 ± 4.4[b] | 146 ± 0.9 | 103 ± 0.8 |

SEQUENCE LISTING

<160> NUMBER OF SEQ ID NOS: 35

<210> SEQ ID NO 1
<211> LENGTH: 39
<212> TYPE: PRT
<213> ORGANISM: Artificial Sequence
<220> FEATURE:
<223> OTHER INFORMATION: HV-growth hormone releasing hormone ("GHRH")
      analog.

<400> SEQUENCE: 1

Val Asp Ala Ile Phe Thr Asn Ser Tyr Arg Lys Val Leu Ala Gln Leu
1               5                   10                  15

Ser Ala Arg Lys Leu Leu Gln Asp Ile Leu Asn Arg Gln Gln Gly Glu
            20                  25                  30

Arg Asn Gln Glu Gln Gly Ala
        35

<210> SEQ ID NO 2
<211> LENGTH: 40
<212> TYPE: PRT
<213> ORGANISM: Artificial Sequence
<220> FEATURE:
<223> OTHER INFORMATION: pig-GHRH

<400> SEQUENCE: 2

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 3
<211> LENGTH: 40
<212> TYPE: PRT
<213> ORGANISM: Artificial Sequence
<220> FEATURE:
<223> OTHER INFORMATION: Bovine-GHRH

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: Artificial Sequence
<220> FEATURE:
<223> OTHER INFORMATION: Dog-GHRH

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Arg Glu Gln Gly Ala
        35                  40

<210> SEQ ID NO 5
<211> LENGTH: 40
<212> TYPE: PRT
<213> ORGANISM: Artificial Sequence
<220> FEATURE:
<223> OTHER INFORMATION: Cat-GHRH

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 6
<211> LENGTH: 40
<212> TYPE: PRT
<213> ORGANISM: Artificial Sequence
<220> FEATURE:
<223> OTHER INFORMATION: TI-growth hormone releasing hormone ("GHRH")
      analog.

<400> SEQUENCE: 6

Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 7
<211> LENGTH: 40
<212> TYPE: PRT
<213> ORGANISM: Artificial Sequence
<220> FEATURE:
<223> OTHER INFORMATION: Amino-acid sequence for ovine-GHRH

<400> SEQUENCE: 7

Tyr Ala Asp Ala Ile Phe Thr Asn Ser Tyr Arg Lys Ile Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 8
<211> LENGTH: 43
<212> TYPE: PRT
<213> ORGANISM: Artificial Sequence
<220> FEATURE:
<223> OTHER INFORMATION: Amino-acid sequnce for chicken-GHRH

<400> SEQUENCE: 8

His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys Arg Val Gly
            20                  25                  30

Ser Gly Leu Gly Asp Glu Ala Glu Pro Leu Ser
        35                  40

<210> SEQ ID NO 9

```
<211> LENGTH: 40
<212> TYPE: PRT
<213> ORGANISM: Artificial Sequence
<220> FEATURE:
<223> OTHER INFORMATION: Horse GHRH
<220> FEATURE:
<221> NAME/KEY: MISC_FEATURE
<222> LOCATION: (1)..(1)
<223> OTHER INFORMATION: "Xaa" can be any AA sequence
<220> FEATURE:
<221> NAME/KEY: MISC_FEATURE
<222> LOCATION: (30)..(40)
<223> OTHER INFORMATION: "Xaa" can be any AA sequence

<400> SEQUENCE: 9

Xaa Ala Asp Ala Ile Phe Thr Asn Asn Tyr Arg Lys Val Leu Gly Gln
 1               5                  10                  15

Leu Ser Ala Arg Lys Ile Leu Gln Asp Ile Met Ser Arg Xaa Xaa Xaa
            20                  25                  30

Xaa Xaa Xaa Xaa Xaa Xaa Xaa Xaa
        35                  40

<210> SEQ ID NO 10
<211> LENGTH: 40
<212> TYPE: PRT
<213> ORGANISM: Artificial Sequence
<220> FEATURE:
<223> OTHER INFORMATION: Human (1-40) GHRH

<400> SEQUENCE: 10

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala
        35                  40

<210> SEQ ID NO 11
<211> LENGTH: 40
<212> TYPE: PRT
<213> ORGANISM: Artificial Sequence
<220> FEATURE:
<223> OTHER INFORMATION: TV-growth hormone releasing hormone analog

<400> SEQUENCE: 11

Tyr Val Asp Ala Ile Phe Thr Asn Ser Tyr Arg Lys Val Leu Ala Gln
 1               5                  10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 12
<211> LENGTH: 40
<212> TYPE: PRT
<213> ORGANISM: Artificial Sequence
<220> FEATURE:
<223> OTHER INFORMATION: TA-growth hormone releasing hormone analog

<400> SEQUENCE: 12

Tyr Ala Asp Ala Ile Phe Thr Asn Ser Tyr Arg Lys Val Leu Ala Gln
 1               5                  10                  15

Leu Ser Ala Arg Lys Leu Leu Gln Asp Ile Leu Asn Arg Gln Gln Gly
            20                  25                  30

Glu Arg Asn Gln Glu Gln Gly Ala
```

-continued

```
                35                  40
```

<210> SEQ ID NO 13
<211> LENGTH: 44
<212> TYPE: PRT
<213> ORGANISM: Artificial Sequence
<220> FEATURE:
<223> OTHER INFORMATION: Human (1-44) growth hormone releasing hormone

<400> SEQUENCE: 13

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```

<210> SEQ ID NO 14
<211> LENGTH: 40
<212> TYPE: PRT
<213> ORGANISM: Artificial Sequence
<220> FEATURE:
<223> OTHER INFORMATION: GHRH (1-40) OH.
<220> FEATURE:
<221> NAME/KEY: MISC_FEATURE
<222> LOCATION: (1)..(1)
<223> OTHER INFORMATION: Xaa at postion 1 may be tyrosine, or histidine
<220> FEATURE:
<221> NAME/KEY: MISC_FEATURE
<222> LOCATION: (2)..(2)
<223> OTHER INFORMATION: Xaa at postion 2 may be alanine, valine, or
      isoleucine
<220> FEATURE:
<221> NAME/KEY: MISC_FEATURE
<222> LOCATION: (15)..(15)
<223> OTHER INFORMATION: Xaa at postion 15 may be alanine, valine, or
      isoleucine
<220> FEATURE:
<221> NAME/KEY: MISC_FEATURE
<222> LOCATION: (27)..(27)
<223> OTHER INFORMATION: Xaa at postion 27 may be methionine, or
      leucine
<220> FEATURE:
<221> NAME/KEY: MISC_FEATURE
<222> LOCATION: (28)..(28)
<223> OTHER INFORMATION: Xaa at postion 28 may be serine or asparagine
<220> FEATURE:
<221> NAME/KEY: MISC_FEATURE
<222> LOCATION: (34)..(34)
<223> OTHER INFORMATION: Xaa at postion 34 may be arginine or serine
<220> FEATURE:
<221> NAME/KEY: MISC_FEATURE
<222> LOCATION: (36)..(36)
<223> OTHER INFORMATION: Xaa at postion 36 may be arginine or glutamine
<220> FEATURE:
<221> NAME/KEY: MISC_FEATURE
<222> LOCATION: (38)..(38)
<223> OTHER INFORMATION: Xaa at postion 38 may be arginine or glutamine

<400> SEQUENCE: 14

```
Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Xaa Asn Xaa Glu Xaa Gly Ala
        35                  40
```

<210> SEQ ID NO 15
<211> LENGTH: 323
<212> TYPE: DNA
<213> ORGANISM: Artificial Sequence

```
<220> FEATURE:
<223> OTHER INFORMATION: Nucleic acid sequence of a eukaryotic promoter
      c5-12

<400> SEQUENCE: 15
cggccgtccg ccctcggcac catcctcacg acacccaaat atggcgacgg gtgaggaatg    60
gtggggagtt atttttagag cggtgaggaa ggtgggcagg cagcaggtgt tggcgctcta   120
aaaataactc ccgggagtta tttttagagc ggaggaatgg tggacaccca aatatggcga   180
cggttcctca cccgtcgcca tatttgggtg tccgccctcg gccggggccg cattcctggg   240
ggccgggcgg tgctcccgcc cgcctcgata aaaggctccg gggccggcgg cggcccacga   300
gctacccgga ggagcgggag gcg                                           323

<210> SEQ ID NO 16
<211> LENGTH: 190
<212> TYPE: DNA
<213> ORGANISM: Artificial Sequence
<220> FEATURE:
<223> OTHER INFORMATION: Nucleic acid sequence of a human growth
      hormone poly A tail

<400> SEQUENCE: 16
gggtggcatc cctgtgaccc ctccccagtg cctctcctgg ccctggaagt tgccactcca    60
gtgcccacca gccttgtcct aataaaatta agttgcatca ttttgtctga ctaggtgtcc   120
ttctataata ttatggggtg gagggggggtg gtatggagca aggggcaagt tgggaagaca   180
acctgtaggg                                                          190

<210> SEQ ID NO 17
<211> LENGTH: 795
<212> TYPE: DNA
<213> ORGANISM: Artificial Sequence
<220> FEATURE:
<223> OTHER INFORMATION: Nucleic acid squence for the antibiotic
      resistance gene kanamycin

<400> SEQUENCE: 17
atgattgaac aagatggatt gcacgcaggt tctccggccg cttgggtgga gaggctattc    60
ggctatgact gggcacaaca gacaatcggc tgctctgatg ccgccgtgtt ccggctgtca   120 gcgcagggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac tcatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795

<210> SEQ ID NO 18
<211> LENGTH: 55
<212> TYPE: DNA
```

```
<213> ORGANISM: Artificial Sequence
<220> FEATURE:
<223> OTHER INFORMATION: Nucleic acid sequence of human growth hormone
      5'untranslated region

<400> SEQUENCE: 18
caaggcccaa ctccccgaac cactcagggt cctgtggaca gctcacctag ctgcc            55

<210> SEQ ID NO 19
<211> LENGTH: 782
<212> TYPE: DNA
<213> ORGANISM: Artificial Sequence
<220> FEATURE:
<223> OTHER INFORMATION: Nucleic acid sequence of a plasmid pUC-18
      origin of replication

<400> SEQUENCE: 19
tcttccgctt cctcgctcac tgactcgctg cgctcggtcg ttcggctgcg gcgagcggta      60
tcagctcact caaaggcggt aatacggtta tccacagaat caggggataa cgcaggaaag     120
aacatgtgag caaaaggcca gcaaaaggcc aggaaccgta aaaaggccgc gttgctggcg     180 ttttccata ggctccgccc ccctgacgag catcacaaaa atcgacgctc aagtcagagg      240
tggcgaaacc cgacaggact ataaagatac caggcgtttc ccctggaag ctccctcgtg      300 cgctctcctg ttccgaccct gccgcttacc ggatacctgt ccgcctttct cccttcggga     360
agcgtggcgc tttctcatag ctcacgctgt aggtatctca gttcggtgta ggtcgttcgc     420
tccaagctgg gctgtgtgca cgaaccccc gttcagcccg accgctgcgc cttatccggt      480
aactatcgtc ttgagtccaa cccggtaaga cacgacttat cgccactggc agcagccact     540
ggtaacagga ttagcagagc gaggtatgta ggcggtgcta cagagttctt gaagtggtgg     600
cctaactacg gctacactag aaggacagta tttggtatct gcgctctgct gaagccagtt     660
accttcggaa aaagagttgg tagctcttga tccggcaaac aaaccaccgc tggtagcggt     720
ggtttttttg tttgcaagca gcagattacg cgcagaaaaa aaggatctca agaagatcct     780
tt                                                                    782

<210> SEQ ID NO 20
<211> LENGTH: 29
<212> TYPE: DNA
<213> ORGANISM: Artificial Sequence
<220> FEATURE:
<223> OTHER INFORMATION: Nucleic acid sequence of a prokaryotic PNEO
      promoter

<400> SEQUENCE: 20
accttaccag agggcgcccc agctggcaa                                        29

<210> SEQ ID NO 21
<211> LENGTH: 3534
<212> TYPE: DNA
<213> ORGANISM: Artificial Sequence
<220> FEATURE:
<223> OTHER INFORMATION: Plasmid vector having an analog HV-GHRH
      sequence

<400> SEQUENCE: 21
gttgtaaaac gacggccagt gaattgtaat acgactcact atagggcgaa ttggagctcc      60
accgcggtgg cggccgtccg ccctcggcac catcctcacg cacccaaat atggcgacgg      120 gtgaggaatg gtggggagtt attttttagag cggtgaggaa ggtgggcagg cagcaggtgt    180
tggcgctcta aaaataactc ccgggagtta ttttttagagc ggaggaatgg tggacaccca    240
```

```
aatatggcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcaccct cagcaacagc tcccactgct ccccacctcc    540 cccttt gacc ctcaggatgc ggcggcacgt agatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt    1020
tgggattcca ggcatgcatg accaggctca gctaattttt gtttttttgg tagagacggg    1080
gtttcaccat attggccagg ctggtctcca actcctaatc tcaggtgatc tacccacctt    1140
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga ggggggggccc ggtaccagct    1380 tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagacacg    2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
```

-continued

| | |
|---|---|
| agcggccatt ttccaccatg atattcggca agcaggcatc gccatgggtc acgacgagat | 2700 |
| cctcgccgtc gggcatgcgc gccttgagcc tggcgaacag ttcggctggc gcgagcccct | 2760 |
| gatgctcttc gtccagatca tcctgatcga caagaccggc ttccatccga gtacgtgctc | 2820 |
| gctcgatgcg atgtttcgct tggtggtcga atgggcaggt agccggatca agcgtatgca | 2880 |
| gccgccgcat tgcatcagcc atgatggata ctttctcggc aggagcaagg tgagatgaca | 2940 |
| ggagatcctg ccccggcact cgcccaata gcagccagtc ccttcccgct tcagtgacaa | 3000 |
| cgtcgagcac agctgcgcaa ggaacgcccg tcgtggccag ccacgatagc gcgctgcct | 3060 |
| cgtcctgcag ttcattcagg gcaccggaca ggtcggtctt gacaaaaaga accgggcgcc | 3120 |
| cctgcgctga cagccggaac acggcggcat cagagcagcc gattgtctgt tgtgcccagt | 3180 |
| catagccgaa tagcctctcc acccaagcgg ccggagaacc tgcgtgcaat ccatcttgtt | 3240 |
| caatcatgcg aaacgatcct catcctgtct cttgatcaga tcttgatccc ctgcgccatc | 3300 |
| agatccttgg cggcaagaaa gccatccagt ttactttgca gggcttccca accttaccag | 3360 |
| agggcgcccc agctggcaat tccggttcgc ttgctgtcca taaaaccgcc cagtctagca | 3420 |
| actgttggga agggcgatcg gtgcgggcct cttcgctatt acgccagctg gcgaaagggg | 3480 |
| gatgtgctgc aaggcgatta agttgggtaa cgccagggtt ttcccagtca cgac | 3534 |

<210> SEQ ID NO 22
<211> LENGTH: 2722
<212> TYPE: DNA
<213> ORGANISM: Artificial Sequence
<220> FEATURE:
<223> OTHER INFORMATION: Plasmid vector having a codon optimized mouse
      GHRH sequence

<400> SEQUENCE: 22

| | |
|---|---|
| ccaccgcggt ggcggccgtc cgccctcggc accatcctca cgacacccaa atatggcgac | 60 |
| gggtgaggaa tggtggggag ttatttttag agcggtgagg aaggtgggca ggcagcaggt | 120 |
| gttggcgctc taaaaataac tcccgggagt tattttttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |
| ggcggcccac gagctacccg gaggagcggg aggcgccaag cggatcccaa ggcccaactc | 360 |
| cccgaaccac tcagggtcct gtggacagct cactagctg ccatggtgct ctgggtgctc | 420 |
| tttgtgatcc tcatcctcac cagcggcagc cactgcagcc tgcctcccag ccctcccttc | 480 |
| aggatgcaga ggcacgtgga cgccatcttc accaccaact acaggaagct gctgagccag | 540 |
| ctgtacgcca ggaaggtgat ccaggacatc atgaacaagc agggcgagag gatccaggag | 600 |
| cagagggcca ggctgagctg ataagcttat cggggtggca tccctgtgac ccctccccag | 660 |
| tgcctctcct ggccctggaa gttgccactc cagtgcccac cagccttgtc ctaataaaat | 720 |
| taagttgcat cattttgtct gactaggtgt ccttctataa tattatgggg tggagggggg | 780 |
| tggtatggag caaggggcaa gttgggaaga acctgtag ggctcgaggg ggggccggt | 840 |
| accagctttt gttcccttta gtgagggtta atttcgagct tggtcttccg cttcctcgct | 900 |
| cactgactcg ctgcgctcgg tcgttcggct gcggcgagcg gtatcagctc actcaaaggc | 960 |
| ggtaatacgg ttatccacag aatcagggga taacgcagga agaacatgt gagcaaaagg | 1020 |
| ccagcaaaag gccaggaacc gtaaaaaggc cgcgttgctg gcgtttttcc ataggctccg | 1080 |
| ccccctgac gagcatcaca aaaatcgacg ctcaagtcag aggtggcgaa acccgacagg | 1140 |
| actataaaga taccaggcgt ttccccctgg aagctccctc gtgcgctctc ctgttccgac | 1200 |

```
cctgccgctt accggatacc tgtccgcctt tctcccttcg ggaagcgtgg cgctttctca   1260
tagctcacgc tgtaggtatc tcagttcggt gtaggtcgtt cgctccaagc tgggctgtgt   1320
gcacgaaccc cccgttcagc ccgaccgctg cgccttatcc ggtaactatc gtcttgagtc   1380
caacccggta agacacgact tatcgccact ggcagcagcc actggtaaca ggattagcag   1440
agcgaggtat gtaggcggtg ctacagagtt cttgaagtgg tggcctaact acggctacac   1500
tagaagaaca gtatttggta tctgcgctct gctgaagcca gttaccttcg gaaaaagagt   1560
tggtagctct tgatccggca aacaaaccac cgctggtagc ggtggttttt ttgtttgcaa   1620
gcagcagatt acgcgcagaa aaaaggatc tcaagaagat cctttgatct tttctacggg   1680
gtctgacgct cagctagcgc tcagaagaac tcgtcaagaa ggcgatagaa ggcgatgcgc   1740
tgcgaatcgg gagcggcgat accgtaaagc acgaggaagc ggtcagccca ttcgccgcca   1800
agctcttcag caatatcacg ggtagccaac gctatgtcct gatagcggtc cgccacaccc   1860
agccggccac agtcgatgaa tccagaaaag cggccatttt ccaccatgat attcggcaag   1920
caggcatcgc catgagtcac gacgagatcc tcgccgtcgg gcatgcgcgc cttgagcctg   1980
gcgaacagtt cggctggcgc gagccctga tgctcttcgt ccagatcatc ctgatcgaca   2040
agaccggctt ccatccgagt acgtgctcgc tcgatgcgat gtttcgcttg gtggtcgaat   2100
gggcaggtag ccggatcaag cgtatgcagc cgccgcattg catcagccat gatggatact   2160
ttctcggcag gagcaaggtg agatgacagg agatcctgcc ccggcacttc gcccaatagc   2220
agccagtccc ttcccgcttc agtgacaacg tcgagcacag ctgcgcaagg aacgcccgtc   2280
gtggccagcc acgatagccg cgctgcctcg tcctgcagtt cattcagggc accggacagg   2340
tcggtcttga caaaaagaac cgggcgcccc tgcgctgaca gccggaacac ggcggcatca   2400
gagcagccga ttgtctgttg tgcccagtca tagccgaata gcctctccac ccaagcggcc   2460
ggagaacctg cgtgcaatcc atcttgttca atcatgcgaa acgatcctca tcctgtctct   2520
tgatcagatc ttgatccct gcgccatcag atccttggcg gcaagaaagc catccagttt   2580
actttgcagg gcttcccaac cttaccagag ggcgccccag ctggcaattc cggttcgctt   2640
gctgtccata aaaccgccca gtctagcaac tgttgggaag ggcgatcgtg taatacgact   2700
cactataggg cgaattggag ct                                            2722
```

<210> SEQ ID NO 23
<211> LENGTH: 2725
<212> TYPE: DNA
<213> ORGANISM: Artificial Sequence
<220> FEATURE:
<223> OTHER INFORMATION: Plasmid vector having a codon optimized rat
      GHRH sequence

<400> SEQUENCE: 23

```
ccaccgcggt ggcggccgtc cgccctcggc accatcctca cgacacccaa atatggcgac     60
gggtgaggaa tggtggggag ttattttttag agcggtgagg aaggtgggca ggcagcaggt   120
gttggcgctc taaaaataac tcccgggagt tattttttaga gcgaggaat ggtgacacc    180 caaatatggc gacggttcct caccccgtcgc catatttggg tgtccgccct cggccggggc   240
cgcattcctg ggggccgggc ggtgctcccg cccgcctcga taaaaggctc cggggccggc   300
ggcggcccac gagctacccg gaggagcggg aggcgccaag cggatcccaa gcccaactc   360 cccgaaccac tcagggtcct gtggacagct cacctagctg ccatggccct gtgggtgttc   420
ttcgtgctgc tgaccctgac cagcggaagc cactgcagcc tgcctcccag ccctcccttc   480
```

```
agggtgcgcc ggcacgccga cgccatcttc accagcagct acaggaggat cctgggccag    540
ctgtacgcta ggaagctcct gcacgagatc atgaacaggc agcagggcga gaggaaccag    600
gagcagagga gcaggttcaa ctgataagct tatcggggtg catccctgt gacccctccc     660 cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga gggggggccc    840
ggtaccagct tttgttccct ttagtgaggg ttaatttcga gcttggtctt ccgcttcctc    900
gctcactgac tcgctgcgct cggtcgttcg gctgcggcga cggtatcag ctcactcaaa     960 ggcggtaata cggttatcca cagaatcagg ggataacgca ggaaagaaca tgtgagcaaa   1020
aggccagcaa aaggccagga accgtaaaaa ggccgcgttg ctggcgtttt tccataggct   1080 ccgccccct gacgagcatc acaaaaatcg acgctcaagt cagaggtggc gaaacccgac    1140
aggactataa agataccagg cgtttccccc tggaagctcc ctcgtgcgct ctcctgttcc   1200
gaccctgccg cttaccggat acctgtccgc ctttctccct tcgggaagcg tggcgctttc   1260
tcatagctca cgctgtaggt atctcagttc ggtgtaggtc gttcgctcca agctgggctg   1320
tgtgcacgaa ccccccgttc agcccgaccg ctgcgcctta ccggtaact atcgtcttga    1380 gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt ttttgtttg    1620 caagcagcag attacgcgca gaaaaaaagg atctcaagaa gatcctttga tcttttctac   1680
ggggtctgac gctcagctag cgctcagaag aactcgtcaa gaaggcgata gaaggcgatg   1740
cgctgcgaat cgggagcggc gataccgtaa agcacgagga gcggtcagc ccattcgccg    1800 ccaagctctt cagcaatatc acgggtagcc aacgctatgt cctgatagcg gtccgccaca   1860
cccagccggc cacagtcgat gaatccagaa agcggccat tttccaccat gatattcggc    1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag gcaccggac    2340 aggtcggtct tgacaaaaag aaccgggcgc ccctgcgctg acagccggaa cacggcggca   2400
tcagagcagc cgattgtctg ttgtgcccag tcatagccga atagcctctc acccaagcg    2460 gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                         2725
```

<210> SEQ ID NO 24
<211> LENGTH: 2725
<212> TYPE: DNA

<213> ORGANISM: Artificial Sequence
<220> FEATURE:
<223> OTHER INFORMATION: Codon optimized HV-GHRH expression plasmid

<400> SEQUENCE: 24

```
ccaccgcggt ggcggccgtc cgccctcggc accatcctca cgacacccaa atatggcgac      60
gggtgaggaa tggtggggag ttattttttag agcggtgagg aaggtgggca ggcagcaggt     120
gttggcgctc taaaaataac tcccgggagt tattttttaga gcgaggaat ggtgacacc      180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa gcccaactc      360
cccgaaccac tcagggtcct gtggacagct cacctagctg ccatggtgct ctgggtgttc     420
ttctttgtga tcctcaccct cagcaacagc tcccactgct ccccacctcc ccctttgacc     480
ctcaggatgc ggcggcacgt agatgccatc ttcaccaaca gctaccggaa ggtgctggcc     540
cagctgtccg cccgcaagct gctccaggac atcctgaaca ggcagcaggg agagaggaac     600
caagagcaag gagcataatg acatcaagct tatcggggtg catccctgt gaccctccc       660
cagtgcctct cctggccctg gaagttgcca ctccagtgcc caccagcctt gtcctaataa     720
aattaagttg catcattttg tctgactagg tgtccttcta taatattatg ggtggaggg      780
gggtggtatg gagcaagggg caagttggga agacaacctg tagggctcga gggggggccc     840
ggtaccagct tttgttccct ttagtgaggg ttaatttcga gcttggtctt ccgcttcctc     900
gctcactgac tcgctgcgct cggtcgttcg gctgcggcga gcggtatcag ctcactcaaa     960
ggcggtaata cggttatcca cagaatcagg ggataacgca ggaaagaaca tgtgagcaaa    1020
aggccagcaa aaggccagga accgtaaaaa ggccgcgttg ctggcgtttt tccataggct    1080
ccgcccccct gacgagcatc acaaaaatcg acgctcaagt cagaggtggc gaaacccgac    1140
aggactataa agataccagg cgtttccccc tggaagctcc ctcgtgcgct ctcctgttcc    1200
gaccctgccg cttaccggat acctgtccgc ctttctccct cgggaagcg tggcgctttc     1260
tcatagctca cgctgtaggt atctcagttc ggtgtaggtc gttcgctcca agctgggctg    1320
tgtgcacgaa ccccccgttc agcccgaccg ctgcgcctta ccggtaact atcgtcttga    1380
gtccaacccg gtaagacacg acttatcgcc actggcagca gccactggta acaggattag    1440
cagagcgagg tatgtaggcg gtgctacaga gttcttgaag tggtggccta actacggcta    1500
cactagaaga acagtatttg gtatctgcgc tctgctgaag ccagttacct tcggaaaaag    1560
agttggtagc tcttgatccg gcaaacaaac caccgctggt agcggtggtt ttttttgttta    1620
caagcagcag attacgcgca gaaaaaaagg atctcaagaa gatcctttga tctttctac    1680
ggggtctgac gctcagctag cgctcagaag aactcgtcaa gaaggcgata gaaggcgatg    1740
cgctgcgaat cgggagcggc gataccgtaa gcacgagga gcggtcagc ccattcgccg      1800
ccaagctctt cagcaatatc acgggtagcc aacgctatgt cctgatagcg gtccgccaca    1860
cccagccggc cacagtcgat gaatccagaa aagcggccat tttccaccat gatattcggc    1920
aagcaggcat cgccatgagt cacgacgaga tcctcgccgt cgggcatgcg cgccttgagc    1980
ctggcgaaca gttcggctgg cgcgagcccc tgatgctctt cgtccagatc atcctgatcg    2040
acaagaccgg cttccatccg agtacgtgct cgctcgatgc gatgtttcgc ttggtggtcg    2100
aatgggcagg tagccggatc aagcgtatgc agccgccgca ttgcatcagc catgatggat    2160
actttctcgg caggagcaag gtgagatgac aggagatcct gccccggcac ttcgcccaat    2220
```

```
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc cacccaagcg   2460
gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                          2725
```

<210> SEQ ID NO 25
<211> LENGTH: 2505
<212> TYPE: DNA
<213> ORGANISM: Artificial Sequence
<220> FEATURE:
<223> OTHER INFORMATION: Codon optimized pig-GHRH expression plasmid

<400> SEQUENCE: 25

```
ccaccgcggt ggcggccgtc cgccctcggc accatcctca cgacacccaa atatggcgac     60
gggtgaggaa tggtggggag ttatttttag agcggtgagg aaggtgggca ggcagcaggt    120
gttggcgctc taaaaataac tcccgggagt tatttttaga gcggaggaat ggtggacacc    180
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctccaggac atcatgagca ggcagcaggg agagaggaac    600
caagagcaag gagcataatg aaagcttatc ggggtggcat ccctgtgacc cctccccagt    660
gcctctcctg gccctggaag ttgccactcc agtgcccacc agccttgtcc taataaaatt    720
aagttgcatc attttgtctg actaggtgtc cttctataat attatggggt ggaggggggt    780
ggtatggagc aaggggcaag ttgggaagac aacctgtagg gctcgagggg gggcccggta    840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc cgcctttctc ccttcgggaa   1080
gcgtggcgct ttctcatagc tcacgctgta ggtatctcag ttcggtgtag tcgttcgct    1140 ccaagctggg ctgtgtgcac gaaccccccg ttcagcccga ccgctgcgcc ttatccggta   1200
actatcgtct tgagtccaac ccggtaagac acgacttatc gccactggca gcagccactg   1260
gtaacaggat tagcagagcg aggtatgtag gcggtgctac agagttcttg aagtggtggc   1320
ctaactacgg ctacactaga agaacagtat ttggtatctg cgctctgctg aagccagtta   1380
ccttcggaaa aagagttggt agctcttgat ccggcaaaca aaccaccgct ggtagcggtg   1440
gtttttttgt ttgcaagcag cagattacgc gcagaaaaaa aggatctcaa gaagatcctt   1500
tgatcttttc tacggggtct gacgctcagc tagcgctcag aagaactcgt caagaaggcg   1560
```

-continued

| | |
|---|---|
| atagaaggcg atgcgctgcg aatcgggagc ggcgataccg taaagcacga ggaagcggtc | 1620 |
| agcccattcg ccgccaagct cttcagcaat atcacgggta gccaacgcta tgtcctgata | 1680 |
| gcggtccgcc acacccagcc ggccacagtc gatgaatcca gaaaagcggc catttccac | 1740 |
| catgatattc ggcaagcagg catcgccatg agtcacgacg agatcctcgc cgtcgggcat | 1800 |
| gcgcgccttg agcctggcga acagttcggc tggcgcgagc ccctgatgct cttcgtccag | 1860 |
| atcatcctga tcgacaagac cggcttccat ccgagtacgt gctcgctcga tgcgatgttt | 1920 |
| cgcttggtgg tcgaatgggc aggtagccgg atcaagcgta tgcagccgcc gcattgcatc | 1980 |
| agccatgatg gatactttct cggcaggagc aaggtgagat gacaggagat cctgccccgg | 2040 |
| cacttcgccc aatagcagcc agtcccttcc cgcttcagtg acaacgtcga gcacagctgc | 2100 |
| gcaaggaacg cccgtcgtgg ccagccacga tagccgcgct gcctcgtcct gcagttcatt | 2160 |
| cagggcaccg gacaggtcgg tcttgacaaa aagaaccggg cgccctgcg ctgacagccg | 2220 |
| gaacacggcg gcatcagagc agccgattgt ctgttgtgcc cagtcatagc cgaatagcct | 2280 |
| ctccacccaa gcggccggag aacctgcgtg caatccatct tgttcaatca tgcgaaacga | 2340 |
| tcctcatcct gtctcttgat cagatcttga tcccctgcgc catcagatcc ttggcggcaa | 2400 |
| gaaagccatc cagtttactt tgcagggctt cccaacctta ccagagggcg ccccagctgg | 2460 |
| caattccggt tcgcttgctg tccataaaac cgcccagtct gagct | 2505 |

<210> SEQ ID NO 26
<211> LENGTH: 2716
<212> TYPE: DNA
<213> ORGANISM: Artificial Sequence
<220> FEATURE:
<223> OTHER INFORMATION: Codon optimized dog-GHRH expression plasmid

<400> SEQUENCE: 26

| | |
|---|---|
| ccaccgcggt ggcggccgtc cgccctcggc accatcctca cgacacccaa atatggcgac | 60 |
| gggtgaggaa tggtgggagg ttattttttag agcggtgagg aaggtgggca ggcagcaggt | 120 |
| gttggcgctc taaaaataac tcccgggagt tattttttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |
| ggcggcccac gagctacccg gaggagcggg aggcgccaag cggatcccaa ggcccaactc | 360 |
| cccgaaccac tcagggtcct gtggacagct cacctagctg ccatggtgct ctgggtgttc | 420 |
| ttcctggtga tcctcacccct cagcagtggt tccactctt cccgccatc cctgcccatc | 480 |
| agaatccctc ggtatgcaga cgccatcttc accaacagct accggaaggt gctgggccag | 540 |
| ctgtccgccc gcaagctcct scaggacatc atgagccggc agcagggaga gagaaaccgg | 600 |
| gagcaaggag catagtaagc ttatcggggt ggcatccctg tgaccctcc ccagtgcctc | 660 |
| tcctggcccct ggaagttgcc actccagtgc ccaccagcct tgtcctaata aaattaagtt | 720 |
| gcatcatttt gtctgactag gtgtccttct ataatattat ggggtggagg ggggtggtat | 780 |
| ggagcaaggg gcaagttggg aagacaacct gtagggctcg agggggggcc cggtaccagc | 840 |
| ttttgttccc tttagtgagg gttaatttcg agcttggtct tccgcttcct cgctcactga | 900 |
| ctcgctgcgc tcggtcgttc ggctgcggcg agcggtatca gctcactcaa aggcggtaat | 960 |
| acggttatcc acagaatcag gggataacgc aggaaagaac atgtgagcaa aaggccagca | 1020 |
| aaaggccagg aaccgtaaaa aggccgcgtt gctggcgttt ttccataggc tccgccccc | 1080 |
| tgacgagcat cacaaaaatc gacgctcaag tcagaggtgg cgaaacccga caggactata | 1140 |

| aagataccag gcgtttcccc ctggaagctc cctcgtgcgc tctcctgttc cgaccctgcc | 1200 |
| gcttaccgga tacctgtccg cctttctccc ttcgggaagc gtggcgcttt ctcatagctc | 1260 |
| acgctgtagg tatctcagtt cggtgtaggt cgttcgctcc aagctgggct gtgtgcacga | 1320 |
| accccccgtt cagcccgacc gctgcgcctt atccggtaac tatcgtcttg agtccaaccc | 1380 |
| ggtaagacac gacttatcgc cactggcagc agccactggt aacaggatta gcagagcgag | 1440 |
| gtatgtaggc ggtgctacag agttcttgaa gtggtggcct aactacggct acactagaag | 1500 |
| aacagtattt ggtatctgcg ctctgctgaa gccagttacc ttcggaaaaa gagttggtag | 1560 |
| ctcttgatcc ggcaaacaaa ccaccgctgg tagcggtggt ttttttgttt acaagcagca | 1620 |
| gattacgcgc agaaaaaaag gatctcaaga agatcctttg atcttttcta cggggtctga | 1680 |
| cgctcagcta gcgctcagaa gaactcgtca agaaggcgat agaaggcgat gcgctgcgaa | 1740 |
| tcgggagcgg cgataccgta agcacgagg aagcggtcag cccattcgcc gccaagctct | 1800 |
| tcagcaatat cacgggtagc caacgctatg tcctgatagc ggtccgccac acccagccgg | 1860 |
| ccacagtcga tgaatccaga aaagcggcca ttttccacca tgatattcgg caagcaggca | 1920 |
| tcgccatgag tcacgacgag atcctcgccg tcgggcatgc gcgccttgag cctggcgaac | 1980 |
| agttcggctg gcgcgagccc ctgatgctct tcgtccagat catcctgatc gacaagaccg | 2040 |
| gcttccatcc gagtacgtgc tcgctcgatg cgatgtttcg cttggtggtc gaatgggcag | 2100 |
| gtagccggat caagcgtatg cagccgccgc attgcatcag ccatgatgga ctttctctcg | 2160 |
| gcaggagcaa ggtgagatga caggagatcc tgccccggca cttcgcccaa tagcagccag | 2220 |
| tcccttcccg cttcagtgac aacgtcgagc acagctgcgc aaggaacgcc cgtcgtggcc | 2280 |
| agccacgata gccgcgctgc ctcgtcctgc agttcattca gggcaccgga caggtcggtc | 2340 |
| ttgacaaaaa gaaccgggcg cccctgcgct gacagccgga acacgcggc atcagagcag | 2400 |
| ccgattgtct gttgtgccca gtcatagccg aatagcctct ccacccaagc ggccggagaa | 2460 |
| cctgcgtgca atccatcttg ttcaatcatg cgaaacgatc ctcatcctgt ctcttgatca | 2520 |
| gatcttgatc ccctgcgcca tcagatcctt ggcggcaaga aagccatcca gtttactttg | 2580 |
| cagggcttcc caaccttacc agagggcgcc ccagctggca attccggttc gcttgctgtc | 2640 |
| cataaaaccg cccagtctag caactgttgg gaagggcgat cgtgtaatac gactcactat | 2700 |
| agggcgaatt ggagct | 2716 |

<210> SEQ ID NO 27
<211> LENGTH: 2715
<212> TYPE: DNA
<213> ORGANISM: Artificial Sequence
<220> FEATURE:
<223> OTHER INFORMATION: Codon optimized bovine-GHRH expression plasmid

<400> SEQUENCE: 27

| ccaccgcggt ggcggccgtc cgccctcggc accatcctca cgacacccaa atatggcgac | 60 |
| gggtgaggaa tggtggggag ttattttag agcggtgagg aaggtgggca ggcagcaggt | 120 |
| gttggcgctc taaaaataac tcccgggagt tattttaga gcggaggaat ggtggacacc | 180 |
| caaatatggc gacggttcct cacccgtcgc catatttggg tgtccgccct cggccggggc | 240 |
| cgcattcctg gggccgggc ggtgctcccg ccgcctcga taaaaggctc cggggccggc | 300 |
| ggcggcccac gagctacccg gaggagcggg aggcgccaag cggatcccaa gcccaactc | 360 |
| cccgaaccac tcagggtcct gtggacagct cacctagctg ccatggtgct gtgggtgttc | 420 |
| ttcctggtga ccctgaccct gagcagcggc tcccacggct ccctgccctc ccagcctctg | 480 |

```
cgcatccctc gctacgccga cgccatcttc accaacagct accgcaaggt gctcggccag    540
ctcagcgccc gcaagctcct gcaggacatc atgaaccggc agcagggcga gcgcaaccag    600
gagcagggag cctgataagc ttatcggggt ggcatccctg tgacccctcc ccagtgcctc    660 tcctggcccct ggaagttgcc actccagtgc ccaccagcct tgtcctaata aaattaagtt    720
gcatcatttt gtctgactag gtgtccttct ataatattat ggggtggagg ggggtggtat    780
ggagcaaggg gcaagttggg aagacaacct gtagggctcg agggggggcc cggtaccagc    840
ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca   1020
aaaggccagg aaccgtaaaa aggccgcgtt gctggcgttt ttccataggc tccgcccccc   1080
tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta agcacgagga agcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga ctttctcg   2160 gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc cctgcgcca tcagatcctt ggcggcaaga aagccatcca gtttactttg   2580
cagggcttcc caaccttacc agagggcgcc ccagctggca attccggttc gcttgctgtc   2640
cataaaaccg cccagtctag caactgttgg aagggcgat cgtgtaatac gactcactat   2700
agggcgaatt ggagc                                                    2715
```

<210> SEQ ID NO 28
<211> LENGTH: 2716
<212> TYPE: DNA

<213> ORGANISM: Artificial Sequence
<220> FEATURE:
<223> OTHER INFORMATION: Codon optimized cat-GHRH expression plasmid

<400> SEQUENCE: 28

```
ccaccgcggt ggcggccgtc cgccctcggc accatcctca cgacacccaa atatggcgac      60
gggtgaggaa tggtggggag ttatttttag agcggtgagg aaggtgggca ggcagcaggt     120
gttggcgctc taaaaataac tcccgggagt tatttttaga gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct ctgggtgttc     420
ttcctggtga tcctcacccs ssacagtggc tcccactgct ccccgccatc cctgcccctc     480
agaatgcctc ggtatgcaga tgccatcttc accaacagct accggaaggt gctgggtcag     540
ctgtctgccc gcaagctact gcaggacatc atgagcagac agcagggaga gagaaaccag     600
gagcaaggag cataataagc ttatcggggt ggcatccctg tgacccctcc ccagtgcctc     660
tcctggccct ggaagttgcc actccagtgc ccaccagcct tgtcctaata aaattaagtt     720
gcatcatttt gtctgactag gtgtccttct ataatattat ggggtggagg gggtggtat      780
ggagcaaggg gcaagttggg aagacaacct gtagggctcg aggggggggcc cggtaccagc     840
ttttgttccc tttagtgagg gttaatttcg agcttggtct tccgcttcct cgctcactga     900
ctcgctgcgc tcggtcgttc ggctgcggcg agcggtatca gctcactcaa aggcggtaat     960
acggttatcc acagaatcag gggataacgc aggaaagaac atgtgagcaa aaggccagca    1020
aaaggccagg aaccgtaaaa aggccgcgtt gctggcgttt ttccataggc tccgcccccc    1080
tgacgagcat cacaaaaatc gacgctcaag tcagaggtgg cgaaacccga caggactata    1140
aagataccag gcgtttcccc ctggaagctc cctcgtgcgc tctcctgttc cgaccctgcc    1200
gcttaccgga tacctgtccg cctttctccc ttcgggaagc gtggcgcttt ctcatagctc    1260
acgctgtagg tatctcagtt cggtgtaggt cgttcgctcc aagctgggct gtgtgcacga    1320
accccccgtt cagcccgacc gctgcgcctt atccggtaac tatcgtcttg agtccaaccc    1380
ggtaagacac gacttatcgc cactggcagc agccactggt aacaggatta gcagagcgag    1440
gtatgtaggc ggtgctacag agttcttgaa gtggtggcct aactacggct acactagaag    1500
aacagtattt ggtatctgcg ctctgctgaa gccagttacc ttcggaaaaa gagttggtag    1560
ctcttgatcc ggcaaacaaa ccaccgctgg tagcggtggt ttttttgttt acaagcagca    1620
gattacgcgc agaaaaaaag gatctcaaga agatcctttg atcttttcta cggggtctga    1680
cgctcagcta gcgctcagaa gaactcgtca agaaggcgat agaaggcgat gcgctgcgaa    1740
tcgggagcgg cgataccgta agcacgagg aagcggtcag cccattcgcc gccaagctct    1800
tcagcaatat cacgggtagc caacgctatg tcctgatagc ggtccgccac acccagccgg    1860
ccacagtcga tgaatccaga aaagcggcca ttttccacca tgatattcgg caagcaggca    1920
tcgccatgag tcacgacgag atcctcgccg tcgggcatgc gcgccttgag cctggcgaac    1980
agttcggctg gcgcgagccc ctgatgctct tcgtccagat catcctgatc gacaagaccg    2040
gcttccatcc gagtacgtgc tcgctcgatg cgatgtttcg cttggtggtc gaatgggcag    2100
gtagccggat caagcgtatg cagccgccgc attgcatcag ccatgatgga tactttctcg    2160
gcaggagcaa ggtgagatga caggagatcc tgccccggca cttcgcccaa tagcagccag    2220
```

| tcccttcccg | cttcagtgac | aacgtcgagc | acagctgcgc | aaggaacgcc | cgtcgtggcc | 2280 |
| agccacgata | gccgcgctgc | ctcgtcctgc | agttcattca | gggcaccgga | caggtcggtc | 2340 |
| ttgacaaaaa | gaaccgggcg | cccctgcgct | gacagccgga | acacggcggc | atcagagcag | 2400 |
| ccgattgtct | gttgtgccca | gtcatagccg | aatagcctct | ccacccaagc | ggccggagaa | 2460 |
| cctgcgtgca | atccatcttg | ttcaatcatg | cgaaacgatc | ctcatcctgt | ctcttgatca | 2520 |
| gatcttgatc | ccctgcgcca | tcagatcctt | ggcggcaaga | aagccatcca | gtttactttg | 2580 |
| cagggcttcc | aaccttacc | agagggcgcc | ccagctggca | attccggttc | gcttgctgtc | 2640 |
| cataaaaccg | cccagtctag | caactgttgg | gaagggcgat | cgtgtaatac | gactcactat | 2700 |
| agggcgaatt | ggagct |  |  |  |  | 2716 |

<210> SEQ ID NO 29
<211> LENGTH: 2739
<212> TYPE: DNA
<213> ORGANISM: Artificial Sequeance
<220> FEATURE:
<223> OTHER INFORMATION: Codon optimized TI-GHRH expression plasmid

<400> SEQUENCE: 29

| ccaccgcggt | ggcggccgtc | cgccctcggc | accatcctca | cgacacccaa | atatggcgac | 60 |
| gggtgaggaa | tggtggggag | ttatttttag | agcggtgagg | aaggtgggca | ggcagcaggt | 120 |
| gttggcgctc | taaaaataac | tcccgggagt | tatttttaga | gcggaggaat | ggtggacacc | 180 |
| caaatatggc | gacggttcct | cacccgtcgc | catatttggg | tgtccgccct | cggccggggc | 240 |
| cgcattcctg | ggggccgggc | ggtgctcccg | cccgcctcga | taaaaggctc | cggggccggc | 300 |
| ggcggcccac | gagctacccg | gaggagcggg | aggcgccaag | cggatcccaa | ggcccaactc | 360 |
| cccgaaccac | tcagggtcct | gtggacagct | cacctagctg | ccatggtgct | ctgggtgttc | 420 |
| ttctttgtga | tcctcaccct | cagcaacagc | tcccactgct | ccccacctcc | ccctttgacc | 480 |
| ctcaggatgc | ggcggtatat | cgatgccatc | ttcaccaaca | gctaccggaa | ggtgctggcc | 540 |
| cagctgtccg | cccgcaagct | gctccaggac | atcctgaaca | ggcagcaggg | agagaggaac | 600 |
| caagagcaag | gagcataatg | actgcaggaa | ttcgatatca | agcttatcgg | ggtggcatcc | 660 |
| ctgtgacccc | tccccagtgc | ctctcctggc | cctggaagtt | gccactccag | tgcccaccag | 720 |
| ccttgtccta | ataaaattaa | gttgcatcat | tttgtctgac | taggtgtcct | tctataatat | 780 |
| tatggggtgg | aggggggtgg | tatggagcaa | ggggcaagtt | gggaagacaa | cctgtagggc | 840 |
| tcgaggggggg | gcccggtacc | agcttttgtt | cccttagtg | agggttaatt | tcgagcttgg | 900 |
| tcttccgctt | cctcgctcac | tgactcgctg | cgctcggtcg | ttcggctgcg | gcgagcggta | 960 |
| tcagctcact | caaaggcggt | aatacggtta | tccacagaat | caggggataa | cgcaggaaag | 1020 |
| aacatgtgag | caaaaggcca | gcaaaaggcc | aggaaccgta | aaaaggccgc | gttgctggcg | 1080 |
| tttttccata | ggctccgccc | ccctgacgag | catcacaaaa | atcgacgctc | aagtcagagg | 1140 |
| tggcgaaacc | cgacaggact | ataaagatac | caggcgtttc | ccctggaag | ctccctcgtg | 1200 |
| cgctctcctg | ttccgaccct | gccgcttacc | ggatacctgt | ccgcctttct | cccttcggga | 1260 |
| agcgtggcgc | tttctcatag | ctcacgctgt | aggtatctca | gttcggtgta | ggtcgttcgc | 1320 |
| tccaagctgg | gctgtgtgca | cgaaccccc | gttcagcccg | accgctgcgc | cttatccggt | 1380 |
| aactatcgtc | ttgagtccaa | cccggtaaga | cacgacttat | cgccactggc | agcagccact | 1440 |
| ggtaacagga | ttagcagagc | gaggtatgta | ggcggtgcta | cagagttctt | gaagtggtgg | 1500 |
| cctaactacg | gctacactag | aagaacagta | tttggtatct | gcgctctgct | gaagccagtt | 1560 |

-continued

```
accttcggaa aaagagttgg tagctcttga tccggcaaac aaaccaccgc tggtagcggt    1620
ggttttttg tttacaagca gcagattacg cgcagaaaaa aaggatctca agaagatcct    1680
ttgatctttt ctacggggtc tgacgctcag ctagcgctca agaagaactcg tcaagaaggc   1740
gatagaaggc gatgcgctgc gaatcggag cggcgatacc gtaaagcacg aggaagcggt    1800
cagcccattc gccgccaagc tcttcagcaa tatcacgggt agccaacgct atgtcctgat   1860
agcggtccgc cacacccagc cggccacagt cgatgaatcc agaaaagcgg ccattttcca    1920
ccatgatatt cggcaagcag gcatcgccat gagtcacgac gagatcctcg ccgtcgggca    1980
tgcgcgcctt gagcctggcg aacagttcgg ctggcgcgag cccctgatgc tcttcgtcca   2040
gatcatcctg atcgacaaga ccggcttcca tccgagtacg tgctcgctcg atgcgatgtt    2100
tcgcttggtg gtcgaatggg caggtagccg gatcaagcgt atgcagccgc cgcattgcat    2160
cagccatgat ggatactttc tcggcaggag caaggtgaga tgacaggaga tcctgccccg    2220
gcacttcgcc caatagcagc cagtcccttc ccgcttcagt gacaacgtcg agcacagctg    2280
cgcaaggaac gcccgtcgtg gccagccacg atagccgcgc tgcctcgtcc tgcagttcat    2340
tcagggcacc ggacaggtcg gtcttgacaa aaagaaccgg gcgcccctgc gctgacagcc    2400
ggaacacggc ggcatcagag cagccgattg tctgttgtgc ccagtcatag ccgaatagcc    2460
tctccaccca gcggccgga gaacctgcgt gcaatccatc ttgttcaatc atgcgaaacg    2520
atcctcatcc tgtctcttga tcagatcttg atcccctgcg ccatcagatc cttggcggca    2580
agaaagccat ccagttactt ttgcagggct cccaaccttt accagagggc gcccagctg    2640
gcaattccgg ttcgcttgct gtccataaaa ccgcccagtc tagcaactgt tgggaagggc    2700
gatcgtgtaa tacgactcac tatagggcga attggagct                            2739
```

<210> SEQ ID NO 30
<211> LENGTH: 2716
<212> TYPE: DNA
<213> ORGANISM: Artificial Sequence
<220> FEATURE:
<223> OTHER INFORMATION: Codon optimized ovine-GHRH expression plasmid

<400> SEQUENCE: 30

```
ccaccgcggt ggcggccgtc cgccctcggc accatcctca cgacacccaa atatggcgac      60
gggtgaggaa tggtggggag ttattttag agcggtgagg aaggtgggca ggcagcaggt      120
gttggcgctc taaaaataac tcccgggagt tattttaga gcggaggaat ggtggacacc      180
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgcaag cggatcccaa ggcccaactc    360
cccgaaccac tcagggtcct gtggacagct cacctagctg ccatggtgct gtgggtgttc   420
ttcctggtga ccctgaccct gagcagcgga agccacggca gcctgcccag ccagcccctg   480
aggatcccta ggtacgccga cgccatcttc accaacagct acaggaagat cctgggccag   540
ctgagcgcta ggaagctcct gcaggacatc atgaacaggc agcagggcga gaggaaccag   600
gagcagggcg cctgataagc ttatcggggt ggcatccctg tgaccccctcc ccagtgcctc   660
tcctggccct ggaagttgcc actccagtgc ccaccagcct tgtcctaata aaattaagtt   720
gcatcatttt gtctgactag gtgtccttct ataatattat gggtggagg gggtggtat    780
ggagcaaggg gcaagttggg aagacaacct gtagggctcg agggggggcc cggtaccagc   840
ttttgttccc tttagtgagg gttaatttcg agcttggtct tccgcttcct cgctcactga   900
```

| | |
|---|---|
| ctcgctgcgc tcggtcgttc ggctgcggcg agcggtatca gctcactcaa aggcggtaat | 960 |
| acggttatcc acagaatcag gggataacgc aggaaagaac atgtgagcaa aaggccagca | 1020 |
| aaaggccagg aaccgtaaaa aggccgcgtt gctggcgttt ttccataggc tccgcccccc | 1080 |
| tgacgagcat cacaaaaatc gacgctcaag tcagaggtgg cgaaacccga caggactata | 1140 |
| aagataccag gcgtttcccc ctggaagctc cctcgtgcgc tctcctgttc cgaccctgcc | 1200 |
| gcttaccgga tacctgtccg cctttctccc ttcgggaagc gtggcgcttt ctcatagctc | 1260 |
| acgctgtagg tatctcagtt cggtgtaggt cgttcgctcc aagctgggct gtgtgcacga | 1320 |
| accccccgtt cagcccgacc gctgcgcctt atccggtaac tatcgtcttg agtccaaccc | 1380 |
| ggtaagacac gacttatcgc cactggcagc agccactggt aacaggatta gcagagcgag | 1440 |
| gtatgtaggc ggtgctacag agttcttgaa gtggtggcct aactacggct acactagaag | 1500 |
| aacagtattt ggtatctgcg ctctgctgaa gccagttacc ttcggaaaaa gagttggtag | 1560 |
| ctcttgatcc ggcaaacaaa ccaccgctgg tagcggtggt ttttttgttt acaagcagca | 1620 |
| gattacgcgc agaaaaaaag gatctcaaga agatcctttg atcttttcta cggggtctga | 1680 |
| cgctcagcta gcgctcagaa gaactcgtca agaaggcgat agaaggcgat gcgctgcgaa | 1740 |
| tcgggagcgg cgataccgta agcacgagg aagcggtcag cccattcgcc gccaagctct | 1800 |
| tcagcaatat cacgggtagc caacgctatg tcctgatagc ggtccgccac acccagccgg | 1860 |
| ccacagtcga tgaatccaga aaagcggcca ttttccacca tgatattcgg caagcaggca | 1920 |
| tcgccatgag tcacgacgag atcctcgccg tcgggcatgc gcgccttgag cctggcgaac | 1980 |
| agttcggctg gcgcgagccc ctgatgctct tcgtccagat catcctgatc gacaagaccg | 2040 |
| gcttccatcc gagtacgtgc tcgctcgatg cgatgtttcg cttggtggtc gaatgggcag | 2100 |
| gtagccggat caagcgtatg cagccgccgc attgcatcag ccatgatgga tactttctcg | 2160 |
| gcaggagcaa ggtgagatga caggagatcc tgccccggca cttcgcccaa tagcagccag | 2220 |
| tcccttcccg cttcagtgac aacgtcgagc acagctgcgc aaggaacgcc cgtcgtggcc | 2280 |
| agccacgata gccgcgctgc ctcgtcctgc agttcattca gggcaccgga caggtcggtc | 2340 |
| ttgacaaaaa gaaccgggcg cccctgcgct gacagccgga acacggcggc atcagagcag | 2400 |
| ccgattgtct gttgtgccca gtcatagccg aatagcctct ccacccaagc ggccggagaa | 2460 |
| cctgcgtgca atccatcttg ttcaatcatg cgaaacgatc ctcatcctgt ctcttgatca | 2520 |
| gatcttgatc ccctgcgcca tcagatcctt ggcggcaaga aagccatcca gtttactttg | 2580 |
| cagggcttcc caaccttacc agagggcgcc cagctggcaa attccggttc gcttgctgtc | 2640 |
| cataaaaccg cccagtctag caactgttgg gaagggcgat cgtgtaatac gactcactat | 2700 |
| agggcgaatt ggagct | 2716 |

<210> SEQ ID NO 31
<211> LENGTH: 2725
<212> TYPE: DNA
<213> ORGANISM: Artificial Sequence
<220> FEATURE:
<223> OTHER INFORMATION: Optimized chicken-GHRH expression plasmid

<400> SEQUENCE: 31

| | |
|---|---|
| ccaccgcggt ggcggccgtc cgccctcggc accatcctca cgacacccaa atatggcgac | 60 |
| gggtgaggaa tggtggggag ttatttttag agcggtgagg aaggtgggca ggcagcaggt | 120 |
| gttggcgctc taaaaataac tcccgggagt tattttttaga gcggaggaat ggtggacacc | 180 |
| caaatatggc gacggttcct cacccgtcgc catatttggg tgtccgccct cggccggggc | 240 |

```
cgcattcctg ggggccgggc ggtgctcccg cccgcctcga taaaaggctc cggggccggc      300
ggcggcccac gagctacccg gaggagcggg aggcgccaag cggatcccaa ggcccaactc      360
cccgaaccac tcagggtcct gtggacagct cacctagctg ccatggccct gtgggtgttc      420
tttgtgctgc tgaccctgac ctccggaagc cactgcagcc tgccaccag cccaccttc       480 cgcgtcaggc gccacgccga cggcatcttc agcaaggcct accgcaagct cctgggccag      540
ctgagcgcac gcaactacct gcacagcctg atggccaagc gcgtgggcag cggactggga      600
gacgaggccg agcccctgag ctgataagct tatcggggtg gcatccctgt gaccccctccc     660 cagtgcctct cctggccctg gaagttgcca ctccagtgcc caccagcctt gtcctaataa      720
aattaagttg catcattttg tctgactagg tgtccttcta taatattatg gggtggaggg      780
gggtggtatg gagcaagggg caagttggga agacaacctg tagggctcga gggggggccc      840
ggtaccagct tttgttccct ttagtgaggg ttaatttcga gcttggtctt ccgcttcctc      900
gctcactgac tcgctgcgct cggtcgttcg gctgcggcga gcggtatcag ctcactcaaa      960
ggcggtaata cggttatcca cagaatcagg ggataacgca ggaaagaaca tgtgagcaaa     1020
aggccagcaa aaggccagga accgtaaaaa ggccgcgttg ctggcgtttt tccataggct     1080
ccgcccccct gacgagcatc acaaaaatcg acgctcaagt cagaggtggc gaaacccgac     1140
aggactataa agataccagg cgtttccccc tggaagctcc ctcgtgcgct ctcctgttcc     1200
gaccctgccg cttaccggat acctgtccgc ctttctccct tcgggaagcg tggcgctttc     1260
tcatagctca cgctgtaggt atctcagttc ggtgtaggtc gttcgctcca agctgggctg     1320
tgtgcacgaa ccccccgttc agcccgaccg ctgcgcctta tccggtaact atcgtcttga     1380
gtccaacccg gtaagacacg acttatcgcc actggcagca gccactggta acaggattag     1440
cagagcgagg tatgtaggcg gtgctacaga gttcttgaag tggtggccta actacggcta     1500
cactagaaga acagtatttg gtatctgcgc tctgctgaag ccagttacct tcggaaaaag     1560
agttggtagc tcttgatccg gcaaacaaac caccgctggt agcggtggtt ttttgttta     1620 caagcagcag attacgcgca gaaaaaaagg atctcaagaa gatcctttga tcttttctac     1680
ggggtctgac gctcagctag cgctcagaag aactcgtcaa gaaggcgata gaaggcgatg     1740
cgctgcgaat cgggagcggc gataccgtaa agcacgagga gcggtcagc ccattcgccg      1800 ccaagctctt cagcaatatc acgggtagcc aacgctatgt cctgatagcg gtccgccaca     1860
cccagccggc cacagtcgat gaatccagaa aagcggccat tttccaccat gatattcggc     1920
aagcaggcat cgccatgagt cacgacgaga tcctcgccgt cgggcatgcg cgccttgagc     1980
ctggcgaaca gttcggctgg cgcgagcccc tgatgctctt cgtccagatc atcctgatcg     2040
acaagaccgg cttccatccg agtacgtgct cgctcgatgc gatgtttcgc ttggtggtcg     2100
aatgggcagg tagccggatc aagcgtatgc agccgccgca ttgcatcagc catgatggat     2160
actttctcgg caggagcaag gtgagatgac aggagatcct gccccggcac ttcgcccaat     2220
agcagccagt cccttcccgc ttcagtgaca acgtcgagca cagctgcgca aggaacgccc     2280
gtcgtggcca gccacgatag ccgcgctgcc tcgtcctgca gttcattcag gcaccggac      2340 aggtcggtct tgacaaaaag aaccgggcgc ccctgcgctg acagccggaa cacggcggca     2400
tcagagcagc cgattgtctg ttgtgcccag tcatagccga atagcctctc cacccaagcg     2460
gccggagaac ctgcgtgcaa tccatcttgt tcaatcatgc gaaacgatcc tcatcctgtc     2520
tcttgatcag atcttgatcc cctgcgccat cagatccttg gcggcaagaa agccatccag     2580
tttactttgc agggcttccc aaccttacca gagggcgccc cagctggcaa ttccggttcg     2640
```

```
cttgctgtcc ataaaaccgc ccagtctagc aactgttggg aagggcgatc gtgtaatacg    2700
actcactata gggcgaattg gagct                                          2725

<210> SEQ ID NO 32
<211> LENGTH: 2505
<212> TYPE: DNA
<213> ORGANISM: Artificial Sequence
<220> FEATURE:
<223> OTHER INFORMATION: Codon optimized human-GHRH expression plasmid

<400> SEQUENCE: 32
ccaccgcggt ggcggccgtc cgccctcggc accatcctca cgacacccaa atatggcgac      60
gggtgaggaa tggtggggag ttatttttag agcggtgagg aaggtgggca ggcagcaggt     120
gttggcgctc taaaataac tcccgggagt tattttaga gcggaggaat ggtggacacc      180
caaatatggc gacggttcct cacccgtcgc catatttggg tgtccgccct cggccggggc     240
cgcattcctg ggggccgggc ggtgctcccg ccgcctcga taaaaggctc cggggccggc      300
ggcggcccac gagctacccg gaggagcggg aggcgccaag cggatcccaa ggcccaactc     360
cccgaaccac tcagggtcct gtggacagct cacctagctg ccatggtgct ctgggtgttc    420
ttctttgtga tcctcacccct cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctgcaggac atcatgagca ggcagcaggg agagagcaac    600
caagagcgag gagcataatg aaagcttatc ggggtggcat ccctgtgacc cctccccagt    660
gcctctcctg gccctggaag ttgccactcc agtgcccacc agccttgtcc taataaaatt    720
aagttgcatc attttgtctg actaggtgtc cttctataat attatgggt ggagggggt     780 ggtatggagc aaggggcaag ttgggaagac aacctgtagg gctcgagggg gggcccggta    840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc gcctttctc ccttcgggaa    1080 gcgtggcgct ttctcatagc tcacgctgta ggtatctcag ttcggtgtag gtcgttcgct   1140
ccaagctggg ctgtgtgcac gaaccccccg ttcagcccga ccgctgcgcc ttatccggta   1200
actatcgtct tgagtccaac ccggtaagac acgacttatc gccactggca gcagccactg   1260
gtaacaggat tagcagagcg aggtatgtag cggtgctac agagttcttg aagtggtggc    1320
ctaactacgg ctacactaga agaacagtat ttggtatctg cgctctgctg aagccagtta    1380
ccttcggaaa aagagttggt agctcttgat ccggcaaaca aaccaccgct ggtagcggtg   1440
gtttttttgt ttacaagcag cagattacgc gcagaaaaaa aggatctcaa gaagatcctt    1500
tgatcttttc tacggggtct gacgctcagc tagcgctcag aagaactcgt caagaaggcg   1560
atagaaggcg atgcgctgcg aatcgggagc ggcgataccg taaagcacga ggaagcggtc   1620
agcccattcg ccgccaagct cttcagcaat atcacgggta ccaacgctat gtcctgata   1680 gcggtccgcc acacccagcc ggccacagtc gatgaatcca gaaaagcggc catttttccac   1740 catgatattc ggcaagcagg catcgccatg agtcacgacg gatcctcgc cgtcgggcat    1800 gcgcgccttg agcctggcga acagttcggc tggcgcgagc cctgatgct cttcgtccag   1860 atcatcctga tcgacaagac cggcttccat ccgagtacgt gctcgctcga tgcgatgttt    1920
cgcttggtgg tcgaatgggc aggtagccgg atcaagcgta tgcagccgcc gcattgcatc   1980
```

```
agccatgatg gatactttct cggcaggagc aaggtgagat gacaggagat cctgccccgg    2040
cacttcgccc aatagcagcc agtcccttcc cgcttcagtg acaacgtcga gcacagctgc    2100
gcaaggaacg cccgtcgtgg ccagccacga tagccgcgct gcctcgtcct gcagttcatt    2160
cagggcaccg gacaggtcgg tcttgacaaa agaaccggg cgcccctgcg ctgacagccg     2220
gaacacggcg gcatcagagc agccgattgt ctgttgtgcc cagtcatagc cgaatagcct    2280
ctccacccaa gcggccggag aacctgcgtg caatccatct tgttcaatca tgcgaaacga    2340
tcctcatcct gtctcttgat cagatcttga tcccctgcgc catcagatcc ttggcggcaa    2400
gaaagccatc cagtttactt tgcagggctt cccaacctta ccagagggcg ccccagctgg    2460
caattccggt tcgcttgctg tccataaaac cgcccagtct gagct                   2505

<210> SEQ ID NO 33
<211> LENGTH: 3534
<212> TYPE: DNA
<213> ORGANISM: Artificial Sequence
<220> FEATURE:
<223> OTHER INFORMATION: Plasmid vector having a porcine wt-GHRH
      sequence

<400> SEQUENCE: 33
ccaccgcggt ggcggccgtc cgccctcggc accatcctca cgacacccaa atatggcgac      60
gggtgaggaa tggtgggag ttatttttag agcggtgagg aagtgggca ggcagcaggt      120 gttggcgctc taaaaataac tcccgggagt tattttttaga gcggaggaat ggtggacacc    180
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgcaag ctctagaact agtggatccc     360
aaggcccaac tccccgaacc actcagggtc ctgtggacag ctcacctagc tgccatggtg    420
ctctgggtgt tcttctttgt gatcctcacc ctcagcaaca gctcccactg ctcccccacct    480 ccccctttga ccctcaggat gcggcggtat gcagatgcca tcttcaccaa cagctaccgg    540
aaggtgctgg ccagctgtc cgcccgcaag ctgctccagg acatcatgag caggcagcag    600
ggagagagga accaagagca aggagcataa tgactgcagg aattcgatat caagcttatc    660
ggggtggcat ccctgtgacc cctccccagt gcctctcctg gccctggaag ttgccactcc    720
agtgcccacc agccttgtcc taataaaatt aagttgcatc attttgtctg actaggtgtc    780
cttctataat attatgggt ggagggggggt ggtatggagc aagggcaag ttgggaagac     840 aacctgtagg gcctgcgggg tctattggga accaagctgg agtgcagtgg cacaatcttg    900
gctcactgca atctccgcct cctgggttca agcgattctc ctgcctcagc ctcccgagtt    960
gttgggattc caggcatgca tgaccaggct cagctaattt tgttttttt ggtagagacg    1020 gggttttcacc atattggcca ggctggtctc caactcctaa tctcaggtga tctacccacc    1080
ttggcctccc aaattgctgg gattacaggc gtgaaccact gctcccttcc ctgtccttct    1140
gattttaaaa taactatacc agcaggagga cgtccagaca cagcataggc tacctggcca    1200
tgcccaaccg gtgggacatt tgagttgctt gcttggcact gtcctctcat gcgttgggtc    1260
cactcagtag atgcctgttg aattcgatac cgtcgacctc gagggggggc ccggtaccag    1320
cttttgttcc ctttagtgag ggttaatttc gagcttggcg taatcatggt catagctgtt    1380
tcctgtgtga aattgttatc cgctcacaat tccacacaac atacgagccg gaagcataaa    1440
gtgtaaagcc tggggtgcct aatgagtgag ctaactcaca ttaattgcgt tgcgctcact    1500
gcccgctttc cagtcgggaa acctgtcgtg ccagctgcat taatgaatcg gccaacgcgc    1560
```

```
ggggagaggc ggtttgcgta ttgggcgctc ttccgcttcc tcgctcactg actcgctgcg   1620
ctcggtcgtt cggctgcggc gagcggtatc agctcactca aaggcggtaa tacggttatc   1680
cacagaatca ggggataacg caggaaagaa catgtgagca aaaggccagc aaaaggccag   1740
gaaccgtaaa aaggccgcgt tgctggcgtt tttccatagg ctccgccccc ctgacgagca   1800
tcacaaaaat cgacgctcaa gtcagaggtg gcgaaacccg acaggactat aaagatacca   1860
ggcgtttccc cctggaagct ccctcgtgcg ctctcctgtt ccgaccctgc cgcttaccgg   1920
atacctgtcc gcctttctcc cttcgggaag cgtggcgctt tctcatagct cacgctgtag   1980
gtatctcagt tcggtgtagg tcgttcgctc caagctgggc tgtgtgcacg aaccccccgt   2040
tcagcccgac cgctgcgcct tatccggtaa ctatcgtctt gagtccaacc cggtaagaca   2100
cgacttatcg ccactggcag cagccactgg taacaggatt agcagagcga ggtatgtagg   2160
cggtgctaca gagttcttga agtggtggcc taactacggc tacactagaa gaacagtatt   2220
tggtatctgc gctctgctga agccagttac cttcggaaaa agagttggta gctcttgatc   2280
cggcaaacaa accaccgctg gtagcggtgg tttttttgtt tgcaagcagc agattacgcg   2340
cagaaaaaaa ggatctcaag aagatccttt gatcttttct acggggtctg acgctcagaa   2400
gaactcgtca agaaggcgat agaaggcgat gcgctgcgaa tcgggagcgg cgataccgta   2460
aagcacgagg aagcggtcag cccattcgcc gccaagctct tcagcaatat cacgggtagc   2520
caacgctatg tcctgatagc ggtccgccac acccagccgg ccacagtcga tgaatccaga   2580
aaagcggcca ttttccacca tgatattcgg caagcaggca tcgccatggg tcacgacgag   2640
atcctcgccg tcgggcatgc gcgccttgag cctggcgaac agttcggctg cgcgagccc   2700 ctgatgctct tcgtccagat catcctgatc gacaagaccg gcttccatcc gagtacgtgc   2760
tcgctcgatg cgatgtttcg cttggtggtc gaatgggcag gtagccggat caagcgtatg   2820
cagccgccgc attgcatcag ccatgatgga tactttctcg gcaggagcaa ggtgagatga   2880
caggagatcc tgccccggca cttcgcccaa tagcagccag tcccttcccg cttcagtgac   2940
aacgtcgagc acagctgcgc aaggaacgcc cgtcgtggcc agccacgata gccgcgctgc   3000
ctcgtcctgc agttcattca gggcaccgga caggtcggtc ttgacaaaaa gaaccgggcg   3060
cccctgcgct gacagccgga acacggcggc atcagagcag ccgattgtct gttgtgccca   3120
gtcatagccg aatagcctct ccacccaagc ggccggagaa cctgcgtgca atccatcttg   3180
ttcaatcatg cgaaacgatc ctcatcctgt ctcttgatca gatcttgatc ccctgcgcca   3240
tcagatcctt ggcggcaaga aagccatcca gtttactttg cagggcttcc caaccttacc   3300
agagggcgcc ccagctggca attccggttc gcttgctgtc cataaaaccg cccagtctag   3360
caactgttgg gaagggcgat cggtgcgggc ctcttcgcta ttacgccagc tggcgaaagg   3420
gggatgtgct gcaaggcgat taagttgggt aacgccaggg ttttcccagt cacgacgttg   3480
taaaacgacg gccagtgaat tgtaatacga ctcactatag ggcgaattgg agct          3534
```

```
<210> SEQ ID NO 34
<211> LENGTH: 2506
<212> TYPE: DNA
<213> ORGANISM: Artificial Sequence
<220> FEATURE:
<223> OTHER INFORMATION: Codon optimized mouse GHRH expression plasmid

<400> SEQUENCE: 34
ccaccgcggt ggcggccgtc cgccctcggc accatcctca cgacacccaa atatggcgac     60
gggtgaggaa tggtggggag ttattttag agcggtgagg aaggtgggca ggcagcaggt   120
```

```
gttggcgctc taaaaataac tcccgggagt tattttttaga gcggaggaat ggtggacacc    180
caaatatggc gacggttcct cacccgtcgc catatttggg tgtccgccct cggccggggc    240
cgcattcctg ggggcgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgctc    420
tttgtgatcc tcatcctcac cagcggcagc cactgcagcc tgcctcccag ccctcccttc    480
aggatgcaga ggcacgtgga cgccatcttc accaccaact acaggaagct gctgagccag    540
ctgtacgcca ggaaggtgat ccaggacatc atgaacaagc agggcgagag gatccaggag    600
cagagggcca ggctgagctg ataagcttat cggggtggca tccctgtgac ccctccccag    660
tgcctctcct ggccctggaa gttgccactc cagtgcccac cagccttgtc ctaataaaat    720
taagttgcat cattttgtct gactaggtgt ccttctataa tattatgggg tggaggggg     780 tggtatggag caaggggcaa gttgggaaga caacctgtag ggctcgaggg ggggcccggt    840
accatgtgag caaaaggcca gcaaaaggcc aggaaccgta aaaaggccgc gttgctggcg    900
tttttccata ggctccgccc ccctgacgag catcacaaaa atcgacgctc aagtcagagg    960
tggcgaaacc cgacaggact ataaagatac caggcgtttc ccccctggaag ctccctcgtg   1020 cgctctcctg ttccgaccct gccgcttacc ggatacctgt ccgcctttct cccttcggga   1080
agcgtggcgc tttctcatag ctcacgctgt aggtatctca gttcggtgta ggtcgttcgc   1140
tccaagctgg gctgtgtgca cgaaccccc gttcagcccg accgctgcgc cttatccggt    1200
aactatcgtc ttgagtccaa cccggtaaga cacgacttat cgccactggc agcagccact   1260
ggtaacagga ttagcagagc gaggtatgta ggcggtgcta cagagttctt gaagtggtgg   1320
cctaactacg gctacactag aagaacagta tttggtatct gcgctctgct gaagccagtt   1380
accttcggaa aaagagttgg tagctcttga tccggcaaac aaaccaccgc tggtagcggt   1440 ggttttttg tttacaagca gcagattacg cgcagaaaaa aaggatctca agaagatcct    1500
ttgatctttt ctacggggtc tgacgctcag ctagcgctca gaagaactcg tcaagaaggc   1560
gatagaaggc gatgcgctgc gaatcgggag cggcgatacc gtaaagcacg aggaagcggt   1620
cagcccattc gccgccaagc tcttcagcaa tatcacgggt agccaacgct atgtcctgat   1680
agcggtccgc cacacccagc cggccacagt cgatgaatcc agaaaagcgg ccattttcca   1740
ccatgatatt cggcaagcag gcatcgccat gagtcacgac gagatcctcg ccgtcgggca   1800
tgcgcgcctt gagcctggcg aacagttcgg ctggcgcgag cccctgatgc tcttcgtcca   1860
gatcatcctg atcgacaaga ccggcttcca tccgagtacg tgctcgctcg atgcgatgtt   1920
tcgcttggtg gtcgaatggg caggtagccg gatcaagcgt atgcagccgc cgcattgcat   1980
cagccatgat ggatactttc tcggcaggag caaggtgaga tgacaggaga tcctgccccg   2040
gcacttcgcc caatagcagc cagtcccttc ccgcttcagt gacaacgtcg agcacagctg   2100
cgcaaggaac gcccgtcgtg gccagccacg atagccgcgc tgcctcgtcc tgcagttcat   2160
tcagggcacc ggacaggtcg gtcttgacaa aaagaaccgg gcgcccctgc gctgacagcc   2220
ggaacacggc ggcatcagag cagccgattg tctgttgtgc ccagtcatag ccgaatagcc   2280
tctccaccca agcggccgga gaacctgcgt gcaatccatc ttgttcaatc atgcgaaacg   2340
atcctcatcc tgtctcttga tcagatcttg atccctgcg ccatcagatc cttggcggca   2400
agaaagccat ccagtttact ttgcagggct tcccaacctt accagagggc gccccagctg   2460
gcaattccgg ttcgcttgct gtccataaaa ccgcccagtc tgagct              2506
```

<210> SEQ ID NO 35
<211> LENGTH: 2725
<212> TYPE: DNA
<213> ORGANISM: Artificial Sequence
<220> FEATURE:
<223> OTHER INFORMATION: Codon optimized rat GHRH expression plasmid

<400> SEQUENCE: 35

```
ccaccgcggt ggcggccgtc cgccctcggc accatcctca cgacacccaa atatggcgac        60
gggtgaggaa tggtggggag ttatttttag agcggtgagg aaggtgggca ggcagcaggt       120
gttggcgctc taaaaataac tcccgggagt tattttaga gcggaggaat ggtggacacc       180
caaatatggc gacggttcct cacccgtcgc catatttggg tgtccgccct cggccggggc       240
cgcattcctg ggggccgggc ggtgctcccg cccgcctcga taaaaggctc cggggccggc       300
ggcggcccac gagctacccg gaggagcggg aggcgccaag cggatcccaa ggcccaactc       360
cccgaaccac tcagggtcct gtggacagct cacctagctg ccatggccct gtgggtgttc       420
ttcgtgctgc tgaccctgac cagcggaagc cactgcagcc tgcctcccag ccctcccttc       480
agggtgcgcc ggcacgccga cgccatcttc accagcagct acaggaggat cctgggccag       540
ctgtacgcta ggaagctcct gcacgagatc atgaacaggc agcagggcga gaggaaccag       600
gagcagagga gcaggttcaa ctgataagct tatcggggtg catccctgt gacccctccc        660
cagtgcctct cctggccctg aagttgcca ctccagtgcc caccagcctt gtcctaataa        720
aattaagttg catcattttg tctgactagg tgtccttcta taatattatg ggtggaggg        780
gggtggtatg gagcaagggg caagttggga agacaacctg tagggctcga ggggggccc        840
ggtaccagct tttgttccct ttagtgaggg ttaatttcga gcttggtctt ccgcttcctc        900
gctcactgac tcgctgcgct cggtcgttcg gctgcggcga cggtatcag ctcactcaaa        960
ggcggtaata cggttatcca cagaatcagg ggataacgca ggaaagaaca tgtgagcaaa       1020
aggccagcaa aaggccagga accgtaaaaa ggccgcgttg ctggcgtttt tccataggct       1080
ccgccccct gacgagcatc acaaaaatcg acgctcaagt cagaggtggc gaaacccgac       1140
aggactataa agataccagg cgtttccccc tggaagctcc ctcgtgcgct ctcctgttcc       1200
gaccctgccg cttaccggat acctgtccgc ctttctccct tcgggaagcg tggcgctttc       1260
tcatagctca cgctgtaggt atctcagttc ggtgtaggtc gttcgctcca agctgggctg       1320
tgtgcacgaa ccccccgttc agcccgaccg ctgcgcctta ccggtaact atcgtcttga       1380
gtccaacccg gtaagacacg acttatcgcc actggcagca gccactggta acaggattag       1440
cagagcgagg tatgtaggcg gtgctacaga gttcttgaag tggtggccta actacggcta       1500
cactagaaga acagtatttg gtatctgcgc tctgctgaag ccagttacct tcggaaaaag       1560
agttggtagc tcttgatccg gcaaacaaac caccgctggt agcggtggtt ttttgttta       1620
caagcagcag attacgcgca gaaaaaagg atctcaagaa gatcctttga tcttttctac       1680
ggggtctgac gctcagctag cgctcagaag aactcgtcaa gaaggcgata gaaggcgatg       1740
cgctgcgaat cgggagcggc gataccgtaa agcacgagga gcggtcagc ccattcgccg       1800
ccaagctctt cagcaatatc acgggtagcc aacgctatgt cctgatagcg gtccgccaca       1860
cccagccggc cacagtcgat gaatccagaa agcggccat tttccaccat gatattcggc       1920
aagcaggcat cgccatgagt cacgacgaga tcctcgccgt cgggcatgcg cgccttgagc       1980
ctggcgaaca gttcggctgg cgcgagcccc tgatgctctt cgtccagatc atcctgatcg       2040
acaagaccgg cttccatccg agtacgtgct cgctcgatgc gatgtttcgc ttggtggtcg       2100
```

```
aatgggcagg tagccggatc aagcgtatgc agccgccgca ttgcatcagc catgatggat    2160
actttctcgg caggagcaag gtgagatgac aggagatcct gccccggcac ttcgcccaat    2220
agcagccagt cccttcccgc ttcagtgaca acgtcgagca cagctgcgca aggaacgccc    2280
gtcgtggcca gccacgatag ccgcgctgcc tcgtcctgca gttcattcag ggcaccggac    2340
aggtcggtct tgacaaaaag aaccgggcgc ccctgcgctg acagccggaa cacggcggca    2400
tcagagcagc cgattgtctg ttgtgcccag tcatagccga atagcctctc cacccaagcg    2460 gccgagaac  ctgcgtgcaa tccatcttgt tcaatcatgc gaaacgatcc tcatcctgtc    2520
tcttgatcag atcttgatcc cctgcgccat cagatccttg gcggcaagaa agccatccag    2580
tttactttgc agggcttccc aaccttacca gagggcgccc cagctggcaa ttccggttcg    2640
cttgctgtcc ataaaaccgc ccagtctagc aactgttggg aagggcgatc gtgtaatacg    2700
actcactata gggcgaattg gagct                                          2725
```

GROWTH HORMONE RELEASING HORMONE TREATMENT TO DECREASE CHOLESTEROL LEVELS

CROSS-REFERENCE TO RELATED APPLICATIONS

This application is a US National Stage under 35 U.S.C. §371 of International Application No. PCT/US2007/072851 (filed Jul. 5, 2007) that claims priority under 35 U.S.C. Section 119(e) to Application No. 60/810,013 filed on Jul. 6, 2006.

BACKGROUND

This invention is related to compositions and methods for decreasing the cholesterol levels in a subject. More specifically, the invention pertains to delivering a nucleic acid expression construct that encodes growth-hormone-releasing-hormone ("GHRH") into a tissue of the subject, wherein, GHRH is expressed in vivo in the subject, and has the effect of decreasing the cholesterol levels in that subject. The subject for this invention can be a human, pig, cow, bird or any other animal species.

High cholesterol level remains a significant problem in both humans and animals. Recent data from the American Medical Association shows that 30% of the entire population of the US is obese, including children, and at risk at developing pathologies induced in part by high cholesterol levels such as heart disease. Thus, cholesterol-decreasing therapies are required. Substantial efforts have addressed the prevention rather than treatment of disease. Hypothalamic GHRH stimulates growth hormone ("GH") secretion from the anterior pituitary gland, but recent studies have also demonstrated other properties of this peptide (Siejka et al., 2004).

Cholesterol. Cholesterol is a sterol (a combination steroid and alcohol) and a lipid found in the cell membranes of all body tissues, and transported in the blood plasma of all animals. Lesser amounts of cholesterol are also found in plant membranes.

Most cholesterol in animals is NOT dietary in origin and is synthesized internally. Cholesterol is present in higher concentrations in tissues which either produce more or have more densely-packed membranes, for example, the liver, spinal cord and brain, and also in atheromas. Cholesterol plays a central role in many biochemical processes, but is best known for the association of cardiovascular disease with various lipoprotein cholesterol transport patterns and high levels of cholesterol in the blood.

Often, when most doctors talk to their patients about the health concerns of cholesterol, they are referring to "bad cholesterol", or low-density lipoprotein (LDL). "Good cholesterol" is high-density lipoprotein (HDL).

Cholesterol is required to build and maintain cell membranes and makes the membrane's fluidity stable over wider temperature intervals. This is possible due to the hydroxyl group on cholesterol that interacts with the phosphate head of the membrane, and the bulky steroid and the hydrocarbon chain being embedded in the membrane. Some research indicates that cholesterol may act as an antioxidant. Cholesterol also aids in the manufacture of bile (which helps digest fats), and is also important for the metabolism of fat soluble vitamins, including vitamins A, D, E and K. Cholesterol is the major precursor for the synthesis of vitamin D, of the various steroid hormones, including cortisol and aldosterone in the adrenal glands, and of the sex hormones progesterone, estrogen, and testosterone. Further recent research shows that cholesterol has an important role for the brain synapses as well as in the immune system, including protecting against cancer.

Recently, cholesterol has also been implicated in cell signaling processes, where it has been suggested that it forms lipid rafts in the plasma membrane. It also reduces the permeability of the plasma membrane to proton and sodium ions. Cholesterol is minimally soluble in water, therefore, it cannot dissolve and travel in the water-based bloodstream. Instead, cholesterol is transported in the bloodstream by lipoproteins that are water-soluble and carry cholesterol and fats internally. The proteins forming the surface of the given lipoprotein particle determine from what cells cholesterol will be removed and to where it will be supplied.

The largest lipoproteins are called chylomicrons, and function to primarily transport fats from the intestinal mucosa to the liver. They carry mostly triglyceride fats and cholesterol. In the liver, chylomicron particles give up triglycerides and some cholesterol, and are converted into low-density lipoprotein (LDL) particles, which carry triglycerides and cholesterol on to other body cells. In healthy individuals the LDL particles are large and relatively few in number. In contrast, large numbers of small LDL particles are strongly associated with promoting disease within the arteries.

High-density lipoprotein (HDL) particles transport cholesterol back to the liver for excretion, but vary considerably in their effectiveness for doing this. Having large numbers of large HDL particles correlates with better health outcomes. In contrast, having small amounts of large HDL particles is strongly associated with disease progression within the arteries.

The cholesterol molecules present in LDL cholesterol and HDL cholesterol are identical. The difference between the two types of cholesterol derives from the carrier protein molecules or the lipoprotein component.

Biosynthesis of cholesterol is directly regulated by the cholesterol levels present, though the homeostatic mechanisms involved are only partly understood. A higher intake from food leads to a net decrease in endogenous production, while lower intake from food has the opposite effect. Although not wanting to be bound by theory, the main regulatory mechanism is the sensing of intracellular cholesterol in the endoplasmic reticulum by the protein SREBP (Sterol Regulatory Element Binding Protein 1 and 2). In the presence of cholesterol, SREBP is bound to two other proteins: SCAP (SREBP-cleavage activating protein) and Insig-1. When cholesterol levels fall, Insig-1 dissociates from the SREBP-SCAP complex, allowing the complex to migrate to the Golgi apparatus, where SREBP is cleaved by S1P and S2P (site 1/2 protease), two enzymes that are activated by SCAP when cholesterol levels are low. The cleaved SREBP then migrates to the nucleus and acts as a transcription factor to bind to the SRE (sterol regulatory element) of a number of genes to stimulate their transcription. Among the genes transcribed are the LDL receptor and HMG-CoA reductase. The former scavenges circulating LDL from the bloodstream, whereas HMG-CoA reductase leads to an increase of endogenous production of cholesterol. An excess of cholesterol in the bloodstream may lead to its accumulation in the walls of arteries. This build up is what can lead to clogged arteries and eventually to heart attacks and strokes.

The average amount of blood cholesterol varies with age, typically rising gradually until one is about 60 years old. There appear to be seasonal variations in cholesterol levels in humans, more, on average, in winter.

Cholesterol is excreted from the liver in bile and reabsorbed from the intestines. Under certain circumstances, when more concentrated, as in the gallbladder, it crystallises and is the major constituent of most gallstones, although lecithin and bilirubin gallstones also occur less frequently.

Growth hormone ("GH") secretion has been shown to decline during aging, and studies have indicated that GH alters plasma cholesterol (PC) concentrations. For example, a study was conducted to determine how GH secretagogues affect age-related hypercholesterolemia (Walker et al., 1994). In this study, animals were co-administered (s.c.) growth hormone releasing hormone ("GHRH") and GH-releasing hexapeptide. This study showed that aging was associated with a progressive increase in PC, which was reduced in animals administered GHRH and GHRP compared to those administered vehicle. The results suggest that reduced GH secretion during aging contributes to a progressive increase in plasma cholesterol that can be partially prevented with GH-secretagogues.

Additionally, both growth hormone ("GH") and insulin-like growth factor I (IGF-I) are involved in heart development and in maintenance of cardiac structure and performance. Cardiovascular disease has been reported to reduce life expectancy in both GH deficiency ("GHD") and GH excess. Patients with GHD suffer from a cluster of abnormalities associated with increased cardiovascular risk, including abnormal body composition, unfavorable lipid profile, increased fibrinogen and C-reactive protein levels, insulin resistance, early atherosclerosis and endothelial dysfunction, and impaired left ventricular (LV) performance (i.e., reduced diastolic filling and impaired response to peak exercise). Long-term GH replacement therapy reverses most of these abnormalities. More consistently, OH replacement reduces body fat and visceral adipose tissue, reduces low-density lipoprotein cholesterol and triglyceride levels, and improves endothelial function. GH replacement also reduces intima media thickness at major arteries and improves LV performance, but these results have been observed only in small series of patients treated on a short-term basis. This review discusses the roles of GHD and GH replacement therapy in the development of cardiovascular disease (Colao et al., 2006).

Growth Hormone Releasing Hormone ("GHRH") and Growth Hormone ("GH") Axis: To better understand how GHRH plasmid-mediated supplementation can be used as a method to decrease cholesterol levels in a subject, the mechanisms and current understanding of the GHRH axis will be addressed. Although not wanting to be bound by theory, the central role of GH is controlling somatic growth in humans and other vertebrates. The physiologically relevant pathways regulating GH secretion from the pituitary are fairly well known. The GH pathway genes include: (1) ligands, such as GH and insulin-like growth factor I ("IGF-I"); (2) transcription factors such as prophet of pit-1 (prop-1), and pit-1: (3) agonists and antagonists, such as GHRH and somatostatin ("SS"), respectively; and (4) receptors, such as GHRH receptor ("GHRH-R") and the GH receptor ("GH-R").

These genes are expressed in different organs and tissues, including the hypothalamus, pituitary, liver, and bone. Effective and regulated expression of the GH pathway is essential for optimal linear growth, as well as homeostasis. GH synthesis and secretion from the anterior pituitary is stimulated by GHRH and inhibited by somatostatin, both hypothalamic hormones. GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

Supplementation of endogenous GH with injections of recombinant GH peptide has been demonstrated to improve linear growth and/or lean body mass accretion in both animals (Chung et al., 1985; Etherton et al., 1987) and humans (Boguszewski et al., 2005; Lissett and Shalet, 2000). Although this practice is effective, its prolonged use has been linked to some adverse effects including impaired glucose tolerance (Bramnert et al., 2003), fluid retention (Verhelst et al., 1997), and carpal tunnel syndrome (Cummings and Merriam, 1999; Zachwieja and Yarasheski, 1999).

GH secretagogues, especially GHRH, have been considered as an alternative approach to the use of GH either to promote growth or for treatment of conditions that may benefit from activation of the GH/IGF-I axis (Ehlers, 2001). There are several advantages to the use of GHRH: it can stimulate the pulsatile release of endogenous GH (Clark and Robinson, 1985); the feedback control of endogenous GH (Clark et al., 1988) and IGF-I (Ceda et al., 1987) is preserved over a significant dose range, thereby guarding against imbalances between GH and IGF-I levels; the incidence of adverse effects are uncommon (Duck and Rapaport, 1999). Also, GHRH stimulates all GH isoforms, which have been shown to have differential effects in normal and pathological circumstances (Fujikawa et al., 2000; Wallace et al., 2001). Ghrelin is also able to stimulate GH release through its GH-secretagogue receptor (Sun et al., 2004) and has been shown to have a potent impact on fat metabolism (Dornonville de la et al., 2005) and body composition as a potential treatment for cachexia (Nagaya et al., 2005); nevertheless, ghrelin has been reported to stimulate food intake, increase weight gain, and cause obesity (Dornonville de la et al., 2005).

In animals, the short-term or chronic administration of GHRH, either as the recombinant protein or as an analog, improves growth and carcass quality of swine (Phung et al., 2000; Pommier et al., 1990), and lactation performance in dairy cattle (Auchtung et al., 2001; Dahl et al., 1991), but without incurring the side-effects associated with GH. Therapeutic areas also are being investigated for humans for the improvement in body composition in patients with pathological situations, e.g., cachexia (Kotler, 2000), advanced HIV/AIDS (Mulligan and Schambelan, 2002) or cardiac failure (Colao et al., 1999). However, the short half-life of the GHRH peptide in serum (approximately 6 minutes) necessitates injections 1 to 3 times a day, which renders the use of GHRH peptide impractical, especially for long term applications. Plasmid-based GHRH administration is an alternative approach that eliminates the need for repeated administrations of the GHRH peptide or other GH secretagogues.

Previous studies from our laboratory have demonstrated that injection and electroporation of a single dose of a muscle-specific expression plasmid encoding for a GHRH analog cDNA (HV-GHRH) with a longer half-life effectively increased GH and IGF-I concentrations, and improved feed efficiency and weight gain over a 56-day period in swine (Draghia-Akli et al., 1999). In healthy young dogs (Draghia-Akli et al., 2003a), the treatment increased plasma IGF-I levels, body weight, and improved hematological parameters, while maintaining these parameters within the normal limits. In geriatric and cancer-afflicted dogs, plasmid GHRH corrected anemia and cachexia associated with cancer and its therapies (Draghia-Akli et al., 2002a), improved immune function, quality of life and activity levels and furthermore, these effects were maintained long-term after a single administration of the plasmid (Tone et al., 2004).

Growth Hormone Releasing Hormone versus Growth Hormone or Growth Hormone Releasing Peptides ("GHRP"): GH and GHRH are currently administered therapeutically as recombinant proteins. Levels of total cholesterol, triglyceride, free fatty acid, fibrinogen and plasminogen activator inhibitor-1 are decreasing in some patients with GH-deficiencies or high atherosclerotic risk after GH treatment (Ahn et al., 2006; Bollerslev et al., 2005). On the other hand, ghrelin, an upstream stimulator of GH secretion, increases fat deposition, and is positively correlated with cholesterol levels (Langenberg et al., 2005). The effects of GHRH as an unique treatment on cholesterol levels have been unknown to date.

Current knowledge about the interaction between GH and its receptor suggests that the molecular heterogeneity of circulating GH may have important homeostasis implications. It has been suggested that adverse effects including insulin resistance, may result from the fact that exogenous OH elevates the basal GH serum levels and abolishes the natural GH episodic pulses. Studies have shown that continuous infusion with GHRH restores normal GH pulsatile pattern, without desensitization of GHRH receptors or depletion of GH supplies in humans, sheep or pigs (Dubreuil et al., 1990; Vance et al., 1985; Vance et al., 1989). At the same time, this system is capable of feed-back, which is totally abolished in the GH therapies. Virtually no side effects have been reported for GHRH therapies (Thorner et al., 1986a). Thus, GHRH therapy may be more physiological than GH therapy.

GHRPs are used in clinics to stimulate short term GH and IGF-I in humans. Hexarelin, a potent and well-studied GHRP, is capable of causing profound GH release in normal individuals. The GH response to hexarelin in humans becomes appreciably attenuated following long-term administration. Although this attenuation is partial and reversible, it could seriously limit the potential long-term therapeutic use of hexarelin and similar agents (Rahim and Shalet, 1998). With the development of GH-releasing agents and their use in human subjects, it is clear that these agents are not specific for GH release. More recent studies in humans have demonstrated that acute increases in adrenocorticotrophic hormone (ACTH) (Ghigo et al., 1999), cortisol and prolactin (PRL) (Svensson and Bengtsson, 1999) have occurred after administration of GHRPs (hexarelin, MK-0677) (Schleim et al., 1999). The potential adverse effects of repeated episodes of transient (even minor) hyperprolactinaemia and hypercortisolaemia during long-term therapy with GHRPs and similar agents raise concern, require further study, and are undesirable in patients with high cholesterol levels.

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (Esch et al., 1982; Thorner et al., 1984), when the overexpression persists for more than 7 years. Although recombinant GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical.

Transgene Delivery and in vivo Expression: Although not wanting to be bound by theory, the delivery of a specific transgene to somatic tissue to correct inborn or acquired deficiencies and imbalances is possible. Such transgene-based delivery offers a number of advantages over the administration of recombinant proteins. These advantages include: the conservation of native protein structure; improved biological activity; avoidance of systemic toxicities; and avoidance of infectious and toxic impurities. Because the protein is synthesized and secreted continuously into the circulation by the subject's own cells, plasmid-mediated therapy allows for prolonged production of the protein in a therapeutic range. In contrast, the primary limitation of using recombinant protein is the limited bio-availability of protein after each administration.

A non-viral, plasmid-based expression system, may comprise of a synthetic transgene delivery system in addition to the nucleic acid encoding the therapeutic genetic product. In this way, the risks associated with the use of most viral vectors can be avoided, including the expression of viral proteins that can induce immune responses against the target tissues or the viral vector and the possibility of DNA mutations or activations of oncogenes. The non-viral expression vector products generally have low toxicity due to the use of "species-specific" components for gene delivery, which minimizes the risks of plasmid-targeted immunogenicity and loss of expression. Additionally, no significant integration of plasmid sequences above the rate of spontaneous mutation into host chromosomes has been reported in vivo to date, so that this type of therapy should neither activate oncogenes nor inactivate tumor suppressor genes. As episomal systems residing outside the chromosomes, plasmids have defined pharmacokinetics and elimination profiles, leading to a finite duration of gene expression in target tissues. Plasmid vectors are simple to manufacture using good manufacturing practice techniques. They have a low risk to benefit ratio when compared to viral vectors, as stated on Mar. 13-14, 2003 in a workshop sponsored by the American Society of Gene Therapy (ASGT) and the Food and Drug Administration's Center for Biologics Evaluation and Research (FDA/CBER) (Frederickson et al., 2003).

Direct plasmid DNA gene transfer is currently the basis of many emerging nucleic acid therapy strategies and does not require viral components or lipid particles (Aihara and Miyazaki, 1998; Muramatsu et al., 2001). Skeletal muscle is a preferred target tissue, because muscle fiber has a long life span and can be transduced by circular DNA plasmids that are expressed in immunocompetent hosts (Davis et al., 1993; Tripathy et al., 1996). Plasmid DNA constructs are attractive candidates for direct therapy into the subjects skeletal muscle because the constructs are well-defined entities that are biochemically stable and have been used successfully for many years (Acsadi et al., 1991; Wolff et al., 1990). The relatively low expression levels of an encoded product that are achieved after direct plasmid DNA injection are sometimes sufficient to indicate bio-activity of secreted peptides (Danko and Wolff, 1994; Tsurumi et al., 1996). Our previous reports in mice showed that a human GHRH cDNA could be delivered by direct injection into the muscle by a plasmid where it transiently stimulated GH secretion to a modest extent over a short period (Draghia-Akli et al., 1997).

Plasmid delivery and electroporation: Efforts have been made to enhance the delivery of plasmid DNA to cells by physical means including electroporation, sonoporation, and hydrodynamic pressure. In various tissues, transfection has been enhanced or accomplished by: 1) "gene gun" delivery (usually DNA-coated gold particles propelled into cells); 2) jet injection of DNA (e.g., Biojector); 3) hydrodynamic (intravascular) methods; and 4) by cationic agents such as linear or branched polymers (e.g., polyethylenimines [PEIs]) or cationic liposomes (Akhtar, 2005; El-Aneed, 2004; Patil et al., 2005; Wells, 2004). These methods have their own drawbacks. Gene gun delivery is limited to exposed tissues, intravascular methods often require injection of large volumes of fluid that are not applicable to humans, while complexes of DNA and cationic lipids or polymers can be unstable, inflammatory and even toxic. One of the most versatile and efficient methods of enhancing gene transfer involves the application of electric field pulses after the injection of nucleic acids (DNA, RNA and/or oligonucleotides) into tissues. Although not wanting to be bound by theory, the administration of a nucleic acid construct by electroporation involves the application of a pulsed electric field to create transient pores in the cellular membrane without causing permanent damage to the cell, which allows exogenous molecules to enter the cell (Prud'homme et al., 2006). Nucleic acid molecules may travel through passageways or pores in the cell that are created during the procedure. U.S. Pat. No. 5,704,908 titled "Electroporation and iontophoresis catheter with porous balloon," issued on Jan. 6, 1998 with Hofmann et al., listed as inventors describes an constant voltage electroporation apparatus for delivering molecules to cells at a selected location within a cavity in the body of a patient. Similar pulse voltage injection devices are also described in: U.S. Pat. No. 5,702,359 titled "Needle electrodes for mediated delivery of drugs and genes," issued on Dec. 30, 1997, with Hofmann, et al., listed as inventors; U.S. Pat. No. 5,439,440 titled "Electroporation system with voltage control feedback for clinical applications," issued on Aug. 8, 1995 with Hofmann listed as inventor; PCT application WO/96/12520 titled "Electroporetic Gene and Drug Therapy by Induced Electric Fields," published on May 5, 1996 with Hofmann et al., listed as inventors; PCT application WO/96/12006 titled "Flow Through Electroporation Apparatus and Method," published on Apr. 25, 1996 with Hofmann et al., listed as inventors; PCT application WO/95/19805 titled "Electroporation and Iontophoresis Apparatus and Method For insertion of Drugs and genes into Cells," published on Jul. 27, 1995 with Hofmann listed as inventor; and PCT application WO/97/07826 titled "In Vivo Electroporation of Cells," published on Mar. 6, 1997, with Nicolau et al., listed as inventors, the entire content of each of the above listed references is hereby incorporated by reference.

Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Previous studies using GHRH showed that plasmid therapy with electroporation is scalable and represents a promising approach to induce production and regulated secretion of proteins in large animals and humans (Draghia-Akli et al., 1999; Draghia-Akli et al., 2002c). Intramuscular injection of plasmid followed by electroporation has been used successfully in ruminants for vaccination purposes (Babiuk et al., 2003; Tollefsen et al., 2003). It has been observed that the electrode configuration affects the electric field distribution, and subsequent results (Gehl et al., 1999; Miklavcic et al., 1998). Although not wanting to be bound by theory, needle electrodes give consistently better results than external caliper electrodes in a large animal model, and can be used for humans. U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

Constant current versus constant voltage electroporation and species differences: To better understand the process of electroporation, it is important to look at some simple equations. When a potential difference (voltage) is applied across the electrodes implanted in a tissue, it generates an electric field ("E"), which is the applied voltage ("V") divided by the distance ("d") between the electrodes: E=V/d The electric field intensity E has been a very important value when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. The flow of electric charge (current) between electrodes is achieved by the buffer ions in the tissues, which can vary among tissues and patients. Furthermore, the flow of conducting ions can change between electrodes from the beginning of the electric pulse to the end of the electric pulse. When tissues have a small proportion conducting ions, resistance is increased, heat is generated and cells are killed. Ohm's law expresses the relationship between current ("I"), voltage ("V"), and resistance ("R"): R=V/I Heating is the product of the inter-electrode impedance (i.e. combination of resistance and reactance and is measured in ohms), and is proportional to the product of the current, voltage and pulse duration. Heating can also be expressed as the square of the current, and pulse duration ("t", time). For example, during electroporation the heating or power ("W", watts) generated in the supporting tissue can be represented by the following equation; $W=I^2Rt$.

During pulses, specific tissue resistance may drop (Zampaglione et al., 2005), and the same voltage which did not cause significant heating during the first pulse can burn the tissue during the second (the equation $W=V^2t/R$ illustrates this undesirable effect). Constant current EP prevents this overheating, but constant-voltage techniques do not take into account the individual and changing resistance of the tissue and can result in tissue damage, inflammation, and loss of plasmid expression. Recently, we have used instead constant current EP, which we refer to as electrokinetic enhancement. Thus, we have used a software-driven constant-current electroporator denoted electrokinetic device (EKD device) to deliver plasmids to small and large animals (Brown et al., 2004; Draghia-Akli and Fiorotto, 2004; Khan et al., 2005). The most favorable conditions of electroporation were dependent on the individual tissue resistance, which varies by age and species. We found that EP-induced tissue injury can be reduced or eliminated by applying optimal constant current instead of constant voltage. Indeed, this prevents tissue heating and cell death, such as frequently occurs with constant voltage technology and is most relevant to gene therapy in large animals.

The ability of electroporation to enhance plasmid uptake into the skeletal muscle has been well documented. Similarly, plasmids formulated with poly-L-glutamate ("PLG") or polyvinylpyrrolidone ("PVP") were observed to have an increase in plasmid transfection, which consequently increased the expression of a desired transgene. For example, plasmids formulated with PLG or PVP were observed to increase gene expression to up to 10 fold in the skeletal muscle of mice, rats, and dogs (Fewell et al., 2001; Mumper et al., 1998). Nevertheless, in these cases, expression was short lived and correlated with tissue damage. Although not wanting to be bound by theory, the anionic polymer sodium PLG enhances plasmid uptake at low plasmid concentrations and may reduce any possible tissue damage caused by the procedure if of a certain molecular weight and concentration (Draghia-Akli et al., 2002b). PLG is a stable compound and it is resistant to relatively high temperatures (Dolnik et al., 1993). PLG has been used to increase stability of anti-cancer drugs (Li et al., 2000) and as "glue" to close wounds or to prevent bleeding from tissues during wound and tissue repair (Otani et al., 1996; Otani et al., 1998). PLG also has been used as an anti-toxin after antigen inhalation or exposure to ozone (Fryer and Jacoby, 1993).

Although not wanting to be bound by theory, we have demonstrated PLG increases the transfection of the plasmid during the electroporation process, not only by stabilizing the plasmid DNA and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002b) and will increase plasmid stability in vitro prior to injection.

Although not wanting to be bound by theory, a GHRH cDNA can be delivered to muscle of mice injectable myogenic expression vector where it can transiently stimulate GH secretion over a period of two weeks (Draghia-Akli et al., 1997). This injectable vector system was optimized by incorporating a powerful synthetic muscle promoter (Li et al., 1999) coupled with a novel protease-resistant GHRH molecule with a substantially longer half-life and greater GH secretory activity (pSP-HV-GHRH) (Draghia-Akli et al., 1999). Highly efficient electroporation was optimized to deliver the nucleic acid construct to the skeletal muscle of an animal (Prud'homme et al., 2006). Using this combination of vector design and electric pulses plasmid delivery method, the inventors were able to show increased growth and favorably modified body composition in pigs (Draghia-Akli et al., 1999; Draghia-Akli et al., 2003b). The modified GHRH nucleic acid constructs increased red blood cell production in companion animals with cancer and cancer treatment-associated anemia (Draghia-Akli et al., 2002a). In pigs, available data suggested that the modified porcine HV-GHRH analog (SEQ ID#1) was more potent in promoting growth and positive body composition changes than the wild-type porcine GHRH (Draghia-Akli et al., 1999).

Administering novel GHRH analog proteins (U.S. Pat. Nos. 5,847,066; 5846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833, 166; 4,228,158; 4,228,156; 4,226,857; 4,224,316; 4,223,021; 4,223,020; 4,223,019) for the purpose of increasing release of growth hormone have been reported. A GHRH analog containing the following mutations has been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. Pat. No. 6,551,996 titled "Super-active porcine growth hormone releasing hormone analog," issued on Apr. 22, 2003 with Schwartz, et al., listed as inventors ("the '996 patent"), which teaches application of a GHRH analog containing mutations that improve the ability to elicit the release of growth hormone. In addition, the '996 patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

In summary, decreasing the cholesterol levels in a subject was previously uneconomical and restricted in scope. The related art has shown that it is possible to impact this condition in a limited capacity utilizing recombinant protein technology, but these treatments have some significant drawbacks. It has also been taught that nucleic acid expression constructs that encode recombinant proteins are viable solutions to the problems of frequent injections and high cost of traditional recombinant therapy. There is a need in the art to expanded treatments for subjects with a disease by utilizing nucleic acid expression constructs that are delivered into a subject and express stable therapeutic proteins in vivo.

SUMMARY

One aspect of the current invention includes compositions and methods of decreasing cholesterol levels into a subject. Specific embodiments of the invention pertain to delivering into a tissue of the subject a nucleic acid expression construct that encodes a growth-hormone-releasing-hormone ("GHRH"), wherein the GHRH is expressed in vivo in the subject and the subject comprises a human, pig, cow, bird, horse or any other animal species.

Other specific embodiments of this invention encompass various modes of delivering into the tissue of a subject the nucleic acid expression construct (e.g. an electroporation method, in conjunction with a carrier, by parenteral route, or a combination thereof). In a first preferred embodiment, the nucleic acid expression construct is delivered via an electroporation method comprising: a) penetrating the tissue in the subject with a plurality of needle electrodes, wherein the plurality of needle electrodes are arranged in a spaced relationship; b) introducing the nucleic acid expression construct into the tissue between the plurality of needle electrodes; and c) applying an electrical pulse to the plurality of needle electrodes. A second preferred embodiment includes the nucleic acid expression construct being delivered in a single dose, and the single dose comprising a total of about a 0.05-5 mg of nucleic acid expression construct. Generally the nucleic acid expression construct is delivered into a tissue of the subject comprising diploid cells (e.g. muscle cells). In a third specific embodiment the nucleic acid expression construct used for transfection comprises a wt-porcine-GHRH plasmid, pAV0242 (SEQ ID NO:25). Other specific embodiments utilize other nucleic acid expression constructs (e.g. an optimized bovine GHRH plasmid, pAV0236 (SEQ ID NO:27); a TI-GHRH plasmid, pAV0239 (SEQ ID NO:29); HV-GHRH plasmid, pAV0224 (SEQ ID NO:24); ovine GHRH plasmid, pAV0240 (SEQ ID NO:30); chicken GHRH plasmid, pAV0241 (SEQ ID NO:31); dog GHRH plasmid, pAV0235 (SEQ ID NO:26); cat GHRH plasmid, pAV0238 (SEQ ID NO:28); horse GHRH plasmid, pAV0249 ; human GHRH plasmid, pAV0243 (SEQ ID NO:32), mouse GHRH plasmid, pAV0248 (SEQ ID NO:34); or rat GHRH plasmid, pAV0218 (SEQ ID NO:35). In a fourth specific embodiment, the nucleic acid expression construct further comprises, a transfection-facilitating polypeptide (e.g. a charged polypeptide, or poly-L-glutamate). After delivering the nucleic acid expression construct into the tissues of the subject, expression of the encoded GHRH or functional biological equivalent thereof is initiated. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQ ID#14). The animal comprises a human, a food animal, a work animal (e.g. a pig, cow, sheep, goat or chicken), a farm animal, or a pet (e.g. horse, dog, cat).

BRIEF DESCRIPTION OF THE DRAWINGS

FIG. 2 shows the average daily composition of the weight gain from day 4 to day 52 of the study. There was a significant Study effect (P<0.001) for each variable, but no Study×Treatment interaction. Values are least square means±SEM. Values in the same row with different superscripts are significantly different (P<0.05).

FIG. 3 shows the body composition of pigs after 50 days of treatment with a single control plasmid, a porcine GHRH-expressing plasmid, or daily injections of porcine GH. There was a significant Study effect (P<0.001) for each variable, but no Study×Treatment interaction. Values are least square means±SEM. Values in the same row with different superscripts are significantly different (P<0.05).

FIG. 4 shows serum hormone concentrations measured at selected days of treatment. The data for day 0 were pooled. Values are least square means±SEM. Values in the same row with different superscript are significantly different.

FIG. 5 shows serum biochemistry measurements at the end of the study. Values are least square means±SEM. Values in the same row with different superscript are significantly different.

DETAILED DESCRIPTION OF THE PREFERRED EMBODIMENTS

Figure 1:
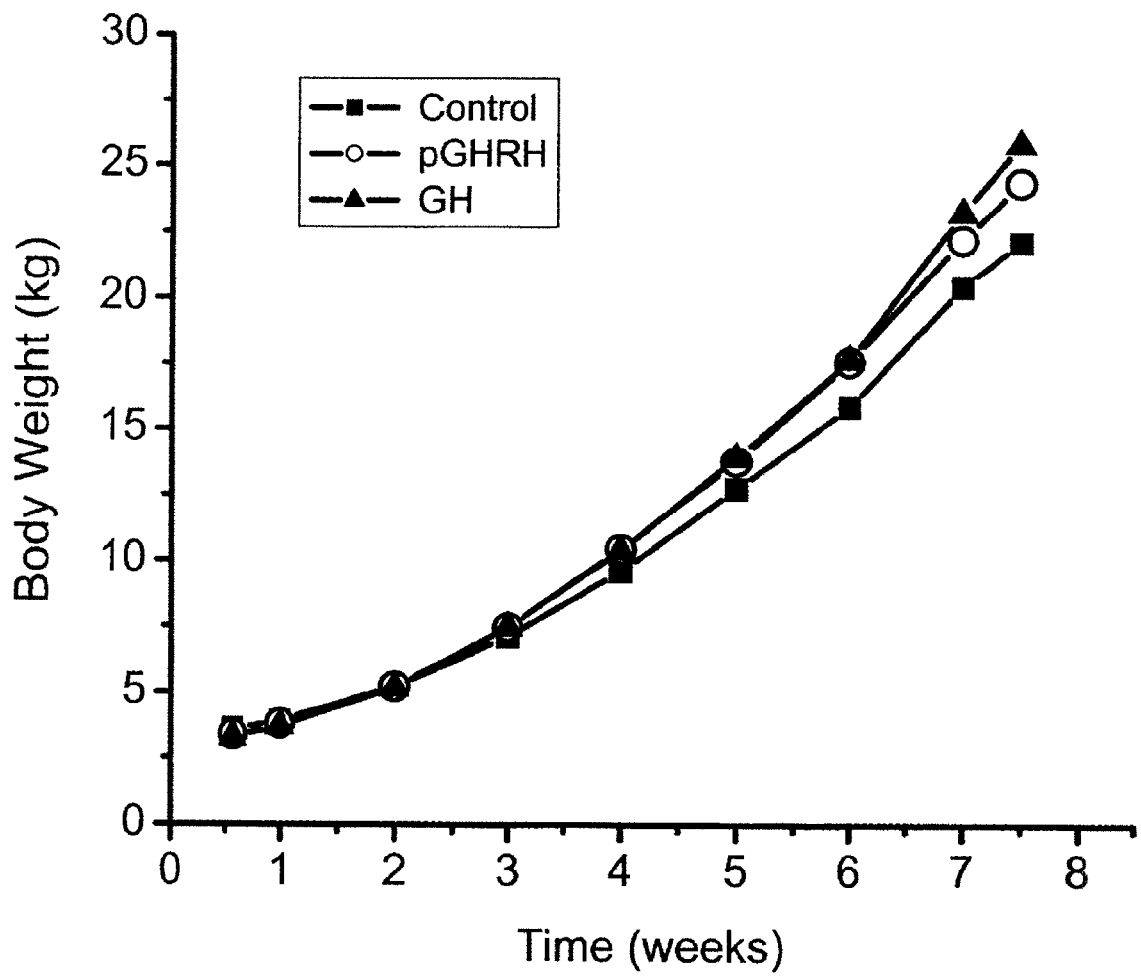
FIG. 1 shows the increases in body weight among the groups for the duration of the study. At approximately four weeks of age, the weights become divergent comparing the GH-injected and porcine wild-type GHRH animals to controls. From seven to eight weeks of age, weight gain in the porcine wild-type GHRH group is between GH and control animals.

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "analog" as used herein includes any mutant of GHRH, or synthetic or naturally occurring peptide fragments of GHRH, such as HV-GHRH (SEQ ID#1), pig-GHRH (SEQ ID#2), bovine-GHRH (SEQ ID#3), dog-GHRH (SEQ ID#4), cat-GHRH (SEQ ID#5), TI-GHRH (SEQ ID#6), ovine-GHRH (SEQ ID#7), chicken-GHRH (SEQ ID#8), horse-GHRH (SEQ ID#9), TV-GHRH (SEQ ID#11), TA-GHRH (SEQ ID#12), human GHRH (1-44)NH$_2$ (SEQ ID#13), human GHRH(1-40)OH (SEQ ID#10) forms, or any shorter form to no less than (1-29) amino acids.

The term "bodily fat proportion" as used herein is defined as the body fat mass divided by the total body weight.

The term "cassette" as used herein is defined as one or more expression sequences, comprising essentially a promoter, a transgene sequence and a 3' polyadenylation and/or 3' untranslated region.

The term "cell-transfecting pulse" as used herein is defined as a transmission of a force which results in transfection of a vector, such as a DNA fragment, into a cell. In some embodiments, the force is from electricity, as in electroporation, or the force is from vascular pressure.

The term "coding region" as used herein refers to any portion of the DNA sequence that is transcribed into messenger RNA (mRNA) and then translated into a sequence of amino acids characteristic of a specific polypeptide.

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "chronically ill" as used herein is defined as patients with conditions as chronic obstructive pulmonary disease, chronic heart failure, stroke, dementia, rehabilitation after hip fracture, chronic renal failure, arthritis, rheumatoid arthritis, and multiple disorders in the elderly, with doctor visits and/or hospitalization once a month for at least two years.

The term "electroporation" as used herein refers to a method that utilized electric pulses to deliver a macromolecule, such as a nucleic acid or drug into cells.

The terms "electrical pulse" and "electroporation" as used herein refer to the administration of an electrical current to a tissue or cell for the purpose of taking up a macromolecule such as a nucleic acid or drug into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide of growth hormone releasing hormone.

The term "functional biological equivalent" of GHRH as used herein is a polypeptide that has a distinct amino acid sequence from a wild-type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating the synthesis and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis or direct synthesis.

The term "growth hormone" ("GH") as used herein is defined as a hormone that relates to growth and acts as a chemical messenger to exert its action on a target cell. In a specific embodiment, the growth hormone is synthesized and released by the action of growth hormone releasing hormone.

The term "growth hormone releasing hormone" ("GHRH") as used herein is defined as a hormone that facilitates the synthesis and/or stimulates release of growth hormone, and in a much lesser extent other pituitary hormones, such as prolactin.

The term "heterologous nucleic acid sequence" as used herein is defined as a DNA sequence comprising differing regulatory and expression elements.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31.

The term "modified cells" as used herein is defined as the cells from a subject that have an additional nucleic acid sequence introduced into the cell.

The term "modified-donor-cells" as used herein refers to any donor-cells that have had a GHRH-encoding nucleic acid sequence delivered.

The term "nucleic acid expression construct" as used herein refers to any type of an isolated genetic construct comprising a nucleic acid encoding for a RNA capable of being transcribed. The term "expression vector", "expression cassette" or "expression construct" can also be used interchangeably herein. In specific embodiments, the isolated nucleic acid expression construct comprises: a promoter; a nucleotide sequence of interest; and a 3' polyadenylation and/or 3' untranslated region; wherein the promoter, the nucleotide sequence of interest, and the 3' polyadenylation and/or 3' untranslated region are operatively linked; and in vivo expression of the nucleotide sequence of interest is regulated by the promoter. The term "DNA fragment" as used herein refers to a substantially double stranded DNA molecule. Although the fragment may be generated by any standard molecular biology means known in the art, in some embodiments the DNA fragment or expression construct is generated by restriction digestion of a parent DNA molecule. Although the parent molecule may be any standard molecular biology DNA reagent, in some embodiments the parent DNA molecule is a plasmid.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding GHRH or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing a nucleic acid-expression construct in vivo.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "secretagogue" as used herein refers to an agent that stimulates secretion. For example, a growth hormone secretagogue is any molecule that stimulates the release of growth hormone from the pituitary when delivered into an animal. Growth hormone releasing hormone is a growth hormone secretagogue.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (cows, chicken, fish, lambs, pigs, etc); and all others known in the art.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly (A) sequence, or a 3' or 5' UTR.

The term "transfects" as used herein refers to introduction of a nucleic acid into a eukaryotic cell. In some embodiments, the cell is not a plant tissue or a yeast cell.

The term "vector" as used herein refers to any vehicle that delivers a nucleic acid into a cell or organism. Examples include plasmid vectors. The term also refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

High cholesterol levels are of extraordinary importance for both human and animal medicine, as they can result in numerous long-term pathologies and complications. One specific embodiment of the current invention is a method of decreasing cholesterol levels in a subject. The method comprises: penetrating a muscle tissue in the subject with a plurality of needle electrodes, wherein the plurality of needle electrodes are arranged in a spaced relationship; delivering into the muscle tissue of the subject a nucleic acid expression construct that encodes a growth-hormone-releasing-hormone ("GHRH"), such that an amount of expressed GHRH is effective to enhance the response to a specific vaccination; and applying an electrical pulse to the plurality of needle electrodes, wherein the electrical pulse allows the nucleic acid expression construct to traverse a muscle cell membrane. A range of 0.05-5 mg of nucleic acid expression construct with a defined concentration of poly-L-glutamate polypeptide is delivered into the muscle tissue of the subject, and the nucleic acid expression construct comprises a sequence that encodes a polypeptide having an amino acid sequence that is at least 90% identical to the encoded GHRH of SEQ ID#14. The preferred subject comprises a human, a ruminant animal, a food animal, a horse, or a work animal.

A second preferred embodiment includes the nucleic acid expression construct being delivered in a single dose, and the single dose comprising a total of about a 0.05-5 mg of nucleic acid expression construct. Generally the nucleic acid expression construct is delivered into a tissue of the subject comprising diploid cells (e.g. muscle cells).

In a third specific embodiment the nucleic acid expression construct used for transfection comprises a wt-porcine-GHRH plasmid, pAV0242 (SEQ ID NO:25). Other specific embodiments utilize other nucleic acid expression constructs (e.g. an optimized bovine GHRH plasmid, pAV0236 (SEQ ID NO:27); a TI-GHRH plasmid, pAV0239 (SEQ ID NO:29); HV-GHRH plasmid, pAV0224 (SEQ ID NO:24); ovine GHRH plasmid, pAV0240 (SEQ ID NO:30); chicken GHRH plasmid, pAV0241 (SEQ ID NO:31); dog GHRH plasmid, pAV0235 (SEQ ID NO:26); cat GHRH plasmid, pAV0238 (SEQ ID NO:28); horse GHRH plasmid, pAV0249; human GHRH plasmid, pAV0243 (SEQ ID NO:32); mouse GHRH plasmid, pAV0248 (SEQ ID NO:34); or rat GHRH plasmid, pAV0218 (SEQ ID NO:35).

In a fourth specific embodiment, the nucleic acid expression construct further comprises, a transfection-facilitating polypeptide (e.g. a charged polypeptide, or poly-L-glutamate). After delivering the nucleic acid expression construct into the tissues of the subject, expression of the encoded GHRH or functional biological equivalent thereof is initiated. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQ ID#14). The animal comprises a human, a food animal, a work animal (e.g. a pig, cow, sheep, goat or chicken), or a pet (e.g. dog, cat, horse).

The general method of this invention comprises treating a subject with plasmid-mediated gene supplementation. The method comprises delivering a nucleic acid expression construct that encodes a growth-hormone-releasing-hormone ("GHRH") or functional biological equivalent thereof into a tissue, such as a muscle, of the subject. Specific embodiments of this invention are directed toward improving cholesterol levels in treated subjects by plasmid mediated GHRH supplementation. It is also possible to enhance this method by placing a plurality of electrodes in a selected tissue, then delivering nucleic acid expression construct to the selected tissue in an area that interposes the plurality of electrodes, and applying a cell-transfecting pulse (e.g. electrical) to the selected tissue in an area of the selected tissue where the nucleic acid expression construct was delivered. However, the cell-transfecting pulse need not be an electrical pulse, a different, less efficient method, such as vascular pressure pulse can also be utilized. Direct injection, gene gun, or gold particle bombardment could also be used in specific embodiments to deliver the nucleic acid expression construct encoding the GHRH or biological equivalent into the subject. The subject in this invention comprises an animal (e.g. a human, a pig, a horse, a cow, a mouse, a rat, a monkey, a sheep, a goat, a dog, or a cat).

Recombinant GH replacement therapy is widely used in agriculture and clinically, with beneficial effects, but generally, the doses are supraphysiological. Such elevated doses of recombinant GH are associated with deleterious side-effects, for example, up to 30% of the recombinant GH treated subjects develop at a higher frequency insulin resistance (Gopinath and Etherton, 1989a; Gopinath and Etherton, 1989b; Verhelst et al., 1997) or accelerated bone epiphysis growth and closure in pediatric patients (Blethen and Rundle, 1996). In addition, molecular heterogeneity of circulating GH may have important implications in growth and homeostasis (Satozawa et al., 2000; Tsunekawa et al., 1999; Wada et al., 1998). Unwanted side effects result from the fact that treatment with recombinant exogenous GH protein raises basal levels of GH and abolishes the natural episodic pulses of GH. In contradistinction, no side effects have been reported for recombinant GHRH therapies. The normal levels of GHRH in the pituitary portal circulation range from about 150-to-800 pg/ml, while systemic circulating values of the hormone are up to about 100-500 pg/ml. Some patients with acromegaly caused by extracranial tumors have level that is nearly 100 times as high (e.g. 50 ng/ml of immunoreactive GHRH) (Thorner et al., 1984). Long-term studies using recombinant GHRH therapies (1-5 years) in children and elderly humans have shown an absence of the classical GH side-effects, such as changes in fasting glucose concentration or, in pediatric patients, the accelerated bone epiphysal growth and closure or slipping of the capital femoral epiphysis (Chevalier et al., 2000; Duck et al., 1992; Vittone et al., 1997).

Studies in humans, sheep or pigs showed that continuous infusion with recombinant GHRH protein restores the normal GH pattern without desensitizing GHRH receptors or depleting GH supplies (Dubreuil et al., 1990). As this system is capable of a degree of feed-back which is abolished in the GH therapies, GHRH recombinant protein therapy may be more physiological than GH therapy. However, due to the short half-life of GHRH in vivo, frequent (one to three times per day) intravenous, subcutaneous or intranasal (requiring 300-fold higher dose) administrations are necessary (Evans et al., 1985; Thorner et al., 1986b). Thus, as a chronic therapy, recombinant GHRH protein administration is not practical. A plasmid-mediated supplementation approach, however could overcome this limitations to GHRH use. The choice of GHRH for a gene therapeutic application is favored by the fact that the gene, cDNA and native and several mutated molecules have been characterized for humans, pig, cattle and other species (Bohlen et al., 1983; Guillemin et al., 1982); we have isolated the cDNA of cat, dog and horse specific GHRH. The measurement of therapeutic efficacy is straightforward and unequivocal.

Among the non-viral techniques for gene transfer in vivo, the direct injection of plasmid DNA into muscle is simple, inexpensive, and safe. The inefficient DNA uptake into muscle fibers after simple direct injection had led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996). Recently, significant progress and therapeutic levels of proteins have been obtained using electroporation to enhance plasmid delivery in vivo. Our previous studies using GHRH showed that plasmid therapy with electroporation is scalable and represents a promising approach to induce production and regulated secretion of proteins in large animals and humans (Brown et al., 2004; Draghia-Akli and Fiorotto, 2004; Tone et al., 2004). The optimum conditions of electroporation (including for instance the choice of pulse shape, pulse amplitude and length) are highly dependent on target tissue, formulation, type of application (therapeutic vs. vaccination), device and type of electrodes used, etc. The type of electrodes is also highly dependent on the target species and organ. While external (caliper, tweezers, plates, etc.) electrodes can be successfully used in rodents or for skin electroporation, internal electrodes are needed for instance for the EP of muscle and skin in larger animals (Prud'homme et al., 2006).

The ability of electroporation to enhance plasmid uptake into the skeletal muscle has been well documented, as described above. In addition, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency.

Although not wanting to be bound by theory, the plasmid supplementation approach to decrease cholesterol levels described herein offers advantages over the limitations of directly injecting recombinant GH or GHRH protein. Expression of GHRH or novel biological equivalents of GHRH can be directed by an expression plasmid controlled by a synthetic muscle-specific promoter. Expression of such GHRH or biological equivalent thereof elicited high GH and IGF-I levels in subjects that have had the encoding sequences delivered into the cells of the subject by intramuscular injection and in vivo electroporation. Although in vivo electroporation is the preferred method of introducing the heterologous nucleic acid encoding system into the cells of the subject, other methods exist and should be known by a person skilled in the art (e.g. electroporation, lipofectamine, calcium phosphate, ex vivo transformation, direct injection, DEAE dextran, sonication loading, receptor mediated transfection, microprojectile bombardment, etc.). For example, it may also be possible to introduce the nucleic acid sequence that encodes the GHRH or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). Plasmid DNA carrying the GHRH sequence can be complexed with cationic lipids or liposomes and delivered intramuscularly, intravenously or subcutaneous.

Administration as used herein refers to the route of introduction of a vector or carrier of DNA into the body. Administration can be directly to a target tissue or by targeted delivery to the target tissue after systemic administration. The preferred means for administration of vector and use of formulations for delivery are described above.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhanced utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determine the bioavailability of the vector within the body. Other elements of the formulation function as ligands that interact with specific receptors on the surface or interior of the cell. Other elements of the formulation function to enhance entry into the cell, release from the endosome, and entry into the nucleus.

Delivery can also be through use of DNA transporters. DNA transporters refer to molecules that bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane. See, e.g., the applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand that recognizes specific receptors or other functional groups such as a protein complexed with a cationic group that binds to DNA. Examples of cations which may be used are spermine, spermine derivatives, histone, cationic peptides and/or polylysine; one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months. Myoblasts eventually differentiate and fuse to existing muscle tissue. Because the cell is incorporated into an existing structure, it is not just tolerated but nurtured. Myoblasts can easily be obtained by taking muscle tissue from an individual who needs plasmid-mediated supplementation and the genetically engineered cells can also be easily put back with out causing damage to the patient's muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 and E3 regions of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

Vectors

The term "vector" is used to refer to a carrier nucleic acid molecule into which a nucleic acid sequence can be inserted for introduction into a cell. A nucleic acid sequence can be native to the animal or it can be "exogenous," which means that it is foreign to the cell into which the vector is being introduced or that the sequence is homologous to a sequence in the cell but in a position within the host cell in which is ordinarily not found. Vectors include plasmids, cosmids, viruses (bacteriophage, animal viruses, and plant viruses), linear DNA fragments, and artificial chromosomes (e.g., YACs, BACs). One of skill in the art would be well equipped to construct a vector through standard recombinant techniques.

The term "expression vector" refers to any type of genetic construct comprising a nucleic acid encoding for a RNA capable of being transcribed. In some cases, RNA molecules are then translated into a protein, polypeptide, or peptide. In other cases, these sequences are not translated, for example, in the production of anti-sense molecules or ribozymes. Expression vectors can contain a variety of "control sequences," which refer to nucleic acid sequences necessary for the transcription and possibly translation of an operatively linked coding sequence in a particular host cell. In addition to control sequences that govern transcription and translation, vectors and expression vectors may contain nucleic acid sequences that serve other functions as well and are described infra.

Plasmid Vectors

In general, plasmids containing replicon and control sequences derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322 or pUC, plasmids derived from *E. coli* species. pBR322 contains genes for ampicillin and tetracycline resistance and thus provides easy means for identifying transformed cells. Other plasmids contain genes for kanamycin or neomycin, or have a non-antibiotic selection mechanism. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH plasmid used for the therapeutic applications is synthetically produced and has a kanamycin resistance gene (SEQ ID#17).

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392. Further useful plasmid vectors may include pIN vectors (Inouye et al., 1985); and pGEX vectors, for use in generating glutathione S-transferase soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control" and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the timidine kinase promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | Relevant References |
| --- | --- |
| β-Actin | (Kawamoto et al., 1988; Kawamoto et al., 1989) |
| Muscle Creatine Kinase (MCK) | (Horlick and Benfield, 1989; Jaynes et al, 1988) |
| Metallothionein (MTII) | (Inouye et al., 1994; Narum et al., 2001; Skroch et al., 1993) |
| Albumin | (Pinkert et al., 1987; Tronche et al., 1989) |
| β-Globin | (Tronche et al., 1990; Trudel and Costantini, 1987) |
| Insulin | (German et al., 1995; Ohlsson et al., 1991) |
| Rat Growth Hormone | (Larsen et al., 1986) |
| Troponin I (TN I) | (Lin et al., 1991; Yutzey and Konieczny, 1992) |
| Platelet-Derived Growth Factor | (Pech et al., 1989) |
| Duchenne Muscular Dystrophy | (Klamut et al., 1990; Klamut et al., 1996) |
| Cytomegalovirus (CMV) | (Boshart et al., 1985; Dorsch-Hasler et al., 1985) |
| Synthetic muscle specific promoters | (Draghia-Akli et al., 1999; Draghia-Akli et al., 2002c; Li et al., 1999) |

TABLE 2

Element/Inducer

| Element | Inducer |
| --- | --- |
| MT II | Phorbol Ester (TFA) Heavy metals |
| MMTV (mouse mammary tumor virus) | Glucocorticoids |
| β-Interferon | Poly(rI)x/Poly(rc) |
| Adenovirus 5 E2 | E1A |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | E1A, SV40 Large T Antigen |
| Proliferin | Phorbol Ester-TPA |
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), D1A dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (SEQ ID#15) (Li et al., 1999), which contains a proximal serum response element ("SRE") from skeletal alpha-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites ("IRES") elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, (Chandler et al., 1997)).

Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the human growth hormone or bovine growth hormone terminator or other termination sequences, such as for example the SV40 terminator. In certain embodiments, the termination signal may be a lack of transcribable or translatable sequence, such as due to a sequence truncation.

Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal, skeletal alpha actin 3'UTR or the human (SEQ ID#16) or bovine growth hormone polyadenylation signal, convenient and known to function well in various target cells. Polyadenylation may increase the stability of the transcript or may facilitate cytoplasmic transport.

Origins of Replication

In order to propagate a vector in a host cell, it may contain one or more origins of replication sites (often termed "ori"), which is a specific nucleic acid sequence at which replication is initiated; in a specific embodiment the origin of replication is derived from a pUC-18 (SEQ ID#19). Alternatively an autonomously replicating sequence ("ARS") can be employed if the host cell is yeast.

Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, for instance kanamycin.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase ("tk") or chloramphenicol acetyltransferase ("CAT") may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Electroporation

In certain embodiments of the present invention, a nucleic acid is introduced into an organelle, a cell, a tissue or an organism via electroporation. Electroporation involves the exposure of a suspension of cells and DNA to an electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances maintain a resting transmembrane potential of circa 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula E=V/d, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the inter-electrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

Overcoming the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. Some electroporation devices utilize the distance between electrodes to calculate the electric field strength and predetermined voltage pulses for electroporation. This reliance on knowing the distance between electrodes is a limitation to the design of electrodes. In the case of a constant current device, because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

One example of an electroporation device that may be used to effectively facilitate the introduction of a macromolecule into cells of a selected tissue of a subject was described in U.S. patent application Ser. No. 10/657,725 filed on Sep. 8, 2003, titled "Constant Current Electroporation Device and Methods Of Use," with Smith et al., listed as inventors, the entirety of which is hereby incorporated by reference. The electroporation device comprises an electro-kinetic device ("EKD") whose operation is specified by software or firmware. The EKD produces a series of programmable constant-current pulse patterns between electrodes in an array based on user control and input of the pulse parameters and allows the storage and acquisition of current waveform data. The electroporation device also comprises a replaceable electrode disk having an array of needle electrodes, a central injection channel for an injection needle, and a removable guide disk.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Construction of DNA Vectors

DNA constructs: In order to decrease cholesterol levels in a treated subject it was first necessary to design several GHRH constructs. Briefly, the plasmid vectors contained the muscle specific synthetic promoter SPc5-12 (SEQ ID#15) (Li et al., 1999) attached to a wild type species-specific or analog GHRH. Some wild-type GHRH sequences were cloned in our laboratory (dog, cat and horse); others (chicken, ovine, bovine, porcine, human) were synthesized according to the specialized literature. The analog GHRH sequences were generated as described (Draghia-Akli et al., 1999). All sequences were codon optimized for the target species. The resultant plasmids contained mammalian analog coding region for GHRH, and the resultant amino acid sequences were not naturally present in mammals. The control plasmid (pSP-β-gal) was similar but contained the E. coli β-galactosidase gene, in place of the GHRH cDNA. Endotoxin-free plasmid preparations were diluted in water to 1 mg/mL formulated with PLG for injection. Although not wanting to be bound by theory, the decrease of cholesterol levels is determined ultimately by the circulating levels of GHRH hormones. Several different plasmids encoded different mutated or wild type amino acid sequences of GHRH or functional biological equivalents thereof, for example:

The plasmids described above do not contain polylinker, other transgenes, such as IGF-I gene, a skeletal alpha-actin promoter or a skeletal alpha actin 3' UTR/NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and poly-nucleotides) in selected amino acids (or codons) may be substituted. A peptide comprising a functional biological equivalent of GHRH is a polypeptide that has been engi-

| Plasmid | Encoded Amino Acid Sequence |
|---|---|
| HV-GHRH (SEQID#1): | HVDAIFTNSYRKVLAQLSARKLLQDILNRQQGERNQEQGA-OH |
| Pig-GHRH (SEQID#2): | YADAIFTNSYRKVLGQLSARKLLQDIMSRQQGERNQEQGA-OH |
| Bovine-GHRH (SEQID#3): | YADAIFTNSYRKVLGQLSARKLLQDIMNRQQGERNQEQGA-OH |
| Dog-GHRH (SEQID#4): | YADAIFTNSYRKVLGQLSARKLLQDIMSRQQGERNEQGA-OH |
| Cat-GHRH (SEQID#5): | YADAIFTNSYRKVLGQLSARKLLQDIMSRQQGERNQEQGA-OH |
| TI-GHRH (SEQID#6): | YIDAIFTNSYRKVLAQLSARKLLQDILNRQQGERNQEQGA-OH |
| Ovine-GHRH (SEQID#7): | YADAIFTNSYRKILGQLSARKLLQDIMNRQQGERNQEQGA-OH |
| Chicken-GHRH (SEQID#8): | HADGIFSKAYRKLLGQLSARNYLHSLMAKRVGSGLGDEAEPLS-OH |
| Horse-GHRH (partial) (SEQID#9): | -ADAIFTNNYRKVLGQLSARKILQDIMSR----------OH |
| human-GHRH (SEQID#10): | YADAIFTNSYRKVLGQLSARKLLQDIMSRQQGESNQERGA-OH |
| TV-GHRH (SEQID#11): | YVDAIFTNSYRKVLAQLSARKLLQDILNRQQGERNQEQGA-OH |
| TA-(15/27/28)-GHRH (SEQID#12): | YADAIFTNSYRKVLAQLSARKLLQDILNRQQGERNQEQGA-OH |

In general, the encoded GHRH or functional biological equivalent thereof is of formula:

(SEQID#14)

-X$_1$-X$_2$-DAIFTNSYRKVL-X$_3$-QLSARKLLQDI-X$_4$-X$_5$-RQQGE-X$_6$-N-X$_7$-E-X$_8$-GA-OH wherein: X$_1$ is a D- or L-isomer of an amino acid selected from the group consisting of tyrosine ("Y"), or histidine ("H"); X$_2$ is a D- or L-isomer of an amino acid selected from the group consisting of alanine ("A"), valine ("V"), or isoleucine ("I"); X$_3$ is a D- or L-isomer of an amino acid selected from the group consisting of alanine ("A") or glycine ("G"); X$_4$ is a D- or L-isomer of an amino acid selected from the group consisting of methionine ("M"), or leucine ("L"); X$_5$ is a D- or L-isomer of an amino acid selected from the group consisting of serine ("S") or asparagines ("N"); X$_6$ is a D- or L-isomer of an amino acid selected from the group consisting of arginine ("R"), or serine ("S"); X$_7$ is a D- or L-isomer of an amino acid selected from the group consisting of arginine ("R"), or glutamine ("Q"); and X$_8$ is a D- or L-isomer of an amino acid selected from the group consisting of arginine ("R"), or glutamine ("Q").

neered to contain distinct amino acid sequences while simultaneously having similar or improved biologically activity when compared to GHRH. For example one biological activity of GHRH is to facilitate GH synthesis and secretion in the subject.

Figure 6:
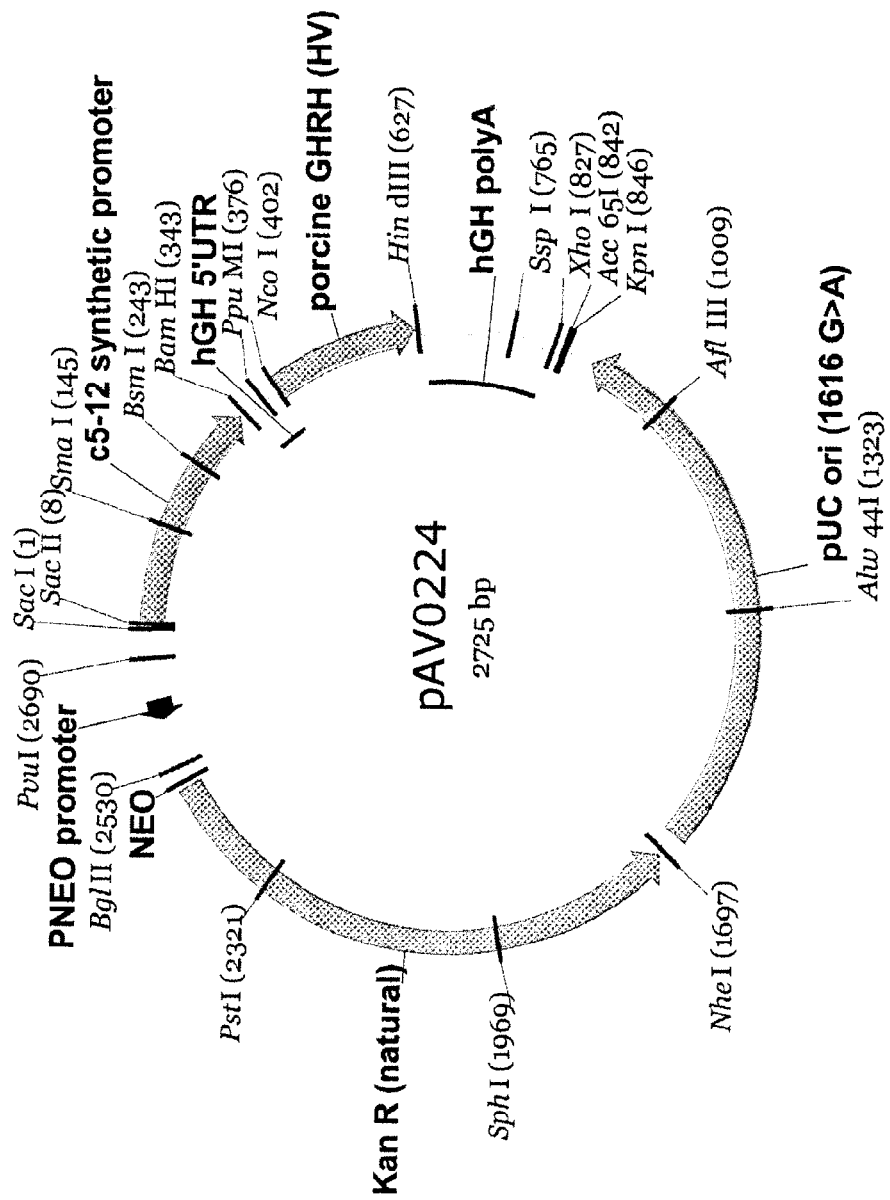
FIG. 6 shows a restriction map of pAV0224 (HV-GHRH) expression plasmid.
Figure 7:
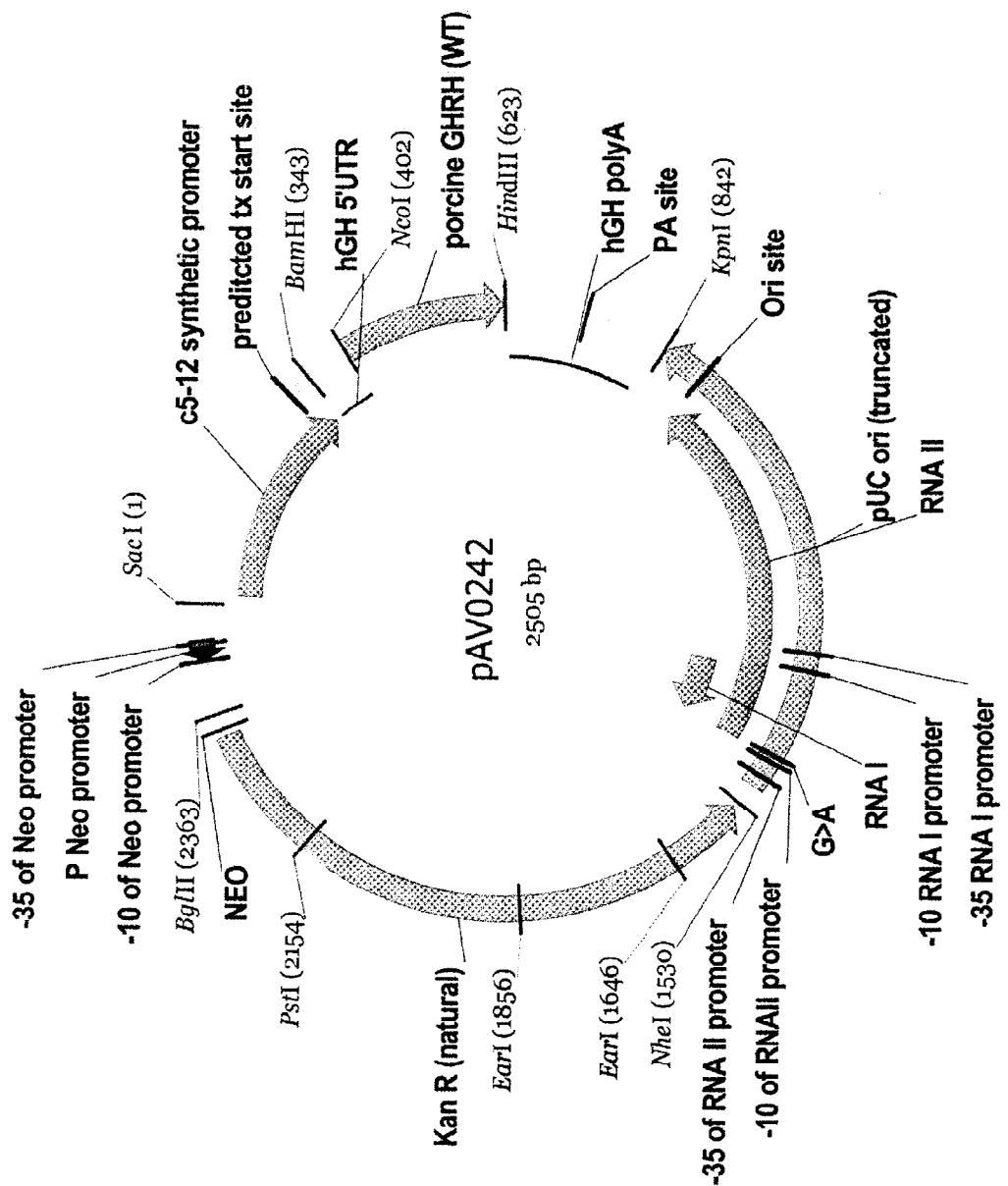
FIG. 7 shows a restriction map of pAV0242 (porcine-GHRH) expression plasmid.
Figure 8:
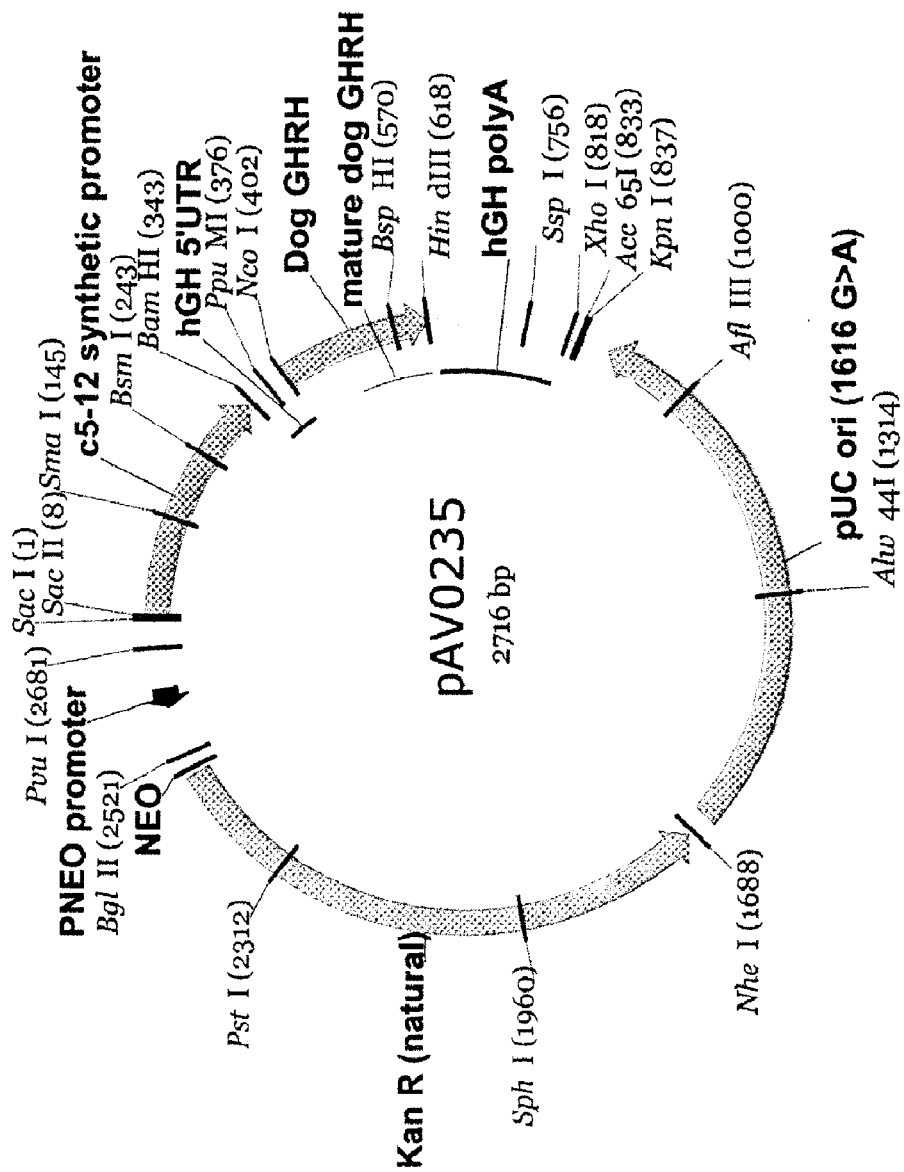
FIG. 8 shows a restriction map of pAV0235 (dog-GHRH) expression plasmid.
Figure 9:
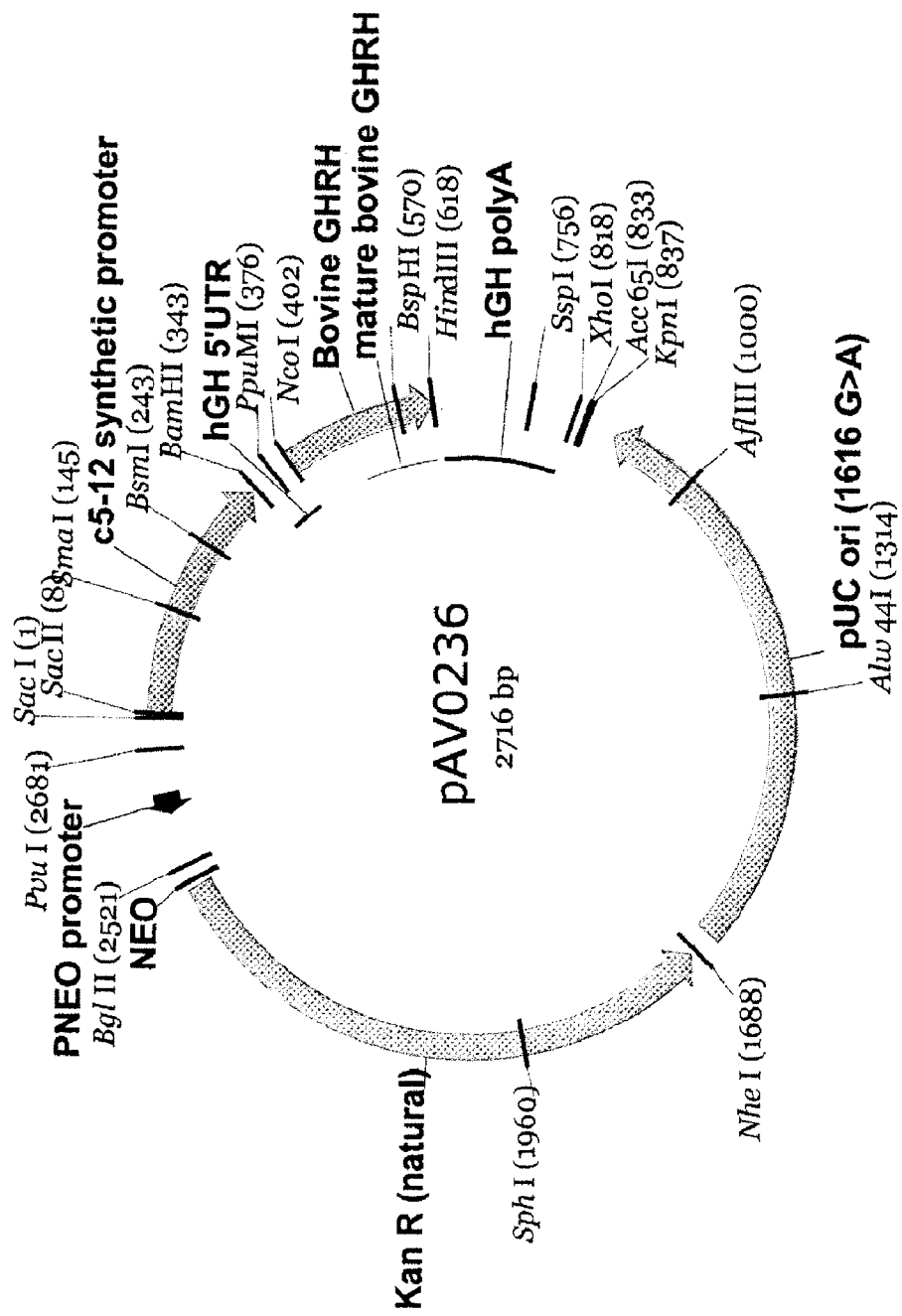
FIG. 9 shows a restriction map of pAV0236 (bovine-GHRH) expression plasmid.
Figure 10:
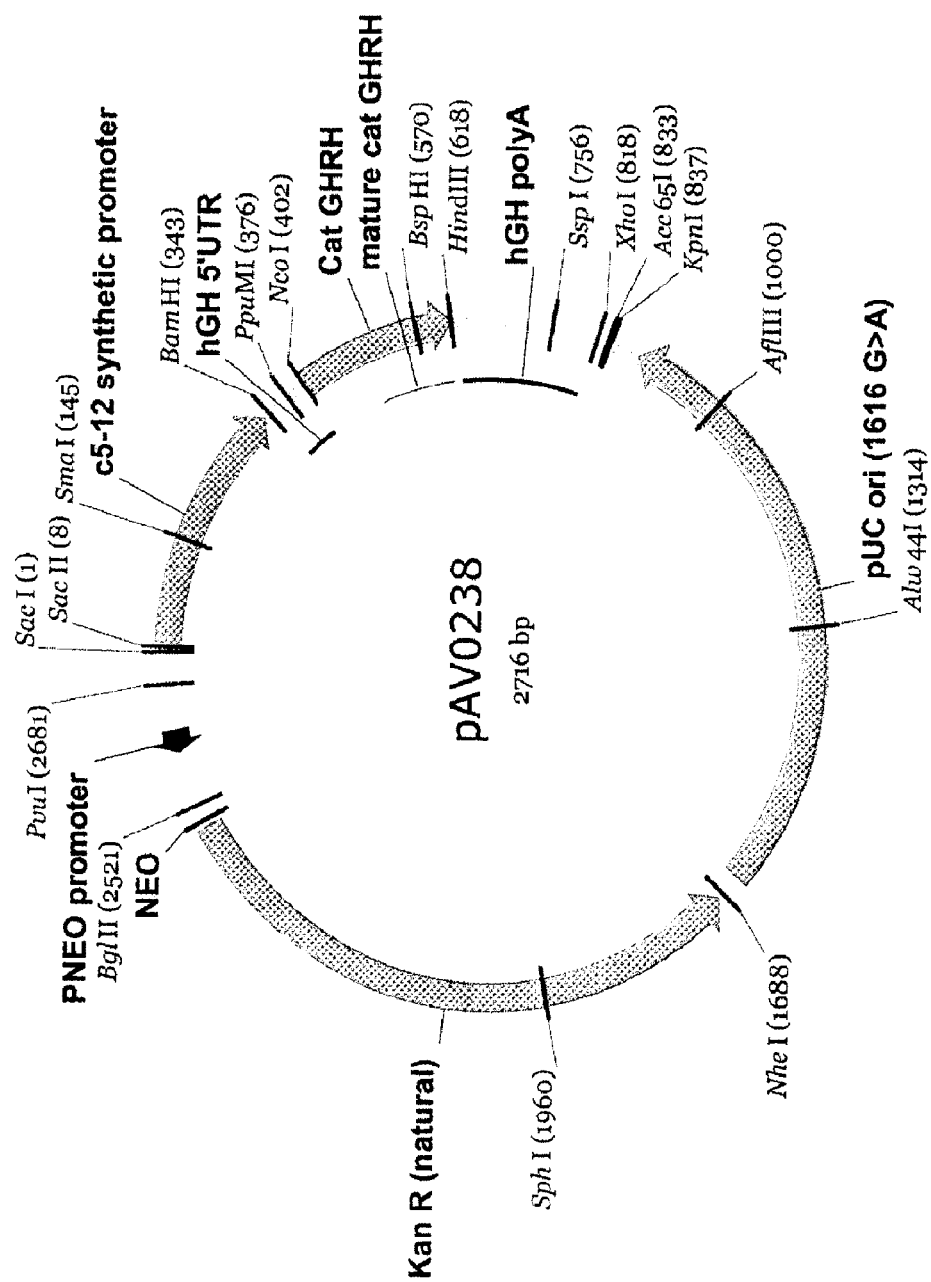
FIG. 10 shows a restriction map of pAV0238 (cat-GHRH) expression plasmid.
Figure 11:
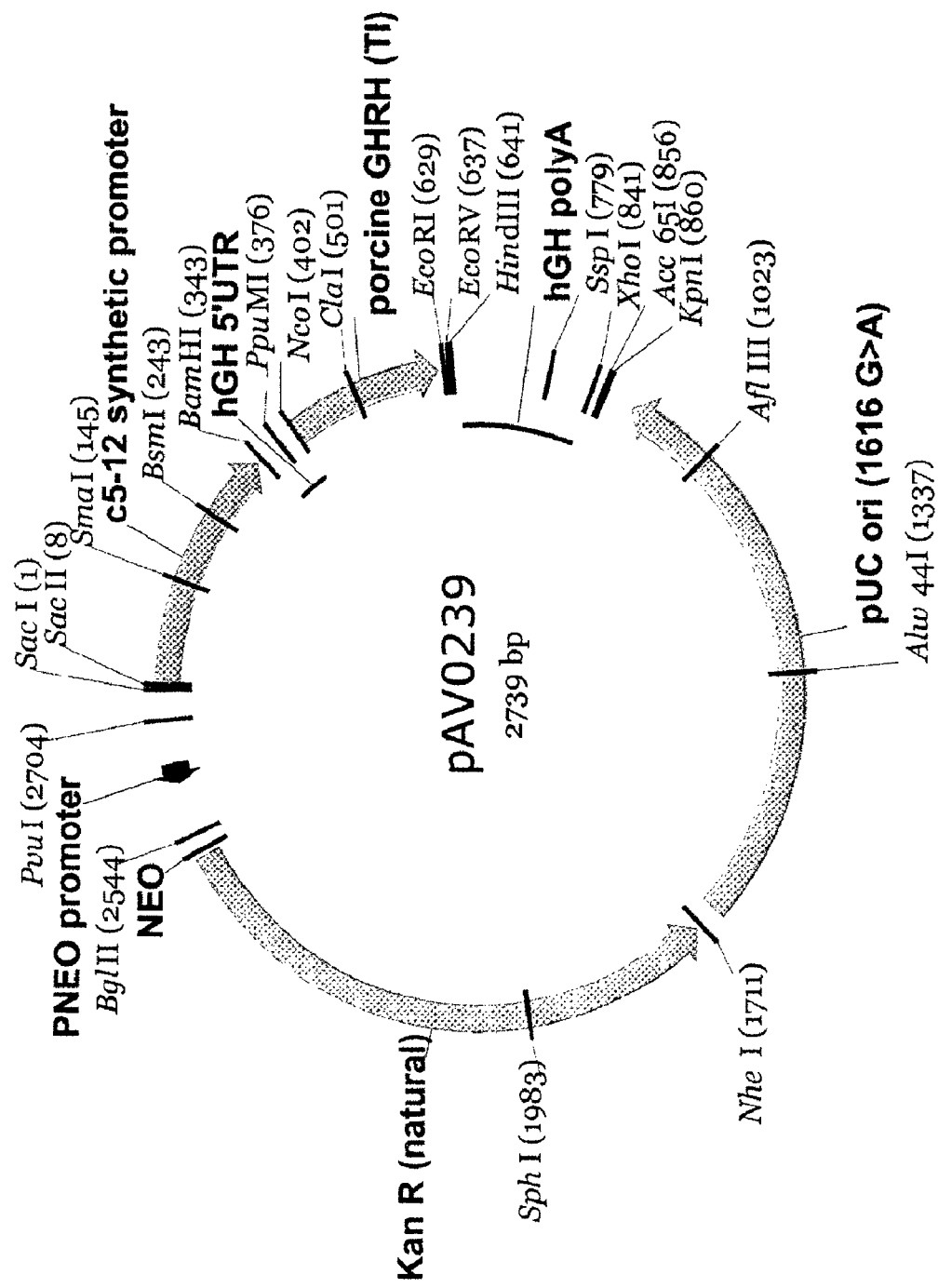
FIG. 11 shows a restriction map of pAV0239 (TI-GHRH) expression plasmid.
Figure 12:
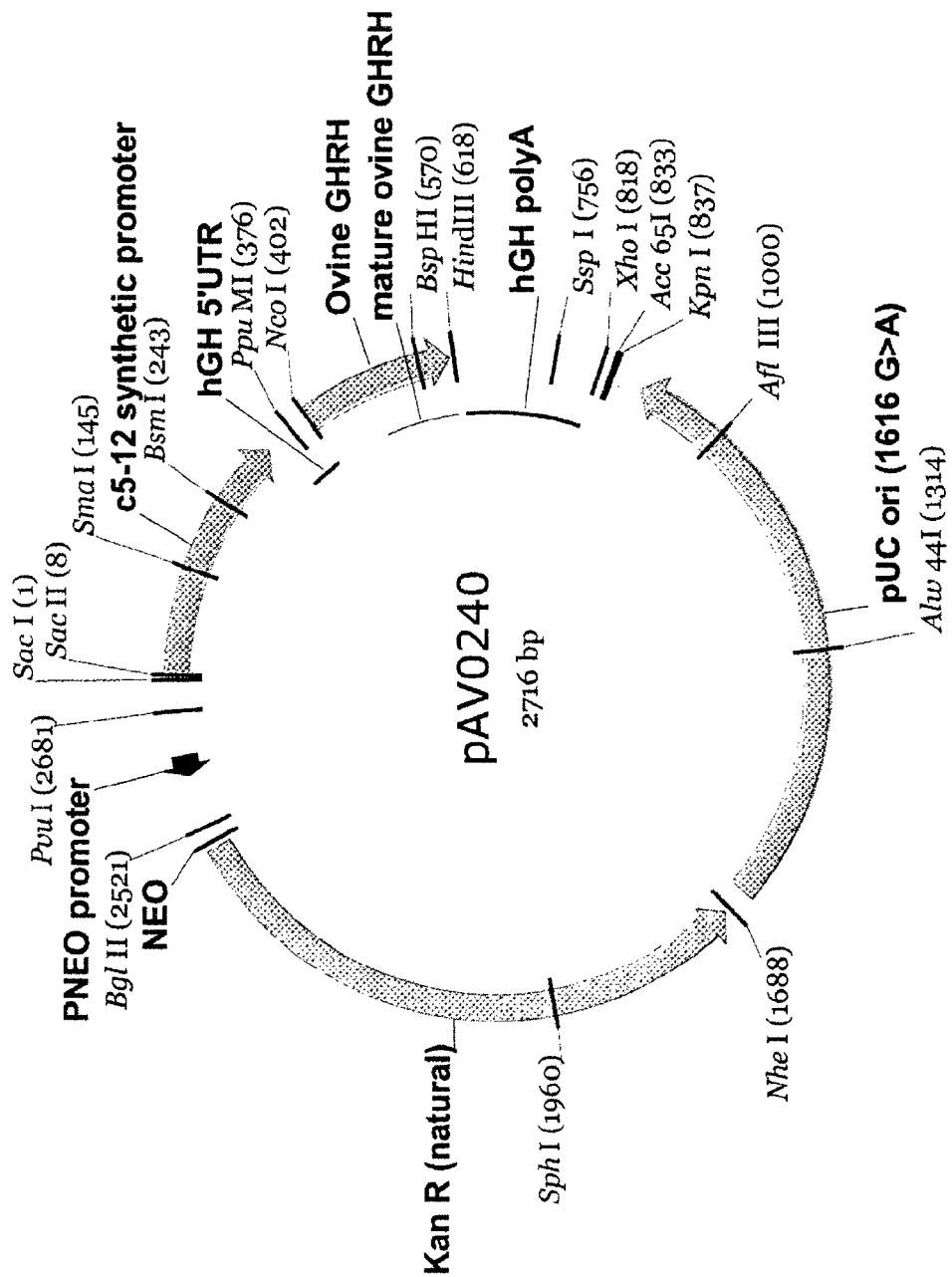
FIG. 12 shows a restriction map of pAV0240 (ovine-GHRH) expression plasmid.
Figure 13:
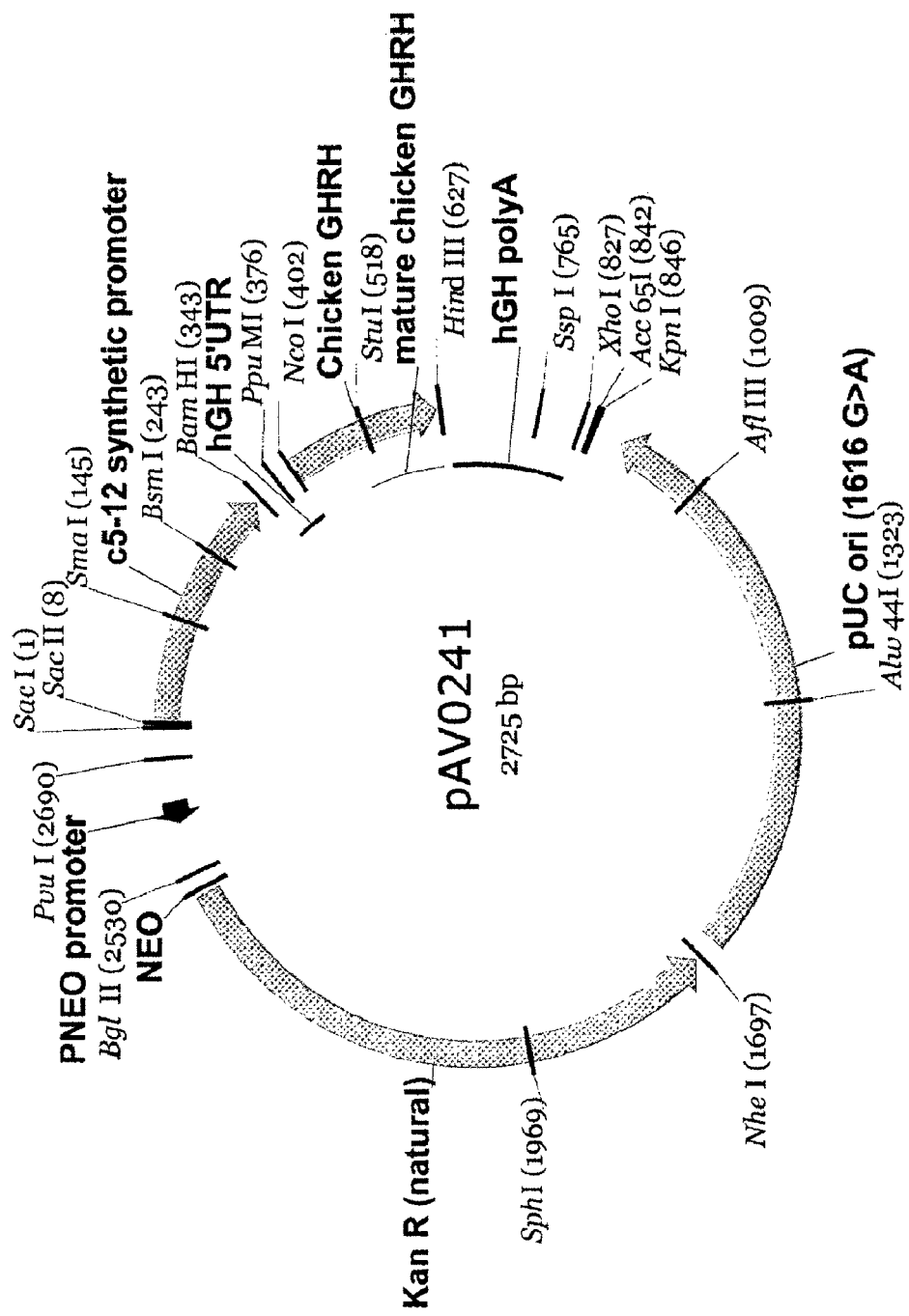
FIG. 13 shows a restriction map of pAV0241 (chicken-GHRH) expression plasmid.
Figure 14:
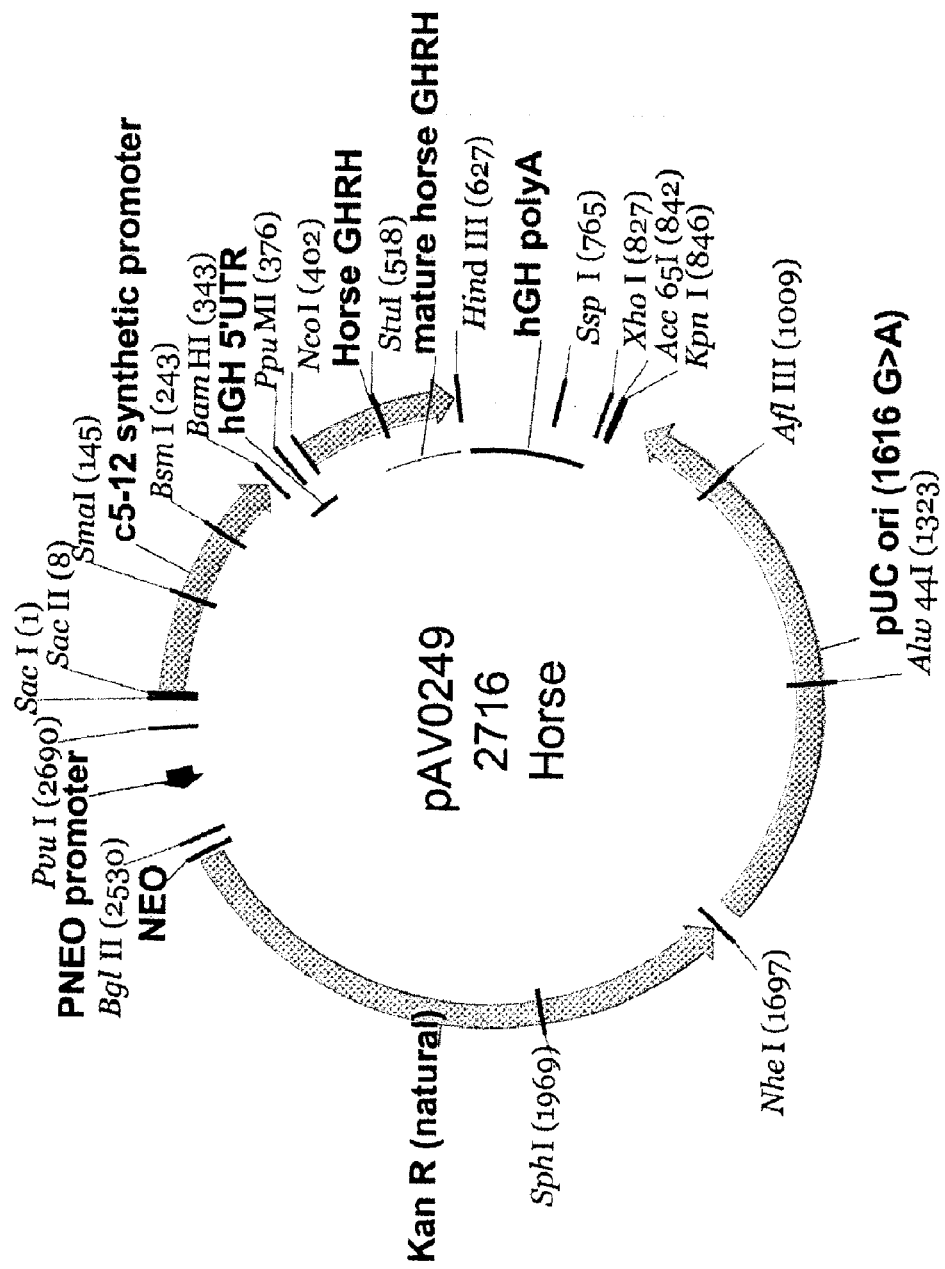
FIG. 14 shows a restriction map of pAV0249 (horse-GHRH) expression plasmid.
Figure 15:
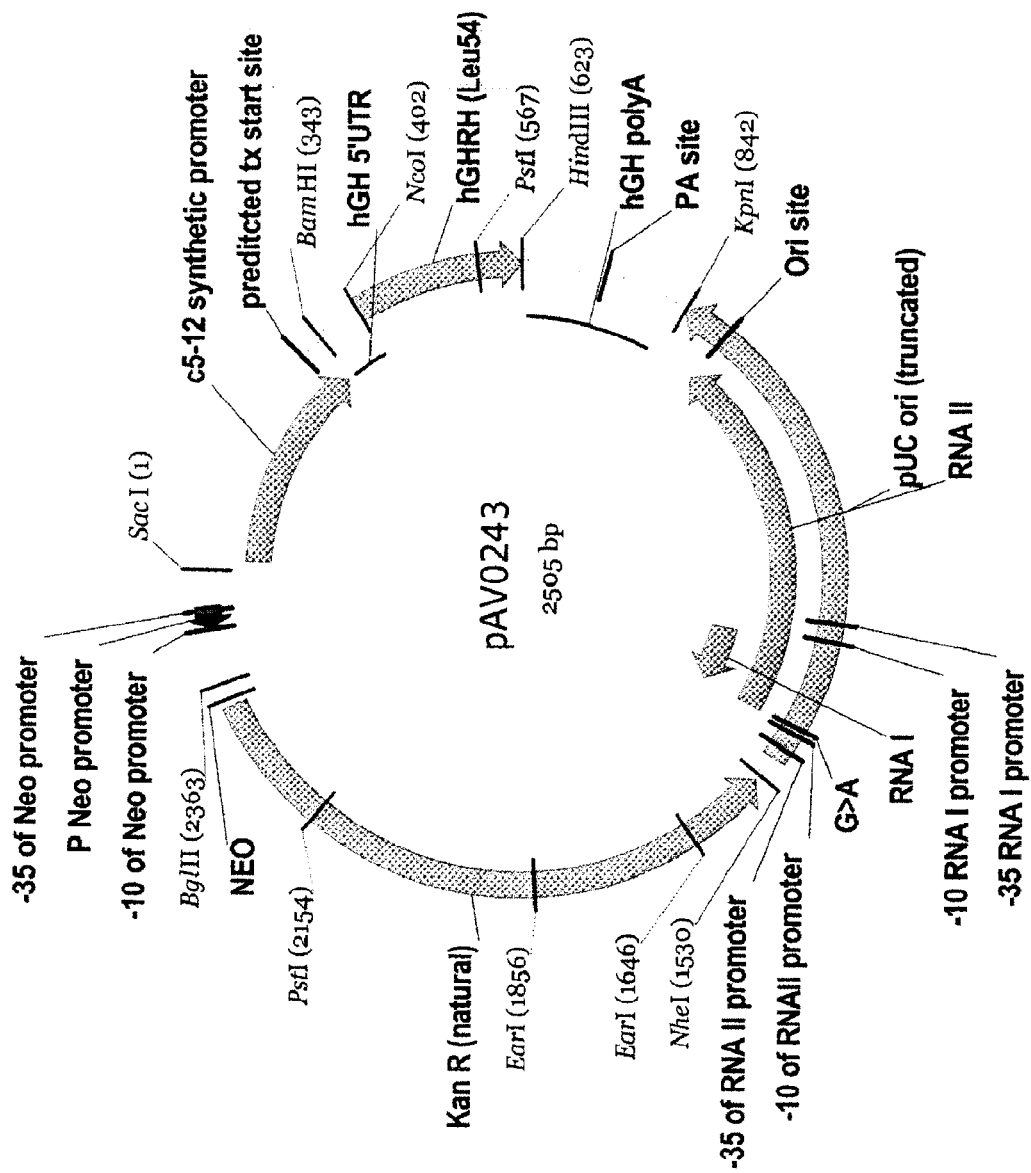
FIG. 15 shows a restriction map of pAV0243 (human-GHRH) expression plasmid.
Figure 16:
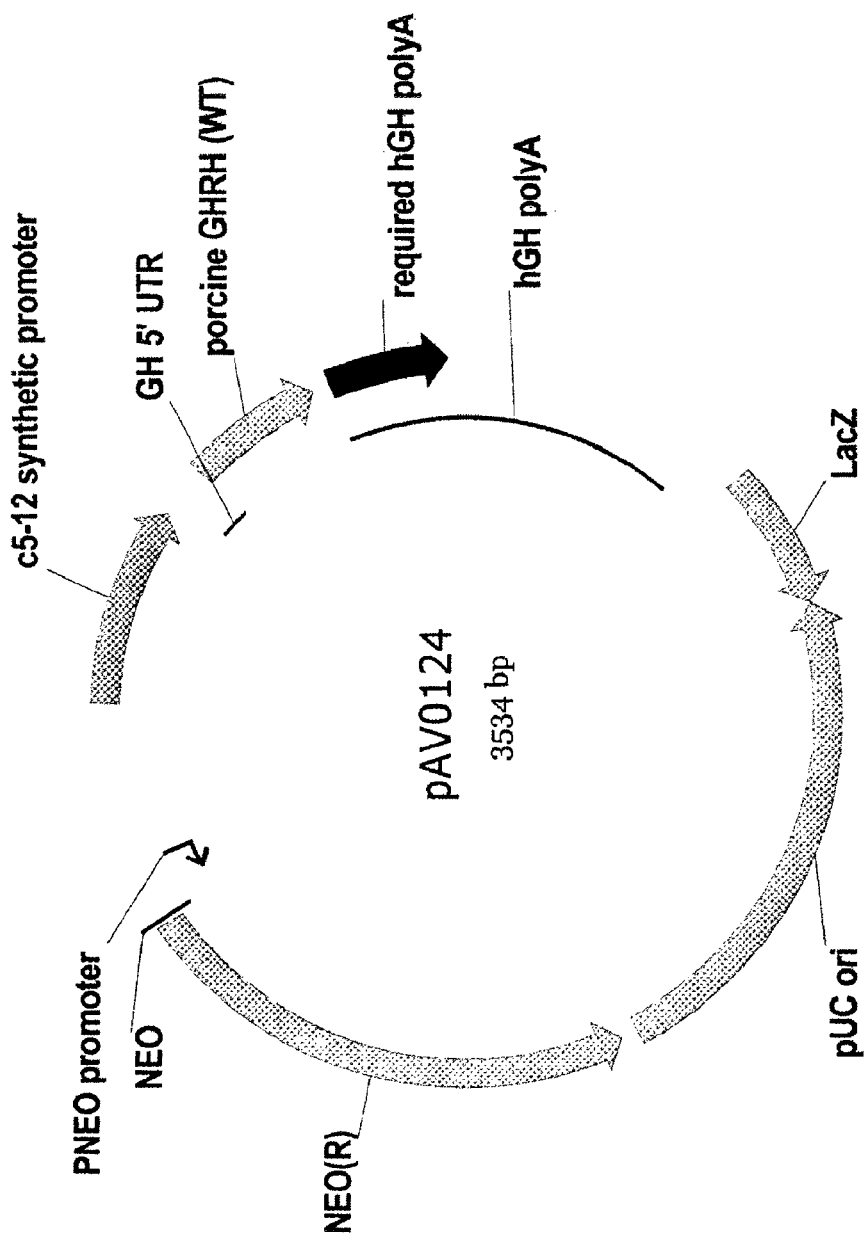
FIG. 16 shows a restriction map of pAV0124 (porcine-GHRH) expression plasmid.
Figure 17:
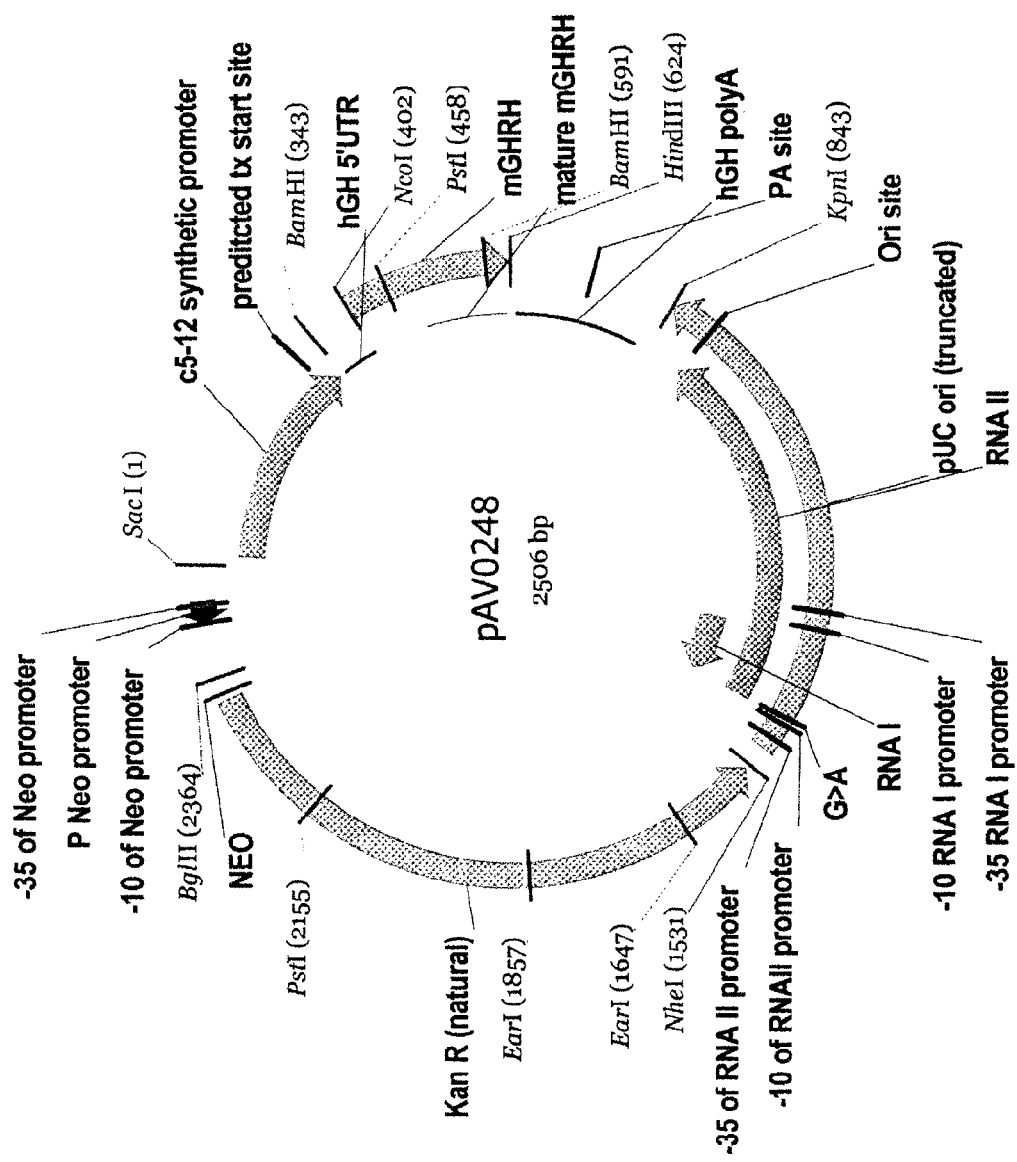
FIG. 17 shows a restriction map of pAV0248 (mouse-GHRH) expression plasmid.
Figure 18:
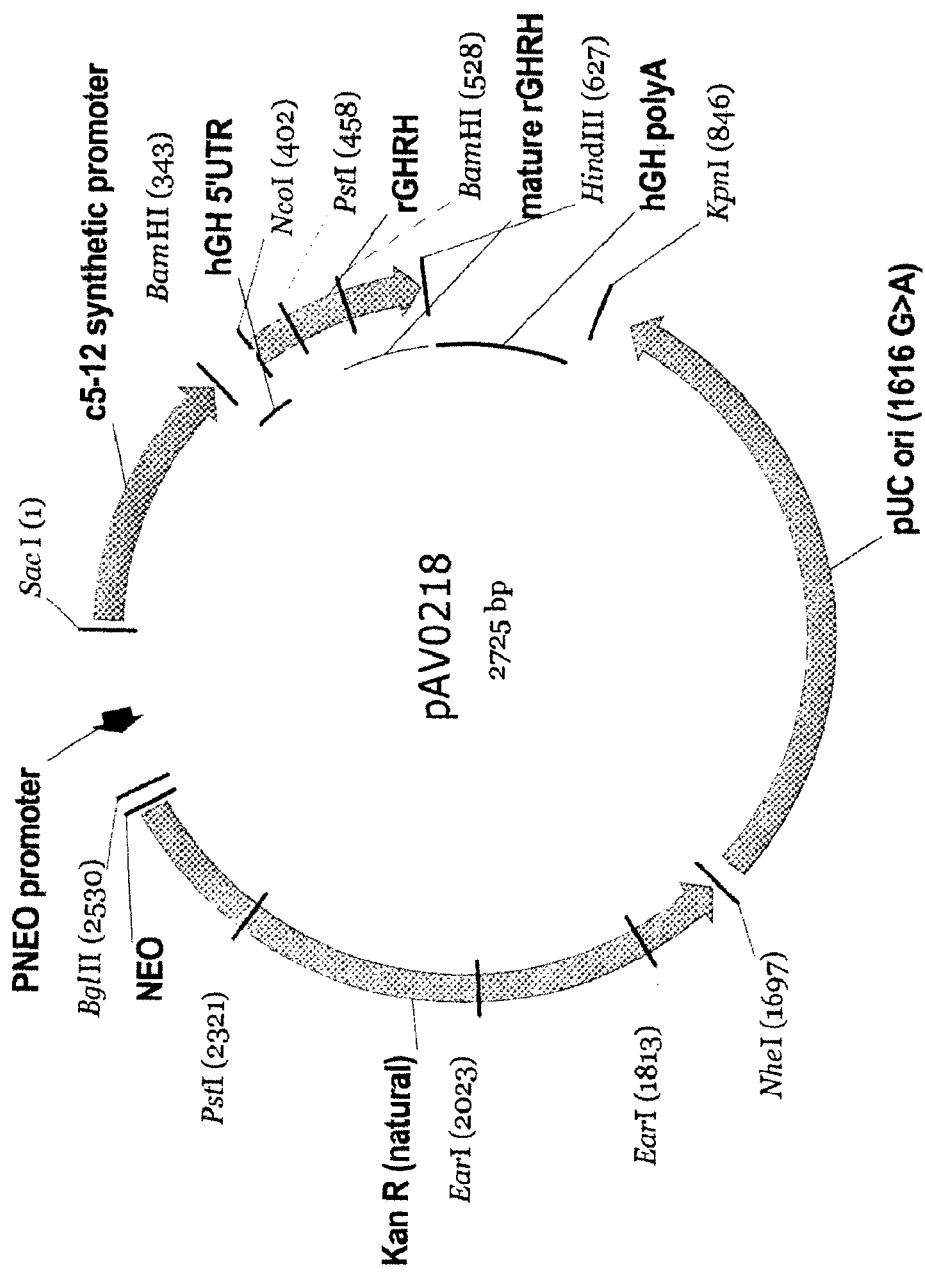
FIG. 18 shows a restriction map of pAV0218 (rat-GHRH) expression plasmid.

Optimized Plasmid Backbone. One aspect of the current invention is the optimized plasmid backbone. The synthetic plasmids presented below contain eukaryotic sequences that are synthetically optimized for species specific mammalian transcription. An existing pSP-HV-GHRH plasmid ("pAV0125") (SEQ ID NO:21), was synthetically optimized to form a new plasmid (SEQ ID NO:24). The plasmid pAV0125 was described in U.S. Pat. No. 6,551,996 titled "Super-active porcine growth hormone releasing hormone analog," issued on Apr. 22, 2003 with Schwartz, et al., listed as inventors ("the Schwartz '996 Patent"), which teaches application of a GHRH analog containing mutations that improve their ability to elicit the release of growth hormone. Other specific examples of optimized synthetic plasmids include an optimized wt-porcine GHRH plasmid, pAV0242 (SEQ ID NO:25), as described in FIG. 7. Other specific embodiments utilize other nucleic acid expression constructs (e.g. an optimized bovine GHRH plasmid, pAV0236 (SEQ ID NO:27 and FIG. 9); a TI-GHRH plasmid, pAV0239 (SEQ ID NO:29 and FIG. 11); HV-GHRH plasmid, pAV0224 (SEQ ID NO:24 and FIG. 6); ovine GHRH plasmid, pAV0240 (SEQ ID NO:30 and FIG. 12); chicken GHRH plasmid, pAV0241 (SEQ ID NO:31 and FIG. 13); dog GHRH plasmid, pAV0235 (SEQ ID NO:26 and FIG. 8); cat GHRH plasmid, pAV0238 (SEQ ID NO:28 and FIG. 10); horse GHRH plasmid, pAV0249 (FIG. 14); human GHRH plasmid, pAV0243 (SEQ ID NO:32 and FIG. 15); mouse GHRH plasmid, pAV0248 (SEQ ID NO:34 and FIG. 17); or rat GHRH plasmid, pAV0218 (SEQ ID NO:35 and FIG. 18). The studies described herein in "Examples" have included groups treated with different quantities of a wt-porcine GHRH plasmid, pAV0124 (SEQ ID NO:33 and FIG. 16). The therapeutic encoded gene for such optimized plasmids may also include optimized nucleic acid sequences that encode modified GHRH molecules or functional biological equivalents thereof.

Example 2

Methods in Animal Subject

Animals and Dietary Protocol—A total of 37 pigs were studies (n=11, 16, and 10 per study, respectively). Seven-day-old, mixed breed (Large White×Hampshire×Duroc) castrated barrows (Texas Department of Criminal Justice, Huntsville, Tex.) were obtained and transferred to the CNRC research facility where they were housed individually in environmentally controlled rooms at 28-30° C.

Upon arrival at the facility, the piglets were fed ad libitum with a milk replacer formula (250 g protein (2.5% lysine), 100 g fat, 2879 kcal ME per kg dry matter, mixed 1 part solids to 4 parts water; Soweena Litter Life; Merrick, Middleton, Wis.). After 2 to 3 days, the formula was mixed gradually with increasing quantities of a high protein feed (240 g protein (1.52% lysine), 63 g fat; 3408 kcal per kg dry matter; Producers Cooperative Association, Bryan, Tex.). From 14 days of age only the dry feed was provided. The study was conducted in accordance with the National Research Council's *Guide for the Care and Use of Laboratory Animals* and was approved by the Animal Care and Use Committee of Baylor College of Medicine.

Experimental Design—Piglets were randomly assigned to one of five treatment groups (n=5-9 per group), ensuring that the average weights of the control and treatment groups at 9 days of age were all within ±5% of each other. Three groups were administered one single injection of the wt-porcine GHRH plasmid at 10 d of age, a fourth group was administered daily recombinant porcine GH ("pGH") injections beginning at 14 d of age (to coincide with the anticipated time at which GHRH expression would be fully established), and a negative control group was administered at 10 d of age a plasmid construct that expresses β-galactosidase. From the fourth to the eleventh day of the experiment (14 to 21 d of age) the piglets were fed the 24% protein diet at 10% of the average body weight of the GH-treated animals. The feed was given in two feedings daily. For the subsequent two weeks, all piglets were fed the equivalent of 8% of the average body weight of the GH-treated pigs, and this was decreased to 6% of their average body weight for the remaining five weeks of the study—this food supply corresponds to approximately 85% of the normal ad libitum food intake. Once a day, any leftover and spilled food was weighed and subtracted from the amount administered to give an approximate measure of intake. Animals had ad libitum access to water at all times. Because the groups of piglets were weight-matched at the start of the study, the feeding protocol was designed to pair-feed the animals to the GH-treated group. Piglets were weighed twice a week, at which time the food intake was adjusted.

Body composition was measured by dual x-ray absorptiometry (DXA) at 10 d of age, and on day 52 of the study. Blood was collected by jugular puncture before the first morning feed on days 0, 7, 28, 35, 40, 49, and 54 for measurement of serum hormone and chemistry levels, although there was insufficient serum to perform all measurements at all time ages. On experiment day 54, the animals were killed by captive bolt followed by exsanguinations. Internal organs (heart, lungs, intestine, liver, kidneys, and spleen) were quantitatively dissected and weighed, and finally carcass (whole body with internal organs and head removed) weight was determined.

Plasmid administration and electroporation—The procedure that we had previously determined would result in the maximal sustained expression of the cDNA was used for this study (Draghia-Akli et al., 2003b). Briefly, piglets were fasted overnight and anesthetized (ketamine, 20 mg/kg; acepromazine, 0.8 mg/kg; i.m.). The appropriate plasmid preparation was injected through the intact skin into the sternocranialis muscle using a 21-gauge needle. The pGHRH groups were administered one of three different doses: 0.1 mg, 1 mg, or 3 mg. In Study 3, an initial dose of 0.1 mg was administered at 10 d of age, and an additional 1 mg dose was administered after 28 days. Electroporation was performed using the ADViSYS EKD System (as described in (Khan et al., 2003)) at settings of 1 Amp, 52 msec pulse, 1 sec between pulses, with 120 sec between plasmid injection and electroporation.

Porcine GH (pGH) injections—Lyophilized porcine GH ("pGH") (National Hormone and Peptide Program, Torrance, Calif.) was rapidly weighed, aliquoted into sealed glass vials, and frozen in a glass vacuum desiccator at −20° C. The amount of pGH to be injected over a week was calculated for each animal, based on a daily dose of 0.15 mg/(kg·day) and body weight at the start of the week. The pGH was reconstituted under aseptic conditions in filter sterilized 0.1% (w/v) IgG-free bovine serum albumin (Sigma, St. Louis, Mo.). In order to avoid repeated freeze-thawing, after reconstitution the volume required for one week was aliquoted into smaller volumes sufficient to inject the entire group (one aliquot for each of the twice daily injections for 7 days). The pGH was administered at a constant dose of 0.15 mg/kg day injected twice a day, everyday, as an IM injection in the sternocranialis muscle from 14 d of age until the end of the study.

Body composition assessment—Body composition measurements were performed by DXA on anesthetized piglets on day 0, before the plasmid injection, and again after 53 days. Measurements were performed on a Hologic AdelphiA DXA instrument. Scans were translated into composition measurements using calibration equations derived for piglets (Chauhan et al., 2003). Body composition of the piglets on day 4 of the study, i.e. at the start of the pGH administration protocol, was interpolated from the relationships between lean mass or fat and body weight on experimental day 0; bone mineral content was assumed to be the same as day 0. Changes in lean body mass, fat, and bone mineral content were calculated by subtraction of day 4 values from the final values for each individual animal.

Serum Hormones—Serum IGF-I and IGFBP-3 concentrations were measured using heterologous human immunoradiometric assay kits (Diagnostic System Labs, Webster Tex.). The inter- and intra-assay variability for IGF-I were both 4%; cross-reactivity of human IGF-I antibody for porcine IGF-I is 100%. All IGFBP-3 determinations were performed in one batch, and the intra-assay coefficient of variation for was 2%.

Insulin was measured using a heterologous human radioimmunoassay (Linco Research Inc., St. Charles, Mo.). The sensitivity level of the assay was 2 μU/mL, and the intra-assay and inter-assay variation was 3.2% and 3.9%, respectively.

Serum Chemistries—Blood collected by jugular puncture was allowed to clot aliquoted and stored at −80° C. until analyzed. Samples from the first 2 batches of pigs were analyzed for alanine aminotransferase, total bilirubin, alkaline phosphatase, total protein, albumin, globulin, cholesterol, blood urea nitrogen, creatinine, phosphorus, calcium, glucose, sodium, potassium, chloride, and creatine phosphokinase (Antech Diagnostics, Irvine, Calif.).

Statistics—Statistics were analyzed using Minitab. For all responses, ANOVA using a general linear model was used to determine if there were differences in responses among the three batches of pigs. As this was not the case, data for all three batches were grouped. Similarly, among wt-porcine GHRH plasmid-treated groups, outcome variables were evaluated to determine if there was an effect of dose. In the absence of a dose effect, all data for wt-porcine GHRH plasmid-treated pigs were combined. Specific P values were obtained using Students t-test or ANOVA analysis (P<0.05 was set as the level of statistical significance). Values are reported as means±SEM unless specified otherwise.

Example 3

Plasmid GHRH-Treated Pigs Exhibit Lower Cholesterol Levels

Treating subjects having elevated cholesterol levels who do not have clinical evidence of coronary heart disease ("CHD") is called primary prevention. The rationale for this approach is based upon epidemiologic data documenting a continuous, graded relationship between the total plasma cholesterol concentration and CHD events and mortality. The causal role of cholesterol in this relationship is suggested by clinical trials that have demonstrated that targeted lowering of cholesterol in patients may reduce CHD morbidity.

Body weight—As designed, the average starting weight of the 5 groups of pigs at 10 d of age and among batches were not significantly different (mean: 3.02±0.42 (1 SD).kg). Because neither batch nor starting weight contributed to the variance in weight gain, data for the three batches were pooled and analyzed together. FIG. 1 illustrates the average weight growth curves for the three treatment groups. The average daily rates of weight for the entire study were similar among all wt-porcine GHRH groups (0.1 mg wt-porcine GHRH: 443±6 g/d; 1 mg wt-porcine GHRH: 432±12 g/d; 3 mg wt-porcine GHRH: 440±16 g/d), and significantly higher than for controls, but lower than for the pGH treated pigs. It is evident from FIG. 1, however, that the difference in weight between the wt-porcine GHRH- and pGH-treated pigs emerged after 6 weeks of treatment. Indeed, the average daily gains for the first 6 weeks of treatment were the same (444±9 and 449±15 g/d, respectively). The corresponding gains between 6 weeks and the end of the study were 424±11 and 511±18 g/d for wt-porcine GHRH and pGH-treatments, respectively (P<0.05); the average daily gain of the controls over the same period was 392±17 g/d and not different from the wt-porcine GHRH-treated group (P<0.05). When the growth rate among the wt-porcine GHRH groups was compared for this period, there was a significant dose effect (P<0.04). The average daily gain for the pigs that received the 3 mg dose (464±26 g/d) was significantly higher than for the two lower doses (424±11 and 402±10 g/d, respectively, P<0.05), and not different from the value for the pGH-treated pigs.

Body composition—The differences in weight gain were almost entirely due to the effects of the treatments on the accretion of lean body mass (FIG. 2), and was greatest for the pGH-treated pigs, and the least in control pigs. There was a tendency for fat deposition to be slightly lower in the pGH-treated pigs (P=0.062). By the end of the study the fat-free mass (FFM) of wt-porcine GHRH plasmid-treated was 10% higher than controls, whereas the FFM of pGH-treated pigs was 20% higher than for controls, and both treated groups were significantly leaner than controls (FIG. 3). Measurements of back-fat thickness reflected the differences in the % body fat. pGH-treated animals had a significant decrease in both medial and distal backfat as compared to controls (medial, P=0.006; distal, P=0.0009). Plasmid GHRH-treated animals also exhibited significant decreases in both medial and distal backfat as compared to controls (medial, P=0.02; distal, P=0.004). There were no differences among groups in the daily accretion rate of bone mineral content (BMC) and in bone mineral density (BMD) at the end of the study. BMD increased from a value of 0.237±0.016 g/mm$^2$ at 10 d of age to 0.530±0.011 g/mm$^2$ at 9 weeks of age (P<0.001). When expressed relative to body weight, BMC was greatest in control and least in pGH-treated pigs.

Total dissected organ weights corrected for body weight were by large not different among treatment groups (FIG. 3). Among individual organs, the kidneys demonstrated a treatment response, and were significantly heavier in the pGH-treated animals versus control animals (P<0.03). The difference between carcass weight and body weight includes all the organs and the head; this component was significantly heavier in the pGH-treated pigs (7.05±0.17 kg, P<0.003) than either the control (6.51±0.18 kg) or wt-porcine GHRH plasmid-treated animals (6.22±0.14 kg), indicating that the pGH treatment induces a certain degree of unwanted organomegaly.

Serum IGF-I, IGFBP-3, insulin, and ACTH levels—Serum IGF-I and IGFBP-3 were measured on samples collected on experimental days 0, 7, 28 and 49 only. No batch or pGHRH plasmid dose effects were identified; data are summarized in FIG. 4. IGF-I concentration increased with age (P<0.001), and there was a significant treatment×time interaction (P<0.001). Differences among treatments were evident at 28 d of treatment when IGF-I levels were significantly higher in wt-porcine GHRH plasmid- and pGH-treated pigs than controls (P<0.03). However, by 49 days only the values of pGH-treated pigs were higher than for controls (P<0.001). For IGFBP-3 values, increased with age (P<0.001), but there was no treatment effect. Insulin and ACTH levels were measured at the beginning and d 49 of the study, were not changed by treatment and were within the normal range.

Serum biochemistry values—Serum biochemistry was measured at d 0, 28-35 and at the end of the study; values were within the normal range and not different between groups, unless specified herein as of treatment group and time point. As depicted in FIG. 5, total protein was significantly increased in pGH-treated animals as compared to controls (P=0.015). BUN and creatinine were within normal values for animals in all groups, indicating that the pGH and plasmid wt-porcine GHRH treatments did not adversely affect kidney function; BUN levels were different among all groups, with the difference between pGH and controls significant statistically (P<0.02, and wt-porcine GHRH-treated animals, P<0.06 vs. pGH-treated animals, and P<0.06 vs. controls). Serum sodium and chloride values were normal among the groups, indicating that the electrolyte levels were unchanged with treatment. Glucose levels were decreased in GHRH-treated pigs as compared to controls (P=0.013). Hemoglobin was significantly increased in GHRH-treated pigs at d 28-35 after treatment (12.5±0.4 at d 28-35 versus 11.2±0.4 g/L at d 0, P<0.04) but within normal values for pigs. While total white blood cells were decreased with GH treatment as compared to pGHRH treatment (13.6±0.4×10$^6$ at d 28-35 versus 17±1×10$^6$ cells/mL at d 0, P<0.02), the relative proportion and absolute values of circulating lymphocytes increased with treatment 9.4±0.5×10$^6$ at d 28-35 versus 6.2±0.9×10$^6$ at d 0, P<0.05).

Cholesterol. Animals in the GH-treated group exhibited significantly higher cholesterol levels than the GHRH-treated animals (P=0.04), while the control group had intermediate values. The difference in cholesterol values was calculated at 21% lower versus the group receiving pGH, and 12% lower versus the controls that received a restrictive diet at 85% of their normal ad libidum food intake. These levels are within the therapeutic range for patients affected by high cholesterol. This indicates that delivering a nucleic acid expression construct that encodes a growth-hormone-releasing-hormone ("GHRH") into a tissue of the subject can be used to lower cholesterol values in subject having elevated cholesterol levels and used as primary prevention in subjects having normal cholesterol levels. Tests were products of Antech Diagnostics (Irvine, Calif.), Test Code Test Name: SA010 Superchem which tests for: Albumin, Alk Phos, ALT, Amylase, AST, BUN, Calcium, Chloride, Cholesterol, CPK, Creatinine, GGT, Globulin, Glucose, Lipase, Magnesium, Osmolality, Phosphorus, Potassium, Sodium, Total Bilirubin, Total Protein, Triglyceride.

REFERENCES CITED

The entire content of each of the following U.S. patent documents and published references is hereby incorporated by reference.
U.S. Patent Documents
U.S. Pat. No. 5,847,066 issued on Dec. 8, 1998 with Coy et al. listed as inventors.
U.S. Pat. No. 5,846,936 issued on Dec. 8, 1998 with Felix et al. listed as inventors.
U.S. Pat. No. 5,792,747 issued on Aug. 11, 1998 with Schally et al. listed as inventors.
U.S. Pat. No. 5,776,901 issued on Jul. 7, 1998 with Bowers et al. listed as inventors.
U.S. Pat. No. 5,756,264 issued on May 26, 1998 with Schwartz et al. listed as inventors.
U.S. Pat. No. 5,696,089 issued on Dec. 9, 1997 with Felix et al. listed as inventors.
U.S. Pat. No. 5,486,505 issued on Jan. 23, 1996 with Bowers et al. listed as inventors.
U.S. Pat. No. 5,292,721 issued on Mar. 8, 1994 with Boyd et al. listed as inventors.
U.S. Pat. No. 5,137,872 issued on Aug. 11, 1992 with Seely et al. listed as inventors.
U.S. Pat. No. 5,134,210 issued on Jul. 28, 1992 with Boyd et al. listed as inventors.
U.S. Pat. No. 5,084,442 issued on Jan. 28, 1992 with Felix et al. listed as inventors.
U.S. Pat. No. 5,061,690 issued on Oct. 29, 1991 with Kann et al. listed as inventors.
U.S. Pat. No. 5,036,045 issued on Jul. 30, 1991 with Thorner listed as the inventor.
U.S. Pat. No. 5,023,322 issued on Jun. 11, 1991 with Kovacs et al. listed as inventors.
U.S. Pat. No. 4,839,344 issued on Jun. 13, 1989 with Bowers et al. listed as inventors.
U.S. Pat. No. 4,410,512 issued on Oct. 18, 1983 with Bowers et al. listed as inventors.
U.S. Pat. No. RE33,699 issued on Sep. 24, 1991 with Drengler listed as the inventor.
U.S. Pat. No. 4,833,166 issued on May 23, 1989 with Grosvenor et al. listed as inventors.
U.S. Pat. No. 4,228,158 issued on Oct. 14, 1980 with Momany et al. listed as inventors.
U.S. Pat. No. 4,228,156 issued on Oct. 14, 1980 with Momany et al. listed as inventors.
U.S. Pat. No. 4,226,857 issued on Oct. 7, 1980 with Momany et al. listed as inventors.
U.S. Pat. No. 4,224,316 issued on Sep. 23, 1980 with Momany et al. listed as inventors.
U.S. Pat. No. 4,223,021 issued on Sep. 16, 1980 with Momany et al, listed as inventors.
U.S. Pat. No. 4,223,020 issued on Sep. 16, 1980 with Momany et al. listed as inventors.
U.S. Pat. No. 4,223,019 issued on Sep. 16, 1980 with Momany et al. listed as inventors.
U.S. Pat. No. 5,702,359 titled "Needle electrodes for mediated delivery of drugs and genes," issued on Dec. 30, 1997, with Hofmann, et al., listed as inventors.
U.S. Pat. No. 5,439,440 titled "Electroporation system with voltage control feedback for clinical applications," issued on Aug. 8, 1995 with Hofmann listed as inventor.
PCT application WO/96/12520 titled "Electroporetic Gene and Drug Therapy by Induced Electric Fields," published on May 5, 1996 with Hofmann et al., listed as inventors.
PCT application WO/96/12006 titled "Flow Through Electroporation Apparatus and Method," published on Apr. 25, 1996 with Hofmann et al., listed as inventors.
PCT application WO/95/19805 titled "Electroporation and Iontophoresis Apparatus and Method For insertion of Drugs and genes into Cells," published on Jul. 27, 1995 with Hofmann listed as inventor.
PCT application WO/97/07826 titled "In Vivo Electroporation of Cells," published on Mar. 6, 1997, with Nicolau et al., listed as inventors.

REFERENCE LIST

Acsadi, G., G. Dickson, D. R. Love, A. Jani, F. S. Walsh, A. Gurusinghe, Wolff, J A, and K. E. Davies. 1991. Human Dystrophin Expression in Mdx Mice After Intramuscular Injection of DNA Constructs. Nature 352:815-818.
Ahn, C. W., C. S. Kim, J. H. Nam, H. J. Kim, J. S. Nam, J. S. Park, E. S. Kang, B. S. Cha, S. K. Lim, K. R. Kim, H. C. Lee, and K. B. Huh. 2006. Effects of Growth Hormone on Insulin Resistance and Atherosclerotic Risk Factors in Obese Type 2 Diabetic Patients With Poor Glycaemic Control. Clin. Endocrinol. (Oxf) 64:444-449.
Aihara, H. and J. Miyazaki. 1998. Gene Transfer Into Muscle by Electroporation in vivo. Nat. Biotechnol. 16:867-870.
Akhtar, S. 2005. Non-Viral Cancer Gene Therapy: Beyond Delivery, Gene Ther.
Almendro, N., T. Bellon, C. Rius, P. Lastres, C. Langa, A. Corbi, and C. Bernabeu. 1996. Cloning of the Human Platelet Endothelial Cell Adhesion Molecule-1 Promoter and its Tissue-Specific Expression. Structural and Functional Characterization. J. Immunol. 157:5411-5421.
Auchtung, T. L., D. S. Buchanan, C. A. Lents, S. M. Barao, and G. E. Dahl. 2001. Growth Hormone Response to Growth Hormone-Releasing Hormone in Beef Cows Divergently Selected For Milk Production. J. Anim Sci. 79:1295-1300.

Babiuk, L. A., R. Pontarollo, S. Babiuk, B. Loehr, and Van Drunen Littel-Van Den Hurk. 2003. Induction of Immune Responses by DNA Vaccines in Large Animals. Vaccine 21:649-658.

Blethen, S. L. and A. C. Rundle. 1996. Slipped Capital Femoral Epiphysis in Children Treated With Growth Hormone. A Summary of the National Cooperative Growth Study Experience. Horm. Res. 46:113-116.

Boguszewski, C. L., L. H. Meister, D. C. Zaninelli, and R. B. Radominski. 2005. One Year of GH Replacement Therapy with a Fixed Low-Dose Regimen Improves Body Composition, Bone Mineral Density and Lipid Profile of GH-Deficient Adults. Eur. J Endocrinol. 152:67-75.

Bohlen, P., F. Esch, P. Brazeau, N. Ling, and R. Guillemin. 1983. Isolation and Characterization of the Porcine Hypothalamic Growth Hormone Releasing Factor. Biochem. Biophys. Res. Commun. 116:726-734.

Bollerslev, J., J. Hallen, K. J. Fougner, A. P. Jorgensen, C. Kristo, H. Fagertun, O. Gudmundsen, P. Burman, and T. Schreiner. 2005. Low-Dose GH Improves Exercise Capacity in Adults with GH Deficiency: Effects of a 22-Month Placebo-Controlled, Crossover Trial. Eur. J Endocrinol. 153:379-387.

Boshart, M., F. Weber, G. Jahn, K. Dorsch-Hasler, B. Fleckenstein, and W. Schaffner. 1985. A Very Strong Enhancer Is Located Upstream of an Immediate Early Gene of Human Cytomegalovirus. Cell 41:521-530.

Bramnert, M., M. Segerlantz, E. Laurila, J. R. Daugaard, P. Manhem, and L. Groop. 2003. Growth Hormone Replacement Therapy Induces Insulin Resistance By Activating the Glucose-Fatty Acid Cycle. J. Clin. Endocrinol. Metab 88:1455-1463.

Brown, P. A., W. C. Davis, and R. Draghia-Akli. 2004. Immune Enhancing Effects of Growth Hormone Releasing Hormone Delivered by Plasmid Injection and Electroporation. Molecular Therapy 10:644-651.

Carbonelli, D. L., E, Corley, M. Seigelchifer, and J. Zorzopulos. 1999. A Plasmid Vector for Isolation of Strong Promoters in *Escherichia Coli*. Fems Microbiol. Lett. 177:75-82.

Ceda, G. P., R. G. Davis, R. G. Rosenfeld, and A. R. Hoffman. 1987. The Growth Hormone (GH)-Releasing Hormone (GHRH)-GH-Somatomedin Axis: Evidence for Rapid Inhibition of GHRH-Elicited GH Release by Insulin-Like Growth Factors I and II. Endocrinology 120:1658-1662.

Chandler, S. D., A. Mayeda, J. M. Yeakley, A. R. Krainer, and X. D. Fu. 1997. RNA Splicing Specificity Determined by the Coordinated Action of RNA Recognition Motifs in Sr Proteins. Proc. Natl. Acad. Sci. U.S.A 94:3596-3601.

Chauhan, S., W. W. Koo, M. Hammami, and E. M. Hockman. 2003. Fan Beam Dual Energy X-Ray Absorptiometry Body Composition Measurements in Piglets. J. Am. Coll. Nutr. 22:408-414.

Chevalier, R. L., S. Goyal, A. Kim, A. Y. Chang, D. Landau, and D. Leroith. 2000. Renal Tubulointerstitial Injury from Ureteral Obstruction in the Neonatal Rat Is Attenuated by IGF-1. Kidney Int. 57:882-890.

Chung, C. S., T. D. Etherton, and J. P. Wiggins. 1985. Stimulation of Swine Growth by Porcine Growth Hormone. J. Anim Sci. 60:118-130.

Clark, R. G., L. M. Carlsson, and I. C. Robinson. 1988. Growth Hormone (GH) Secretion in the Conscious Rat: Negative Feedback of GH on its Own Release. J Endocrinol. 119:201-209.

Clark, R. G. and I. C. Robinson. 1985. Growth Induced By Pulsatile Infusion of An Amidated Fragment of Human Growth Hormone Releasing Factor in Normal and GHRF-Deficient Rats. Nature 314:281-283.

Cocea, L. 1997. Duplication of a Region in the Multiple Cloning Site of a Plasmid Vector to Enhance Cloning-Mediated Addition of Restriction Sites to a DNA Fragment. Biotechniques 23:814-816.

Colao, A., A. Cuocolo, C. Di Somma, G. Cerbone, A. M. Della Morte, E. Nicolai, R. Lucci, M. Salvatore, and G. Lombardi. 1999. Impaired Cardiac Performance in Elderly Patients with Growth Hormone Deficiency. J. Clin. Endocrinol. Metab 84:3950-3955.

Colao, A., C. D. Somma, M. C. Savanelli, M. D. Leo, and G. Lombardi. 2006. Beginning to End: Cardiovascular Implications of Growth Hormone (GH) Deficiency and GH Therapy. Growth Horm. IGF. Res. 16 Suppl:41-48.

Cummings, D. E. and G. R. Merriam. 1999. Age-Related Changes in Growth Hormone Secretion: Should the Somatopause Be Treated? Semin, Reprod. Endocrinol. 17:311-325.

Dahl, G. E., L. T. Chapin, M. S. Allen, W. M. Moseley, and H. A. Tucker. 1991. Comparison of Somatotropin and Growth Hormone-Releasing Factor on Milk Yield, Serum Hormones, and Energy Status. J. Dairy Sci. 74:3421-3428.

Dai, B., H. Wu, E. Holthuizen, and P. Singh. 2001. Identification of A Novel Cis Element Required For Cell Density-Dependent Down-Regulation of Insulin-Like Growth Factor-2 P3 Promoter Activity in Caco2 Cells. J. Biol. Chem. 276:6937-6944.

Danko, I. and J. A. Wolff. 1994. Direct Gene Transfer Into Muscle. Vaccine 12:1499-1502

Darquet, A. M., B. Cameron, P. Wils, D. Scherman, and J. Crouzet. 1997. A New DNA Vehicle For Nonviral Gene Delivery: Supercoiled Minicircle. Gene Ther. 4:1341-1349.

Darquet, A. M., R. Rangara, P. Kreiss, B. Schwartz, S, Naimi, P. Delaere, J. Crouzet, and D. Scherman. 1999. Minicircle: An Improved DNA Molecule For in Vitro and in Vivo Gene Transfer. Gene Ther. 6:209-218.

Davis, H. L., R. G. Whalen, and B. A. Demeneix. 1993. Direct Gene Transfer Into Skeletal Muscle in Vivo: Factors Affecting Efficiency of Transfer and Stability of Expression. Human Gene Therapy 4:151-159.

Dolnik, V., M. Novotny, and J. Chmelik. 1993. Electromigration Behavior of Poly-(L-Glutamate) Conformers in Concentrated Polyacrylamide Gels. Biopolymers 33:1299-1306.

Dornonville De La, C. C., A. Lindqvist, E. Egecioglu, Y. C. Tung, V. Surve, C. Ohlsson, J. O. Jansson, C. Erlanson-Albertsson, S. L. Dickson, and R. Hakanson. 2005. Ghrelin Treatment Reverses the Reduction In Weight Gain and Body Fat In Gastrectomised Mice. Gut 54:907-913.

Dorsch-Hasler, K., G. M. Keil, F. Weber, M. Jasin, W. Schaffner, and U. H. Koszinowski. 1985. A Long and Complex Enhancer Activates Transcription of the Gene Coding For the Highly Abundant Immediate Early Mrna In Murine Cytomegalovirus. Proc. Natl. Acad. Sci. U.S.A 82:8325-8329.

Draghia-Akli, R., K. K. Cummings, A. S. Khan, P. A. Brown, and R. H. Carpenter. 2003a. Effects of Plasmid-Mediated Growth Hormone Releasing Hormone Supplementation In Young Healthy Beagle Dogs. Journal of Animal Science 81:2301-2310.

Draghia-Akli, R., K. M. Ellis, L. A. Hill, P. B. Malone, and M. L. Fiorotto. 2003b. High-Efficiency Growth Hormone Releasing Hormone Plasmid Vector Administration Into Skeletal Muscle Mediated By Electroporation In Pigs. Faseb J 17:526-528.

Draghia-Akli, R. and M. L. Fiorotto. 2004. A New Plasmid-Mediated Approach To Supplement Somatotropin Production In Pigs. Journal of Animal Science 82:E264-E269.

Draghia-Akli, R., M. L. Fiorotto, L. A. Hill, P. B. Malone, D. R. Deaver, and R. J. Schwartz. 1999. Myogenic Expression of An Injectable Protease-Resistant Growth Hormone-Releasing Hormone Augments Long-Term Growth In Pigs. Nat. Biotechnol. 17:1179-1183.

Draghia-Akli, R., K. A. Hahn, G. K. King, K. Cummings, and R. H. Carpenter. 2002a. Effects of Plasmid Mediated Growth Hormone Releasing Hormone In Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery In Animals. Technology In Cancer Research & Treatment 1:365-371.

Draghia-Akli, R., X. G. Li, and R. J. Schwartz. 1997. Enhanced Growth By Ectopic Expression of Growth Hormone Releasing Hormone Using An Injectable Myogenic Vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced Animal Growth Via Ligand-Regulated GHRH Myogenic-Injectable Vectors. Faseb J. 16:426-428.

Dubreuil, P., D. Petitclerc, G. Pelletier, P. Gaudreau, C. Farmer, Mowles, T f, and P. Brazeau. 1990. Effect of Dose and Frequency of Administration of A Potent Analog of Human Growth Hormone-Releasing Factor On Hormone Secretion and Growth In Pigs. Journal of Animal Science 68:1254-1268.

Duck, S. C. and R. Rapaport. 1999. Long-Term Treatment With GHRH [1-44] Amide In Prepubertal Children With Classical Growth Hormone Deficiency. J. Pediatr. Endocrinol. Metab 12:531-536.

Duck, S. C., H. P. Schwarz, G. Costin, R. Rapaport, S. Arslanian, A. Hayek, M. Connors, and J. Jaramillo. 1992. Subcutaneous Growth Hormone-Releasing Hormone Therapy In Growth Hormone-Deficient Children: First Year of Therapy. J Clin Endocrinol Metab 75:1115-1120.

Ehlers, M. R. 2001. Recombinant Human GHRH(1-44)Nh2: Clinical Utility and Therapeutic Development Program. Endocrine. 14:137-141.

El-Aneed, A. 2004. An Overview of Current Delivery Systems In Cancer Gene Therapy. J Control Release 94:1-14.

Esch, F. S., P. Bohlen, N. C. Ling, P. E. Brazeau, W. B. Wehrenberg, M. O. Thorner, M. J. Cronin, and R. Guillemin. 1982. Characterization of A 40 Residue Peptide From A Human Pancreatic Tumor With Growth Hormone Releasing Activity. Biochem Biophy Res Comm 109:152-158.

Etherton, T. D., J. P. Wiggins, C. M. Evock, C. S. Chung, J. F. Rebhun, P. E. Walton, and N. C. Steele. 1987. Stimulation of Pig Growth Performance By Porcine Growth Hormone: Determination of the Dose-Response Relationship. J. Anim Sci. 64:433-443.

Evans, W. S., M. L. Vance, D. L. Kaiser, R. P. Sellers, J. L. Borges, T. R. Downs, L. A. Frohman, J. Rivier, W. Vale, and M. O. Thorner. 1985. Effects of Intravenous, Subcutaneous, and Intranasal Administration of Growth Hormone (GH)-Releasing Hormone-40 on Serum GH Concentrations in Normal Men. Journal of Clinical Endocrinology & Metabolism 61:846-850.

Fewell, J. G., F. Maclaughlin, V. Mehta, M. Gondo, F. Nicol, E. Wilson, and L. C. Smith. 2001. Gene Therapy For the Treatment of Hemophilia B Using Pinc-Formulated Plasmid Delivered To Muscle With Electroporation. Mol. Ther. 3:574-583.

Frederickson, R. M., B. J. Carter, and A. M. Pilaro. 2003. Nonclinical Toxicology In Support of Licensure of Gene Therapies. Mol. Ther. 8:8-10.

Fryer, A. D. and D. B. Jacoby. 1993. Effect of Inflammatory Cell Mediators On M2 Muscarinic Receptors In the Lungs. Life Sci. 52:529-536.

Fujikawa, K., H. Fukuoka, K. S. Alam, H. Yoshizato, S. Higashimoto, H. Soya, M. Tanaka, and K. Nakashima. 2000. Subcutaneously Administered Prolactin and 20k hGH, But Not rGH Or 22k hGH, Prevent Restraint Stress-Induced Gastric Ulcers In Rats. Endocr. J 47 Suppl:S49-52:S49-S52.

Gehl, J., T. Skovsgaard, and L. M. Mir. 1998. Enhancement of Cytotoxicity By Electropermeabilization: An Improved Method For Screening Drugs. Anticancer Drugs 9:319-325.

Gehl, J., T. H. Sorensen, K. Nielsen, P. Raskmark, S. L. Nielsen, T. Skovsgaard, and L. M. Mir. 1999. In Vivo Electroporation of Skeletal Muscle: Threshold, Efficacy and Relation To Electric Field Distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and. 1995. The Insulin Gene Promoter. A Simplified Nomenclature. Diabetes 44:1002-1004.

Ghigo, E., E. Arvat, F. Broglio, R. Giordano, L. Gianotti, G. Muccioli, M. Papotti, A. Graziani, G. Bisi, R. Deghenghi, and F. Carnanni. 1999. Endocrine and Non-Endocrine Activities of Growth Hormone Secretagogues in Humans. Horm. Res. 51 Suppl 3:9-15.

Gopinath, R. and T. D. Etherton. 1989a. Effects of Porcine Growth Hormone on Glucose Metabolism of Pigs: I. Acute and Chronic Effects on Plasma Glucose and Insulin Status. J. Anim Sci. 67:682-688.

Gopinath, R. and T. D. Etherton. 1989b. Effects of Porcine Growth Hormone on Glucose Metabolism of Pigs: II. Glucose Tolerance, Peripheral Tissue Insulin Sensitivity and Glucose Kinetics. J. Anim Sci. 67:689-697.

Guillemin, R., P. Brazeau, P. Bohlen, F. Esch, N. Ling, and W. B. Wehrenberg. 1982. Growth Hormone-Releasing Factor From A Human Pancreatic Tumor That Caused Acromegaly. Science 218:585-587.

Heller, R., M. J. Jaroszeski, L. F. Glass, J. L. Messina, D. P. Rapaport, R. C. Deconti, N. A. Fenske, R. A. Gilbert, L. M. Mir, and D. S. Reintgen. 1996. Phase I/II Trial For the Treatment of Cutaneous and Subcutaneous Tumors Using Electrochemotherapy. Cancer 77:964-971.

Horlick, R. A. and P. A. Benfield. 1989. The Upstream Muscle-Specific Enhancer of the Rat Muscle Creatine Kinase Gene Is Composed of Multiple Elements. Mol. Cell. Biol. 9:2396-2413.

Inouye, C., P. Remondelli, M. Karin, and S. Elledge. 1994. Isolation of a cDNA Encoding a Metal Response Element Binding Protein Using A Novel Expression Cloning Procedure: the One Hybrid System. DNA Cell Biol. 13:731-742.

Inouye, S., A. Nakazawa, and T. Nakazawa. 1985. Determination of the Transcription Initiation Site and Identification of the Protein Product of the Regulatory Gene xylr for xyl Operons on the tol Plasmid. J. Bacteriol. 163:863-869.

Jaynes, J. B., J. E. Johnson, J. N. Buskin, C. L. Gartside, and S. D. Hauschka. 1988. The Muscle Creatine Kinase Gene Is Regulated By Multiple Upstream Elements, Including A Muscle-Specific Enhancer. Mol. Cell. Biol. 8:62-70.

Kawamoto, T., K. Makino, H. Niwa, H. Sugiyama, S. Kimura, M. Amemura, A. Nakata, and T. Kakunaga. 1988. Identification of the Human Beta-Actin Enhancer and Its Binding Factor. Mol. Cell. Biol. 8:267-272.

Kawamoto, T., K. Makino, S. Orita, A. Nakata, and T. Kakunaga. 1989. DNA Bending and Binding Factors of the Human Beta-Actin Promoter. Nucleic Acids Res. 17:523-537.

Khan, A. S., M. A. Pope, and R. Draghia-Akli. 2005. Highly Efficient Constant-Current Electroporation Increases in Vivo Plasmid Expression. DNA & Cell Biology 24:810-818.

Khan, A. S., L. C. Smith, R. V. Abruzzese, K. K. Cummings, M. A. Pope, P. A. Brown, and R. Draghia-Akli. 2003. Optimization of Electroporation Parameters For the Intramuscular Delivery of Plasmids In Pigs. DNA Cell Biol. 22:807-814.

Klamut, H. J., L. O. Bosnoyan-Collins, R. G. Worton, P. N. Ray, and H. L. Davis. 1996. Identification of A Transcriptional Enhancer Within Muscle Intron 1 of the Human Dystrophin Gene. Hum. Mol. Genet. 5:1599-1606.

Klamut, H. J., S. B. Gangopadhyay, R. G. Worton, and P. N. Ray. 1990. Molecular and Functional Analysis of the Muscle-Specific Promoter Region of the Duchenne Muscular Dystrophy Gene. Mol. Cell. Biol. 10: 193-205.

Kotler, D. P. 2000. Cachexia. Ann. Intern. Med. 133:622-634.

Kraus, J., M. Woltje, N. Schonwetter, and V. Hollt. 1998. Alternative Promoter Usage and Tissue Specific Expression of the Mouse Somatostatin Receptor 2 Gene. Febs Lett. 428:165-170.

Langenberg, C., J. Bergstrom, G. A. Laughlin, and E. Barrett-Connor. 2005. Ghrelin and the Metabolic Syndrome In Older Adults. J. Clin. Endocrinol. Metab 90:6448-6453.

Lareyre, J. J., T. Z. Thomas, W. L. Zheng, S. Kasper, D. E. Ong, M. C. Orgebin-Crist, and R. J. Matusik. 1999. A 5-Kilobase Pair Promoter Fragment of the Murine Epididymal Retinoic Acid-Binding Protein Gene Drives the Tissue-Specific, Cell-Specific, and Androgen-Regulated Expression of A Foreign Gene In the Epididymis of Transgenic Mice. J. Biol. Chem. 274:8282-8290.

Larsen, P. R., J. W. Harney, and D. D. Moore. 1986. Sequences Required For Cell-Type Specific Thyroid Hormone Regulation of Rat Growth Hormone Promoter Activity. J. Biol. Chem. 261:14373-14376.

Lee, S. H., W. Wang, S. Yajirna, P. A. Jose, and M. M. Mouradian. 1997. Tissue-Specific Promoter Usage In the D1a Dopamine Receptor Gene In Brain and Kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In Vivo Electrotransfer of the Cardiotrophin-1 Gene Into Skeletal Muscle Slows Down Progression of Motor Neuron Degeneration In Pmn Mice. Hum. Mol. Genet. 11:1615-1625.

Levenson, V. V., E. D. Transue, and I. B. Roninson. 1998. Internal Ribosomal Entry Site-Containing Retroviral Vectors With Green Fluorescent Protein and Drug Resistance Markers. Hum. Gene Ther. 9:1233-1236.

Li, C., S. Ke, Q. P. Wu, W. Tansey, N. Hunter, L. M. Buchmiller, L. Milas, C. Chamsangavej, and S. Wallace. 2000. Tumor Irradiation Enhances the Tumor-Specific Distribution of Poly(L-Glutamic Acid)-Conjugated Paclitaxel and Its Antitumor Efficacy. Clin. Cancer Res. 6:2829-2834.

Li, X., E. M. Eastman, R. J. Schwartz, and R. Draghia-Akli. 1999. Synthetic Muscle Promoters: Activities Exceeding Naturally Occurring Regulatory Sequences. Nat. Biotechnol. 17:241-245.

Lin, H., K. E. Yutzey, and S. F. Konieczny. 1991. Muscle-Specific Expression of the Troponin I Gene Requires Interactions Between Helix-Loop-Helix Muscle Regulatory Factors and Ubiquitous Transcription Factors. Mol. Cell. Biol. 11:267-280.

Lissett, C. A. and S. M. Shalet. 2000. Effects of Growth Hormone on Bone and Muscle. Growth Horm, IGF. Res. 10 Suppl B:S95-101

Liu, Y., H. Li, K. Tanaka, N. Tsumaki, and Y. Yamada. 2000. Identification of An Enhancer Sequence Within the First Intron Required For Cartilage-Specific Transcription of the Alpha2(Xi) Collagen Gene. J. Biol. Chem. 275:12712-12718.

Lucas, M. L., L. Heller, D. Coppola, and R. Heller. 2002. Il-12 Plasmid Delivery By In Vivo Electroporation For the Successful Treatment of Established Subcutaneous B16.F10 Melanoma. Mol. Ther. 5:668-675.

Lucas, M. L., M. J. Jaroszeski, R. Gilbert, and R. Heller. 2001. In Vivo Electroporation Using An Exponentially Enhanced Pulse: A New Waveform. DNA Cell Biol. 20:183-188.

Macejak, D. G. and P. Sarnow. 1991. Internal Initiation of Translation Mediated By the 5' Leader of A Cellular mRNA. Nature 353:90-94.

Matsubara, H., Y. Gunji, T. Maeda, K. Tasaki, Y. Koide, T. Asano, T. Ochiai, S. Sakiyama, and M. Tagawa. 2001. Electroporation-Mediated Transfer of Cytokine Genes Into Human Esophageal Tumors Produces Anti-Tumor Effects In Mice. Anticancer Res. 21:2501-2503.

Miklavcic, D., K. Beravs, D. Semrov, M. Cemazar, F. Demsar, and G. Sersa. 1998. The Importance of Electric Field Distribution For Effective In Vivo Electroporation of Tissues. Biophys. J 74:2152-2158.

Mulligan, K. and M. Schambelan. 2002. Anabolic Treatment With GH, IGF-I, Or Anabolic Steroids In Patients With Hiv-Associated Wasting. Int. J. Cardiol. 85:151-159.

Mumper, R. J., J. Wang, S. L. Klakamp, H. Nitta, K. Anwer, F. Tagliaferri, and A. P. Rolland. 1998. Protective Interactive Noncondensing (PINC) Polymers For Enhanced Plasmid Distribution and Expression In Rat Skeletal Muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In Vivo Gene Electroporation In Skeletal Muscle With Special Reference To The Duration of Gene Expression. Int. J. Mol. Med. 7:3742.

Nagaya, N., T. Itoh, S. Murakami, H. Oya, M. Uematsu, K. Miyatake, and K. Kangawa. 2005. Treatment of Cachexia With Ghrelin In Patients With COPD. Chest 128:1187-1193.

Narum, D. L., S. Kumar, W. O. Rogers, S. R. Fuhrmann, H. Liang, M. Oakley, A. Taye, B. K. Sim, and S. L. Hoffman. 2001. Codon Optimization of Gene Fragments Encoding *Plasmodium Falciparum* Merzoite Proteins Enhances DNA Vaccine Protein Expression and Immunogenicity In Mice. Infect. Immun. 69:7250-7253.

Nomoto, S., Y. Tatematsu, T. Takahashi, and H. Osada. 1999. Cloning and Characterization of The Alternative Promoter Regions of The Human Link2 Gene Responsible For Alternative Transcripts With Tissue-Specific Expression. Gene 236:259-271.

Ohlsson, H., S. Thor, and T. Edlund. 1991. Novel Insulin Promoter- and Enhancer-Binding Proteins That Discriminate Between Pancreatic Alpha- and Beta-Cells. Mol. Endocrinol. 5:897-904.

Otani, Y., Y. Tabata, and Y. Ikada. 1996. Rapidly Curable Biological Glue Composed of Gelatin and Poly(L-Glutamic Acid). Biomaterials 17:1387-1391.

Otani, Y., Y. Tabata, and Y. Ikada. 1998. Hemostatic Capability of Rapidly Curable Glues From Gelatin, Poly(L-Glutamic Acid), and Carbodiimide. Biomaterials 19:2091-2098.

Patil, S. D., D. G. Rhodes, and D. J. Burgess. 2005. DNA-Based Therapeutics and DNA Delivery Systems: A Comprehensive Review. AAPS. J 7:E61-E77.

Pech, M., C. D. Rao, K. C. Robbins, and S. A. Aaronson. 1989. Functional Identification of Regulatory Elements Within The Promoter Region of Platelet-Derived Growth Factor 2. Mol. Cell. Biol. 9:396-405.

Pelletier, J. and N. Sonenberg. 1988. Internal Initiation of Translation of Eukaryotic mRNA Directed By A Sequence Derived From Poliovirus RNA. Nature 334:320-325.

Phung, L. T., H. Inoue, V. Nou, H. G. Lee, R. A. Vega, N. Matsunaga, S. Hidaka, H. Kuwayama, and H. Hidari. 2000. The Effects of Growth Hormone-Releasing Peptide-2 (GHRP-2) on The Release of Growth Hormone and Growth Performance In Swine. Domest. Anim Endocrinol. 18:279-291.

Pinkert, C. A., D. M. Ornitz, R. L. Brinster, and R. D. Palmiter. 1987. An Albumin Enhancer Located 10 kb Upstream Functions Along With Its Promoter To Direct Efficient, Liver-Specific Expression In Transgenic Mice. Genes Dev. 1:268-276.

Pommier, S. A., P. Dubreuil, G. Pelletier, P. Gaudreau, T. F. Mowles, Brazeau, and P. 1990. Effect of A Potent Analog of Human Growth Hormone-Releasing Factor on Carcass Composition and Quality of Crossbred Market Pigs. Journal of Animal Science 68:1291-1298.

Potter, H., L. Weir, and P. Leder. 1984. Enhancer-Dependent Expression of Human Kappa Immunoglobulin Genes Introduced Into Mouse Pre-B Lymphocytes By Electroporation. Proc. Natl. Acad. Sci. U.S.A 81:7161-7165.

Prentice, H., R. A. Kloner, T. Prigozy, T. Christensen, L. Newman, Y. Li, and L. Kedes. 1994. Tissue Restricted Gene Expression Assayed By Direct DNA Injection Into Cardiac and Skeletal Muscle. Journal of Molecular & Cellular Cardiology 26:1393-1401.

Prud'homme, G. J., Y. Glinka, A. S. Khan, and R. Draghia-Akli. 2006. Electroporation-Enhanced Nonviral Gene Transfer For The Prevention Or Treatment of Immunological, Endocrine and Neoplastic Diseases. Curr. Gene Ther. 6:243-273.

Rahim, A. and S. M. Shalet. 1998. Does Desensitization To Hexarelin Occur? Growth Horm. IGF. Res. 8 Suppl B:141-143.

Satozawa, N., K. Takezawa, T. Miwa, S. Takahashi, M. Hayakawa, and H. Ooka. 2000. Differences In the Effects of 20 K- and 22 K-hGH on Water Retention In Rats. Growth Horm. IGF. Res. 10:187-192.

Schleim, K. D., T. Jacks, P. Cunningham, W. Feeney, E. G. Frazier, G. W. Niebauer, D. Zhang, H. Chen, R. G. Smith, and G. Hickey. 1999. Increases In Circulating Insulin-Like Growth Factor I Levels By the Oral Growth Hormone Secretagogue MK-0677 In the Beagle Are Dependent Upon Pituitary Mediation. Endocrinology 140:1552-1558.

Siejka, A., H. Lawnicka, J. Komorowski, T. Stepien, R. Krupinski, and H. Stepien. 2004. Effect of Growth Hormone-Releasing Hormone (GHRH) and GHRH Antagonist (MZ-4-71) on Interferon-Gamma Secretion From Human Peripheral Blood Mononuclear Cells In Vitro. Neuropeptides 38:35-39.

Skroch, P., C. Buchman, and M. Karin. 1993. Regulation of Human and Yeast Metallothionein Gene Transcription By Heavy Metal Ions. Prog. Clin. Biol. Res. 380:113-28:113-128.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. Pcor: A New Design of Plasmid Vectors For Nonviral Gene Therapy. Gene Ther. 6:1482-1488.

Sun, Y., P. Wang, H. Zheng, and R. G. Smith. 2004. Ghrelin Stimulation of Growth Hormone Release and Appetite Is Mediated Through the Growth Hormone Secretagogue Receptor. Proc. Natl. Acad. Sci. U.S.A 101:4679-4684.

Svensson, J. A. and B. Bengtsson. 1999. Clinical and Experimental Effects of Growth Hormone Secretagogues on Various Organ Systems. Horm. Res. 51 Suppl 3:16-20.

Terada, Y., H. Tanaka, T. Okado, S. Inoshita, M. Kuwahara, T. Akiba, S. Sasaki, and F. Marumo. 2001. Efficient and Ligand-Dependent Regulated Erythropoietin Production By Naked DNA Injection and In Vivo Electroporation. Am. J. Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic Growth-Hormone-Releasing Factor (GRF) Secretion Is A Rare Cause of Acromegaly: Plasma GRF Levels In 177 Acromegalic Patients. Journal of Clinical Endocrinology & Metabolism 59:846-849.

Thorner, M. O., M. L. Vance, W. S. Evans, R. M. Blizzard, A. D. Rogol, K. Ho, Leong, Da, J. L. Borges, M. J. Cronin, R. M. Macleod, and Et Al. 1986a. Physiological and Clinical Studies of GRF and GH. Recent Progress In Hormone Research 42:589-640.

Thorner, M. O., M. L. Vance, W. S. Evans, A. D. Rogol, J. Rivier, W. Vale, Blizzard 1986b. Clinical Studies With GHRH In Man. Hormone Research 24:91-98.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA Injection In Combination With Electroporation: A Novel Method For Vaccination of Farmed Ruminants. Scand. J. Immunol. 57:229-238.

Tone, C. M., D. M. Cardoza, R. H. Carpenter, and R. Draghia-Akli. 2004. Long-Term Effects of Plasmid-Mediated Growth Hormone Releasing Hormone In Dogs. Cancer Gene Ther. 11:389-396.

Tripathy, S. K., E. C. Svensson, H. B. Black, E. Goldwasser, M. Margalith, Hobart, P m, and J. M. Leiden. 1996. Long-Term Expression of Erythropoietin In the Systemic Circulation of Mice After Intramuscular Injection of A Plasmid DNA Vector. Proc. Natl. Acad. Sci. Usa 93:10876-10880.

Tronche, F., A. Rollier, I. Bach, M. C. Weiss, and M. Yaniv. 1989. the Rat Albumin Promoter: Cooperation With Upstream Elements Is Required When Binding of Apf/Hnfl To the Proximal Element Is Partially Impaired By Mutation Or Bacterial Methylation. Mol. Cell. Biol. 9:4759-4766.

Tronche, F., A. Rollier, P. Herbomel, I. Bach, S. Cereghini, M. Weiss, and M. Yaniv. 1990. Anatomy of the Rat Albumin Promoter. Mol. Biol. Med. 7:173-185.

Trudel, M. and F. Costantini. 1987. A 3' Enhancer Contributes To the Stage-Specific Expression of the Human Beta-Globin Gene. Genes Dev. 1:954-961.

Tsumaki, N., T. Kimura, K. Tanaka, J. H. Kimura, T. Ochi, and Y. Yamada. 1998. Modular Arrangement of Cartilage- and Neural Tissue-Specific Cis-Elements In the Mouse Alpha2(Xi) Collagen Promoter. J. Biol. Chem. 273:22861-22864.

Tsunekawa, B., M. Wada, M. Ikeda, H. Uchida, N. Naito, and M. Honjo. 1999. the 20-Kilodalton (kDa) Human Growth Hormone (hGH) Differs From the 22-kDa hGH In the Effect on the Human Prolactin Receptor. Endocrinology 140:3909-3918.

Tsurumi, Y., S. Takeshita, D. Chen, M. Kearney, S. T. Rossow, J. Passeri, J, R. Horowitz, J. F. Symes, and J. M. Isner. 1996. Direct Intramuscular Gene Transfer of Naked DNA Encoding Vascular Endothelial Growth Factor Augments Collateral Development and Tissue Perfusion. Circulation 94:3281-3290.

Tur-Kaspa, R., L. Teicher, B. J. Levine, A. I. Skoultchi, and D. A. Shafritz. 1986. Use of Electroporation To Introduce Biologically Active Foreign Genes Into Primary Rat Hepatocytes. Mol. Cell. Biol. 6:716-718.

Vance, M. L., D. L. Kaiser, W. S. Evans, R. Furlanetto, W. Vale, J. Rivier, and M. O. Thorner. 1985. Pulsatile Growth Hormone Secretion In Normal Man During A Continuous 24-Hour Infusion of Human Growth Hormone Releasing Factor (1-40). Evidence For Intermittent Somatostatin Secretion. J. Clin. Invest. 75:1584-1590.

Vance, M. L., D. L. Kaiser, P. M. Martha, Jr., R. Furlanetto, J. Rivier, W. Vale, and M. O. Thorner. 1989. Lack of hi Vivo Somatotroph Desensitization Or Depletion After 14 Days of Continuous Growth Hormone (GH)-Releasing Hormone Administration In Normal Men and A GH-Deficient Boy. Journal of Clinical Endocrinology & Metabolism 68:22-28.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two Years of Replacement Therapy In Adults With Growth Hormone Deficiency. Clin. Endocrinol. (Oxf) 47:485-494.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer of Naked DNA In the Skeletal Muscles of Animal Models of Muscular Dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of Single Nightly Injections of Growth Hormone-Releasing Hormone (GHRH 1-29) In Healthy Elderly Men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-Kilodalton (kDa) Human Growth Hormone (hGH) Differs From the 22-kDa hGH In the Complex Formation With Cell Surface hGH Receptor and hGH-Binding Protein Circulating In Human Plasma. Mol. Endocrinol. 12:146-156.

Walker, R. F., G. C. Ness, Z. Zhao, and B. B. Bercu. 1994. Effects of Stimulated Growth Hormone Secretion on Age-Related Changes In Plasma Cholesterol and Hepatic Low Density Lipoprotein Messenger RNA Concentrations. Mech. Ageing Dev. 75:215-226.

Wallace, J. D., R. C. Cuneo, M. Bidlingmaier, P. A. Lundberg, L. Carlsson, C. L. Boguszewski, J. Hay, M. Boroujerdi, A. Cittadini, R. Dall, T. Rosen, and C. J. Strasburger. 2001. Changes In Non-22-Kilodalton (kDa) Isoforms of Growth Hormone (GH) After Administration of 22-kDa Recombinant Human GH In Trained Adult Males. J. Clin. Endocrinol. Metab 86:1731-1737.

Wells, D. J. 2004. Gene Therapy Progress and Prospects: Electroporation and Other Physical Methods. Gene Ther. 11:1363-1369.

Wells, K. E., J. Maule, R. Kingston, K. Foster, J. Mcmahon, E. Damien, A. Poole, and D. J. Wells. 1997. Immune Responses, Not Promoter Inactivation, Are Responsible For Decreased Long-Term Expression Following Plasmid Gene Transfer Into Skeletal Muscle. Febs Lett. 407:164-168.

Wolff, J. A., R. W. Malone, P. Williams, W. Chong, G. Acsadi, A. Jani, Felgner, and Pl. 1990. Direct Gene Transfer Into Mouse Muscle In Vivo. Science 247:1465-1468.

Wu, H. K., J. A. Squire, Q. Song, and R. Weksberg. 1997. Promoter-Dependent Tissue-Specific Expressive Nature of Imprinting Gene, Insulin-Like Growth Factor Ii, In Human Tissues. Biochem. Biophys. Res. Commun. 233:221-226.

Yasui, A., K. Oda, H. Usunomiya, K. Kakudo, T. Suzuki, T. Yoshida, H. M. Park, K. Fukazawa, and T. Muramatsu. 2001. Elevated Gastrin Secretion By In Vivo Gene Electroporation In Skeletal Muscle. Int. J. Mol. Med. 8:489-494.

Yutzey, K. E. and S. F. Konieczny. 1992. Different E-Box Regulatory Sequences Are Functionally Distinct When Placed Within the Context of the Troponin I Enhancer. Nucleic Acids Res. 20:5105-5113.

Zachwieja, J. J. and K. E. Yarasheski. 1999. Does Growth Hormone Therapy In Conjunction With Resistance Exercise Increase Muscle Force Production and Muscle Mass In Men and Women Aged 60 Years Or Older? Phys. Ther. 79:76-82.

Zampaglione, I., M. Arcuri, M. Cappelletti, G. Ciliberto, G. Perretta, A. Nicosia, M. N. La, and E. Fattori. 2005. In Vivo DNA Gene Electro-Transfer: A Systematic Analysis of Different Electrical Parameters. J Gene Med. 7:1475-1481.

Zhao-Emonet, J. C., O. Boyer, J. L. Cohen, and D. Klatzmann. 1998. Deletional and Mutational Analyses of the Human Cd4 Gene Promoter: Characterization of A Minimal Tissue-Specific Promoter. Biochim. Biophys. Acta 1442:109-119.

Meyers and Miller, Computer Applic. Biol. Sci., 4: 11-17 (1988).

Smith and Waterman (1981) Adv. Appl. Math. 2: 482.

Needleman S B, Wunsch C D. A General Method Applicable to the Search for Similarities in the Amino Acid Sequence of Two Proteins. J Mol Biol. 1970 March; 48(3):443-53.

Pearson W R, Lipman D J. Improved Tools for Biological Sequence Comparison. Proc Natl Acad Sci USA. 1988 April; 85(8):2444-8.

Higgins D G, Sharp P M. CLUSTAL: A Package For Performing Multiple Sequence Alignment on a Microcomputer. Gene. 1988 Dec. 15; 73(1):237-44.

Higgins D G, Sharp P M. Fast and Sensitive Multiple Sequence Alignments on a Microcomputer. Comput Appl Biosci. 1989 April; 5(2):151-3.

Corpet F. Multiple Sequence Alignment with Hierarchical Clustering. Nucleic Acids Res. 1988 Nov. 25; 16(22):10881-90.

Huang X, Miller W, Schwartz S, Hardison R C. Parallelization of a Local Similarity Algorithm. Comput Appl Biosci. 1992 April; 8(2):155-65.

Pearson W R. Using the FASTA Program to Search Protein and DNA Sequence Databases. Methods Mol Biol. 1994; 24:307-31.

What is claimed is:

1. A method of decreasing serum cholesterol levels in a mammalian subject using non-viral techniques comprising:
   delivering a nucleic acid expression construct that encodes a growth-hormone releasing-hormone ("GHRH") having an amino acid sequence of SEQ ID NO:14 into a tissue of the subject, wherein the GHRH is expressed in vivo in the subject;
   electroporating the tissue, comprising
      penetrating the tissue with a plurality of needle electrodes,
   wherein the plurality of needle electrodes are arranged in a spaced relationship and the tissue comprises muscle cells;
      introducing the nucleic acid expression construct into the tissue via the plurality of needle electrodes in an amount in a range of about 0.05-5 mg; and
      applying an electrical pulse to the plurality of needle electrodes, wherein the electrical pulse allows the nucleic acid expression construct to traverse a muscle cell membrane;
   wherein the nucleic acid expression construct does not contain polylinker, transgene other than GHRH, skeletal alpha-actin promoter, or skeletal alpha actin 3' UTR/NCR.

2. The method of claim 1, wherein the subject is a human.

3. The method of claim 2, further comprising combining the nucleic acid expression construct with a transfection-facilitating polypeptide or a charged polypeptide to form a mixture, and delivering the mixture into the tissue.

4. The method of claim 3, wherein the transfection-facilitating polypeptide or charged polypeptide comprises poly-L-glutamate.

5. The method of claim 2, wherein the nucleic acid expression construct comprises HV-GHRH pA V0224 (SEQ ID NO: 24); pig-wt-GHRH pA V0242 (SEQ ID NO: 25); dog pA V0235 (SEQ ID NO: 26); bovine pA V0236 (SEQ ID NO: 27); cat pA V0238 (SEQ ID NO: 28); TI-GHRH pA V0239 (SEQ ID NO: 29); ovine pA V0240 (SEQ ID NO: 30); chicken pA V0241 (SEQ ID NO:31); horse pA V0249 the plasmid disclosed in FIG. 14; human pA V0243 (SEQ ID NO: 32); mouse pA V0248 (SEQ ID NO: 34); or rat pA V0218 (SEQ ID NO: 35).

6. The method of decreasing serum cholesterol levels in a subject according to claim 2, wherein the electroporating step comprises:
   applying a decentralized constant-current electrical pulse to the plurality of needle electrodes; and
   maintaining the decentralized constant-current electrical pulse in the tissue using a programmable constant-current pulse controller having an impedance meter, wherein the constant-current pulse is constant and substantially independent of a change in a resistance in the tissue.

7. The method of claim 6, wherein the tissue is muscle tissue.

8. The method of claim 6, wherein a sliding needle support guide is used to help prevent the needle electrodes from bending as the plurality of needle electrodes penetrates the selected tissue.

9. The method of claim 6, wherein the plurality of needle electrodes are symmetrically arranged in a circular configuration.

10. The method of claim 6, wherein a hypodermic needle for injecting the nucleic acid expression construct is located in an area between the plurality of needle electrodes.

11. The method of claim 9, wherein the needle electrodes that are arranged without opposing pairs.

* * * * *